US012594343B2

(12) United States Patent
Kraiem

(10) Patent No.: US 12,594,343 B2
(45) Date of Patent: Apr. 7, 2026

(54) TREATMENT OF CANCER

(71) Applicant: INNATE PHARMA, Marseilles (FR)

(72) Inventor: Manel Kraiem, Marseilles (FR)

(73) Assignee: INNATE PHARMA, Marseilles (FR)

( * ) Notice: Subject to any disclaimer, the term of this patent is extended or adjusted under 35 U.S.C. 154(b) by 782 days.

(21) Appl. No.: 17/796,707

(22) PCT Filed: Jan. 28, 2021

(86) PCT No.: PCT/EP2021/051938
§ 371 (c)(1),
(2) Date: Aug. 1, 2022

(87) PCT Pub. No.: WO2021/151984
PCT Pub. Date: Aug. 5, 2021

(65) Prior Publication Data

US 2023/0099149 A1 Mar. 30, 2023

Related U.S. Application Data

(60) Provisional application No. 62/968,175, filed on Jan. 31, 2020.

(51) Int. Cl.
*A61K 47/68* (2017.01)
*A61K 9/00* (2006.01)
*A61P 35/00* (2006.01)

(52) U.S. Cl.
CPC ........ *A61K 47/6889* (2017.08); *A61K 9/0019* (2013.01); *A61K 47/68037* (2023.08); *A61K 47/6849* (2017.08); *A61P 35/00* (2018.01)

(58) Field of Classification Search
None
See application file for complete search history.

(56) References Cited

U.S. PATENT DOCUMENTS

| | | | |
|---|---|---|---|
| 8,637,642 | B2 | 1/2014 | Satpayev et al. |
| 11,312,736 | B1 | 4/2022 | Matray et al. |
| 11,717,575 | B2 | 8/2023 | Yu et al. |
| 2021/0085799 | A1 | 3/2021 | Yu et al. |
| 2021/0353764 | A1 | 11/2021 | Xu et al. |

(Continued)

FOREIGN PATENT DOCUMENTS

| | | |
|---|---|---|
| EP | 1 080 732 | 3/2001 |
| EP | 3 546 448 | 10/2019 |

(Continued)

OTHER PUBLICATIONS

Challita-Eid et al., Cancer Res. May 15, 2016;76 (Year: 2016).*

(Continued)

*Primary Examiner* — Karl J Puttlitz
(74) *Attorney, Agent, or Firm* — SALIWANCHIK, LLOYD & EISENSCHENK

(57) ABSTRACT

The present invention provides antigen-binding proteins capable of binding to Nectin-4 polypeptides conjugated to chemotherapeutic agents, for use in increasing sensitivity of tumors to the chemotherapeutic agents, for use in the treatment of cancers characterized by Nectin expressing tumor cells. In one embodiment, the present invention provides conjugates of an anti-Nectin-4 antibody to a camptothecin analogue, such as exatecan or SN-38, through a cleavable linker.

9 Claims, 9 Drawing Sheets

Specification includes a Sequence Listing.

(56) References Cited

U.S. PATENT DOCUMENTS

| | | | |
|---|---|---|---|
| 2023/0265183 | A1 | 8/2023 | Ren et al. |
| 2024/0325557 | A1 | 10/2024 | Kraiem et al. |

FOREIGN PATENT DOCUMENTS

| | | | | | |
|---|---|---|---|---|---|
| EP | 3 854 816 | | | 7/2021 | |
| EP | 3546448 | B1 | * | 4/2022 | ....... A61K 47/68031 |
| WO | WO 2010/067487 | | | 6/2010 | |
| WO | WO-2012047724 | A1 | * | 4/2012 | .............. A61P 35/00 |
| WO | WO 2015/057699 | | | 4/2015 | |
| WO | WO 2018/226578 | | | 12/2018 | |
| WO | WO 2019/081455 | | | 5/2019 | |
| WO | WO-2019081455 | A1 | * | 5/2019 | ......... A61K 47/6883 |
| WO | WO 2019/236954 | | | 12/2019 | |
| WO | WO 2020/063673 | | | 4/2020 | |
| WO | WO-2020219287 | A1 | * | 10/2020 | ......... A61K 47/6889 |
| WO | WO 2020/233174 | | | 11/2020 | |
| WO | WO 2021/069508 | | | 4/2021 | |
| WO | WO 2021/108353 | | | 6/2021 | |
| WO | WO 2021/213434 | | | 10/2021 | |
| WO | WO 2021/257525 | | | 12/2021 | |
| WO | WO 2022/051591 | | | 3/2022 | |
| WO | WO 2022/058395 | | | 3/2022 | |
| WO | WO 2022/112356 | | | 6/2022 | |
| WO | WO 2023/227660 | | | 11/2023 | |

OTHER PUBLICATIONS

Challita-Eid, P. M. "Enfortumab Vedotin Antibody-Drug Conjugate Targeting Nectin-4 Is a Highly Potent Therapeutic Agent In Multiple Preclinical Cancer Models", *Cancer Research*, Mar. 24, 2016, pp. 3003-3013, vol. 76, No. 10.

Written Opinion in International Application No. PCT/EP2021/051938, May 7, 2021, pp. 1-9.

Mitsui, I. et al. "A New Water-Soluble Camptothecin Derivative, DX-8951f, Exhibits Potent Antitumor Activity against Human Tumors in vitro and in vivo", *Japanese Journal of Cancer Research*, Aug. 1995, pp. 776-782, vol. 86, No. 8.

Takiguchi, S. et al. "Antitumor Effect of DX-8951, a Novel Camptothecin Analog, on Human Pancreatic Tumor Cells and Their CPT-11-resistant Variants Cultured in vitro and Xenografted into Nude Mice", *Japanese Journal of Cancer Research*, Aug. 1997, pp. 760-769, vol. 88, No. 8.

Liew, S. T. et al. "Design, Synthesis and Development of Novel Camptothecin Drugs", *Current Pharmaceutical Design*, 2008, pp. 1078-1097, vol. 14, No. 11.

Rosenberg, J. E. et al. "Pivotal Trial of Enfortumab Vedotin in Urothelial Carcinoma After Platinum and Anti-Programmed Death 1/Programmed Death Ligand 1 Therapy", *J. Clin. Oncol.*, published online Jul. 29, 2019, pp. 2592-2600 and supplemental pp. 1-13, vol. 37, Issue 29.

De Jonge, M. J. A. et al. "Phase II study on 9-nitrocamptothecin (RFS 2000) in patients with advanced or metastatic urothelial tract tumors", *Invest. New Drugs*, Aug. 2004, pp. 329-333, vol. 22, No. 3.

Sarfaty, M. et al. "Antibody-Drug Conjugates in Urothelial Carcinomas", *Current Oncology Reports*, Feb. 1, 2020, pp. 1-8, vol. 22, Article No. 13.

Nejadmoghaddam, M-R. et al. "Antibody-Drug Conjugates: Possibilities and Challenges", *Avicenna J Med Biotechnol.*, Jan.-Mar. 2019, pp. 3-23, vol. 11, No. 1.

Beck, A. et al. "Strategies and challenges for the next generation of antibody-drug conjugates", *Nat Rev Drug Discov.*, published online Mar. 17, 2017, pp. 315-337, vol. 16, No. 5.

Wong, J. L. et al. "Targeting nectin-4 by antibody-drug conjugates for the treatment of urothelial carcinoma", *Expert Opin Biol Ther.*, Jul. 3, 2021, pp. 1-21, vol. 21, No. 7.

Reymond, N. et al. "Nectin4/PRR4, A New Afadin-Associated Member of The Nectin Family That Trans-Interacts with Nectin1/PRR1 through V Domain Interaction", *Journal of Biological Chemistry*, Nov. 16, 2001, pp. 43205-43215, vol. 276, No. 46.

M-Rabet, M. et al. "Nectin-4: a new prognostic biomarker for efficient therapeutic targeting of primary and metastatic triple-negative breast cancer", *Annals of Oncology*, published online Dec. 20, 2016, pp. 769-776, vol. 28, No. 4.

Zeindler, J. et al. "Nectin-4 Expression Is an Independent Prognostic Biomarker and Associated with Better Survival in Triple-Negative Breast Cancer" *Frontiers in Medicine*, Sep. 13, 2019, pp. 1-7, vol. 6, Article 200.

Chu, C. E. et al. "Heterogeneity in NECTIN4 expression across molecular subtypes of urothelial cancer mediates sensitivity to enfortumab vedotin", *Clin Cancer Res.*, Sep. 15, 2021, pp. 1-16, vol. 27, No. 18.

Abou-Alfa, G.K. "Randomized Phase III Study of Exatecan and Gemcitabine Compared With Gemcitabine Alone in Untreated Advanced Pancreatic Cancer", Sep. 20, 2006, pp. 4441-4447, vol. 24, No. 7.

Communication of a notice of opposition, Application No. 21702624.4, Sep. 15, 2025, pp. 1-47.

Communication of a notice of opposition, Application No. 21702624.4, Sep. 17, 2025, pp. 1-72.

Highlights of Prescribing Information for Padcev (enfortumab vedotin-ejfv) Dec. 2019, pp. 1-19.

Chen, R. et al. "CD30 Downregulation, MMAE Resistance, and MDR1 Upregulation Are All Associated with Resistance to Brentuximab Vedotin" *Mol Cancer Ther*, Jun. 2015, pp. 1376-1384, vol. 14, No. 6.

Modi, S. et al. "Trastuzumab Deruxtecan in Previously Treated HER2-Positive Breast Cancer" *N Engl J Med*, Feb. 13, 2020, pp. 1-20, vol. 382, No. 7.

Ogitani, Y. et al. "DS-8201a, A Novel HER2-Targeting ADC with a Novel DNA Topoisomerase I Inhibitor, Demonstrates a Promising Antitumor Efficacy with Differentiation from T-DM1" *Clin Cancer Res*, Oct. 15, 2016, pp. 5097-5108, vol. 22, No. 20.

FDA grants accelerated approval to enfortumab vedotin-ejfv for metastatic urothelial cancer, https://www.fda.gov/drugs/resources-information-approved-drugs/fda-grants-accelerated-approval-enfortumab-vedotin-ejfv-metastatic-urothelial-cancer Dec. 19, 2019, p. 1.

Loganzo, F. et al. "Mechanisms of Resistance to Antibody-Drug Conjugates" *Mol Cancer Ther*, Dec. 1, 2016, pp. 2825-2834, vol. 15, No. 12.

Amiri-Kordestani, L et al. "FDA Approval: Ado-Trastuzumab Emtansine for the Treatment of Patients with HER2-Positive Metastatic Breast Cancer" *Clin Cancer Res*, Sep. 1, 2014, pp. 4436-4441, vol. 20, No. 17, pp. 4436-4441.

FDA approves fam-trastuzumab deruxtecan-nxki for unresectable or metastatic HER2-positive breast cancer, https://www.fda.gov/drugs/resources-information-approved-drugs/fda-approves-fam-trastuzumab-deruxtecan-nxki-unresectable-or-metastatic-her2-positive-breast-cancer, Dec. 20, 2019, pp. 1-2.

Reches, A. et al. "Nectin4 is a novel TIGIT ligand which combines checkpoint inhibition and tumor specificity" *J Immunother Cancer*, Jun. 4, 2020, pp. 1-9, vol. 8, No. 1, e000266.

Nakada, T. et al. "Novel antibody drug conjugates containing exatecan derivative-based cytotoxic payloads" *Bioorg Med Chem Lett*, Mar. 15, 2016, Advanced Online Publication (corresponds to vol. 26, No. 6, pp. 1542-1545).

Li, F. et al. "Intracellular Released Payload Influences Potency and Bystander-Killing Effects of Antibody-Drug Conjugates in Preclinical Models" *Cancer Res*, May 1, 2016, pp. 2710-2719, vol. 76, No. 9.

Klumper, N. et al. "Membranous NECTIN-4 Expression Frequently Decreases during Metastatic Spread of Urothelial Carcinoma and Is Associated with Enfortumab Vedotin Resistance" *Clin Cancer Res*, Apr. 15, 2023, pp. 1496-1505, vol. 29, No. 8.

Delpeut, S. et al. "The V domain of dog PVRL4 (nectin-4) mediates canine distemper virus entry and virus cell-to-cell spread" *Virology*, Feb. 28, 2014, pp. 109-117, vol. 454-455.

Yaghoubi et al. "Potential drugs used in the antibody-drug conjugate (ADC) architecture for cancer therapy" *J Cell Physiol*, Jun. 18, 2019, pp. 1-34, vol. 235, No. 1.

(56) References Cited

OTHER PUBLICATIONS

Hunter, F. W. et al. "Mechanisms of resistance to trastuzumab emtansine (T-DM1) in HER2-positive breast cancer" *British Journal of Cancer*, Dec. 16, 2019, pp. 603-612, vol. 122.
Anami, Y. et al. "Glutamic acid-valine-citrulline linkers ensure stability and efficacy of antibody-drug conjugates in mice" *Nat Commun*, Jun. 28, 2018, pp. 1-9, vol. 9, No. 2512.
Definitions of Cancer Progression and Cancer Recurrence, NHS Dictionary, obtained May 28, 2024, pp. 1-3.
Alexander, S. et al. "Cancer invasion and resistance: interconnected processes of disease progression and therapy failure" *Trends in Molecular Medicine*, Jan. 2012, pp. 13-26, vol. 18, No. 1.
Garcia-Alonso, S. et al. "Resistance to Antibody-Drug Conjugates" *Cancer Res*, May 1, 2018, pp. 2159-2165, vol. 78, No. 9.
You, F. et al. "Topoisomerase Inhibitors and Targeted Delivery in Cancer Therapy" *Current Topics in Med Chem*, 2019, pp. 713-729, vol. 19, No. 9.
De Jager, R. et al. "DX-8951f: Summary of Phase I Clinical Trials" *Annals New York Academy of Sciences*, Jan. 25, 2006, pp. 260-273, vol. 922.
Moukharskaya, J. et al. "Topoisomerase 1 Inhibitors and Cancer Therapy", *Hematol Oncol Clin N Am*, 2012, pp. 507-525, vol. 26, No. 3.
Ogitani, Y. et al. "Bystander killing effect of DS-8201a, a novel anti-human epidermal growth factor receptor 2 antibody-drug conjugate, in tumors with human epidermal growth factor receptor 2 heterogeneity" *Cancer Science*, Jul. 2016, pp. 1039-1046, vol. 107, No. 7.
Ogitani, Y. et al. "Wide application of a novel topoisomerase I inhibitor-based drug conjugation technology" *Bioorganic & Medicinal Chemistry Letters*, Aug. 27, 2016, pp. 5069-5072, vol. 26, No. 20.
Hammood, M et al. "Impact of Endocytosis Mechanisms for the Receptors Targeted by the Currently Approved Antibody-Drug Conjugates (ADCs)—A Necessity for Future ADC Research and Development" *Pharmaceuticals*, Jul. 15, 2021, pp. 1-33, vol. 14, No. 674.
Lopez, M. et al. "Etx-22, a Novel Nectin-4-Directed Antibody-Drug Conjugate, Demonstrates Safety and Potent Antitumor Activity in Low-Nectin-4-Expressing Tumors" *Cancer Res Commun*, Nov. 1, 2024, pp. 2998-3012, vol. 4, No. 11.
Cabaud, O. et al. "Overcoming Resistance to Anti-Nectin-4 Antibody-Drug Conjugate" *Mol Cancer Ther*, Jul. 2022, pp. 1227-1235, vol. 21, No. 7.
EMA EPAR for Padcev, date unknown, pp. 1-50.
Burke, P. J et al. "Design, Synthesis, and Biological Evaluation of Antibody-Drug Conjugates Comprised of Potent Camptothecin Analogues" *Bioconjug Chem.*, May 26, 2009, pp. 1242-1250, vol. 20, No. 6.
Buecheler, J. et al. Impact of Payload Hydrophobicity on the Stability of Antibody-Drug Conjugates, *Molecular Pharmaceutics*, May 29, 2018, pp. 2656-2664, vol. 15, No. 7.
Chia, C. S. B. et al. "A Patent Review on FDA-Approved Antibody-Drug Conjugates, Their Linkers and Drug Payloads" *ChemMedChem.*, Jun. 3, 2022, pp. 1-11, vol. 17, No. 11, e202200032.
Opposition Brief, Japanese Application No. 2022-546059, Jan. 7, 2026, pp. 1-56 (machine translation of Opposition Brief).
Beck, A. et al. "Strategies and challenges forthe next generation of antibody-drug conjugates", Nat Rev Drug Discov., published online Mar. 17, 2017, pp. 1-23, vol. 16, No. 5, Exhibit Kō 1.
Modi, S. et al. "Trastuzumab Deruxtecan in Previously Treated HER2-Positive Breast Cancer" N Engl J Med, Dec. 11, 2019, pp. 610-621, vol. 382, No. 7, Exhibit Kō 2.
Hunter, F. W. et al. "Mechanisms of resistance to trastuzumab emtansine (T-DM1) in HER2-positive breast cancer" British Journal of Cancer, published online Dec. 16, 2019, pp. 603-612, vol. 122, Exhibit Kō 3.
Rosenberg, J. E. et al. "Pivotal Trial of Enfortumab Vedotin in Urothelial Carcinoma After Platinum and Anti-Programmed Death 1/Programmed Death Ligand 1 Therapy", J. Clin. Oncol., published online Jul. 29, 2019, pp. 2592-2600 and supplemental pp. 1-13, vol. 37, Issue 29, Exhibit Kō 4.
HIGHLIGHTS OF PRESCRIBING INFORMATION for PADCEV (enfortumab vedotin-ejfv) Dec. 2019, pp. 1-19, Exhibit Kō 5.

* cited by examiner

| | Sample Name | Subset Name | Count | Median : FL2-A |
|---|---|---|---|---|
| | SUM185_N4_003.fcs | Single Cells | 6611 | 4326 |
| | SUM185_HER2_004.fcs | Single Cells | 6505 | 2880 |
| | SUM185_IC_002.fcs | Single Cells | 6713 | 94,5 |
| | SUM185_US_001.fcs | Single Cells | 6832 | 71,5 |

SEQUENCE LISTING

```
<160> NUMBER OF SEQ ID NOS: 16

<210> SEQ ID NO 1
<211> LENGTH: 510
<212> TYPE: PRT
<213> ORGANISM: homo sapiens

<400> SEQUENCE: 1

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
            20                  25                  30

Glu Leu Glu Thr Ser Asp Val Val Thr Val Val Leu Gly Gln Asp Ala
        35                  40                  45

Lys Leu Pro Cys Phe Tyr Arg Gly Asp Ser Gly Glu Gln Val Gly Gln
    50                  55                  60

Val Ala Trp Ala Arg Val Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Pro Arg Asn Pro Leu Asp Gly Ser Val
            100                 105                 110

Leu Leu Arg Asn Ala Val Gln Ala Asp Glu Gly Glu Tyr Glu Cys Arg
        115                 120                 125

Val Ser Thr Phe Pro Ala Gly Ser Phe Gln Ala Arg Leu Arg Leu Arg
    130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
            180                 185                 190

Ser Arg Ser Phe Lys His Ser Arg Ser Ala Ala Val Thr Ser Glu Phe
        195                 200                 205

His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Ile Gly Arg Glu Gly Ala Met Leu Lys Cys Leu Ser
            260                 265                 270

Glu Gly Gln Pro Pro Pro Ser Tyr Asn Trp Thr Arg Leu Asp Gly Pro
        275                 280                 285

Leu Pro Ser Gly Val Arg Val Asp Gly Asp Thr Leu Gly Phe Pro Pro
    290                 295                 300

Leu Thr Thr Glu His Ser Gly Ile Tyr Val Cys His Val Ser Asn Glu
305                 310                 315                 320
```

-continued

Phe Ser Ser Arg Asp Ser Gln Val Thr Val Asp Val Leu Asp Pro Gln
325 330 335

Glu Asp Ser Gly Lys Gln Val Asp Leu Val Ser Ala Ser Val Val Val
340 345 350

Val Gly Val Ile Ala Ala Leu Leu Phe Cys Leu Leu Val Val Val Val
355 360 365

Val Leu Met Ser Arg Tyr His Arg Arg Lys Ala Gln Gln Met Thr Gln
370 375 380

Lys Tyr Glu Glu Glu Leu Thr Leu Thr Arg Glu Asn Ser Ile Arg Arg
385 390 395 400

Leu His Ser His His Thr Asp Pro Arg Ser Gln Pro Glu Glu Ser Val
405 410 415

Gly Leu Arg Ala Glu Gly His Pro Asp Ser Leu Lys Asp Asn Ser Ser
420 425 430

Cys Ser Val Met Ser Glu Glu Pro Glu Gly Arg Ser Tyr Ser Thr Leu
435 440 445

Thr Thr Val Arg Glu Ile Glu Thr Gln Thr Glu Leu Leu Ser Pro Gly
450 455 460

Ser Gly Arg Ala Glu Glu Glu Glu Asp Gln Asp Glu Gly Ile Lys Gln
465 470 475 480

Ala Met Asn His Phe Val Gln Glu Asn Gly Thr Leu Arg Ala Lys Pro
485 490 495

Thr Gly Asn Gly Ile Tyr Ile Asn Gly Arg Gly His Leu Val
500 505 510

<210> SEQ ID NO 2
<211> LENGTH: 113
<212> TYPE: PRT
<213> ORGANISM: homo sapiens

<400> SEQUENCE: 2

Gly Glu Leu Glu Thr Ser Asp Val Val Thr Val Val Leu Gly Gln Asp
1 5 10 15

Ala Lys Leu Pro Cys Phe Tyr Arg Gly Asp Ser Gly Glu Gln Val Gly
20 25 30

Gln Val Ala Trp Ala Arg Val Asp Ala Gly Glu Gly Ala Gln Glu Leu
35 40 45

Ala Leu Leu His Ser Lys Tyr Gly Leu His Val Ser Pro Ala Tyr Glu
50 55 60

Gly Arg Val Glu Gln Pro Pro Pro Pro Arg Asn Pro Leu Asp Gly Ser
65 70 75 80

Val Leu Leu Arg Asn Ala Val Gln Ala Asp Glu Gly Glu Tyr Glu Cys
85 90 95

Arg Val Ser Thr Phe Pro Ala Gly Ser Phe Gln Ala Arg Leu Arg Leu
100 105 110

Arg

<210> SEQ ID NO 3
<211> LENGTH: 117
<212> TYPE: PRT
<213> ORGANISM: artificial
<220> FEATURE:
<223> OTHER INFORMATION: synthetic

<400> SEQUENCE: 3

Glu Val Gln Leu Val Glu Ser Gly Gly Gly Leu Val Gln Pro Gly Gly

-continued

```
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Asp Glu Asp Thr Ala Val Tyr Tyr Cys
                85                  90                  95

Ala Arg Ala Tyr Tyr Tyr Gly Met Asp Val Trp Gly Gln Gly Thr Thr
            100                 105                 110

Val Thr Val Ser Ser
        115


<210> SEQ ID NO 4
<211> LENGTH: 111
<212> TYPE: PRT
<213> ORGANISM: Artificial
<220> FEATURE:
<223> OTHER INFORMATION: Synthetic

<400> SEQUENCE: 4

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Gly Trp
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gly Gly Thr Lys Val Glu Ile Lys Arg Thr Val Ala
            100                 105                 110


<210> SEQ ID NO 5
<211> LENGTH: 447
<212> TYPE: PRT
<213> ORGANISM: Artificial
<220> FEATURE:
<223> OTHER INFORMATION: Synthetic

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80
```

```
Leu Gln Met Asn Ser Leu Arg Asp Glu Asp Thr Ala Val Tyr Tyr Cys
                85                  90                  95

Ala Arg Ala Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445
```

<210> SEQ ID NO 6
<211> LENGTH: 214
<212> TYPE: PRT
<213> ORGANISM: Artificial
<220> FEATURE:
<223> OTHER INFORMATION: Synthetic

<400> SEQUENCE: 6

-continued

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Gly Trp
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 115
<212> TYPE: PRT
<213> ORGANISM: mus musculus

<400> SEQUENCE: 7

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Thr Met Asp Trp Val Lys Gln Ser His Gly Lys Ser Leu Glu Trp Ile
        35                  40                  45

Gly Asp Ile Asn Pro Asn Asn Asp Val Thr Met Tyr Asn Glu Lys Phe
    50                  55                  60

Lys Gly Arg Ala Thr Leu Thr Val Asp Lys Ser Ser Ser Thr Ala Tyr
65                  70                  75                  80

Met Glu Val Arg Ser Leu Thr Ser Glu Asp Thr Ala Val Tyr Tyr Cys
                85                  90                  95

Val Arg Gly Arg Gly Phe Ala Tyr Trp Gly Gln Gly Thr Leu Val Thr
            100                 105                 110

Val Ser Ala
        115


<210> SEQ ID NO 8
<211> LENGTH: 111
<212> TYPE: PRT
<213> ORGANISM: mus musculus
```

<400> SEQUENCE: 8

Asp Ile Val Leu Thr Gln Ser Pro Ala Ser Leu Ile Val Ser Leu Gly
1               5                   10                  15

Gln Arg Ala Thr Ile Ser Cys Arg Ala Ser Gln Ser Val Ser Thr Ser
            20                  25                  30

Ser Asn Ser Tyr Met His Trp Tyr Gln Gln Lys Pro Gly Gln Pro Pro
        35                  40                  45

Lys Leu Leu Ile Arg Phe Ala Ser Asn Leu Glu Ser Gly Val Pro Ala
    50                  55                  60

Arg Phe Ser Gly Ser Gly Ser Gly Thr Tyr Phe Thr Leu Asn Ile His
65                  70                  75                  80

Pro Val Glu Glu Glu Asp Ser Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 9
<211> LENGTH: 116
<212> TYPE: PRT
<213> ORGANISM: Mus musculus

<400> SEQUENCE: 9

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Thr Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Glu Leu Ile His Ala Met Asp Asn Trp Gly Gln Gly Thr Ser Val
            100                 105                 110

Thr Val Ser Ser
        115

<210> SEQ ID NO 10
<211> LENGTH: 106
<212> TYPE: PRT
<213> ORGANISM: Mus musculus

<400> SEQUENCE: 10

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Asn Ser Pro Gln Leu Leu Val
        35                  40                  45

Phe Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

-continued

```
Glu Asp Phe Gly Thr Tyr Tyr Cys Gln His Phe Trp Gly Thr Pro Thr
                85                  90                  95

Phe Gly Gly Gly Thr Lys Leu Glu Ile Lys
            100                 105


<210> SEQ ID NO 11
<211> LENGTH: 90
<212> TYPE: PRT
<213> ORGANISM: Homo sapiens

<400> SEQUENCE: 11

Pro Pro Leu Pro Ser Leu Asn Pro Gly Pro Ala Leu Glu Glu Gly Gln
1               5                   10                  15

Gly Leu Thr Leu Ala Ala Ser Cys Thr Ala Glu Gly Ser Pro Ala Pro
            20                  25                  30

Ser Val Thr Trp Asp Thr Glu Val Lys Gly Thr Thr Ser Ser Arg Ser
        35                  40                  45

Phe Lys His Ser Arg Ser Ala Ala Val Thr Ser Glu Phe His Leu Val
    50                  55                  60

Pro Ser Arg Ser Met Asn Gly Gln Pro Leu Thr Cys Val Val Ser His
65                  70                  75                  80

Pro Gly Leu Leu Gln Asp Gln Arg Ile Thr
                85                  90


<210> SEQ ID NO 12
<211> LENGTH: 103
<212> TYPE: PRT
<213> ORGANISM: Homo sapiens

<400> SEQUENCE: 12

Ala Ser Val Arg Gly Leu Glu Asp Gln Asn Leu Trp His Ile Gly Arg
1               5                   10                  15

Glu Gly Ala Met Leu Lys Cys Leu Ser Glu Gly Gln Pro Pro Pro Ser
            20                  25                  30

Tyr Asn Trp Thr Arg Leu Asp Gly Pro Leu Pro Ser Gly Val Arg Val
        35                  40                  45

Asp Gly Asp Thr Leu Gly Phe Pro Pro Leu Thr Thr Glu His Ser Gly
    50                  55                  60

Ile Tyr Val Cys His Val Ser Asn Glu Phe Ser Ser Arg Asp Ser Gln
65                  70                  75                  80

Val Thr Val Asp Val Leu Asp Pro Gln Glu Asp Ser Gly Lys Gln Val
                85                  90                  95

Asp Leu Val Ser Ala Ser Val
            100


<210> SEQ ID NO 13
<211> LENGTH: 14
<212> TYPE: PRT
<213> ORGANISM: Artificial
<220> FEATURE:
<223> OTHER INFORMATION: Synthetic

<400> SEQUENCE: 13

Gly Lys Pro Ile Pro Asn Pro Leu Leu Gly Leu Asp Ser Thr
1               5                   10


<210> SEQ ID NO 14
<211> LENGTH: 479
<212> TYPE: PRT
<213> ORGANISM: Artificial
```

-continued

<220> FEATURE:
<223> OTHER INFORMATION: Synthetic

<400> SEQUENCE: 14

Gly Glu Leu Glu Thr Ser Asp Val Val Thr Val Val Leu Gly Gln Asp
1               5                   10                  15

Ala Lys Leu Pro Cys Phe Tyr Arg Gly Asp Ser Gly Glu Gln Val Gly
            20                  25                  30

Gln Val Ala Trp Ala Arg Val Asp Ala Gly Glu Gly Ala Gln Glu Leu
        35                  40                  45

Ala Leu Leu His Ser Lys Tyr Gly Leu His Val Ser Pro Ala Tyr Glu
    50                  55                  60

Gly Arg Val Glu Gln Pro Pro Pro Pro Arg Asn Pro Leu Asp Gly Ser
65                  70                  75                  80

Val Leu Leu Arg Asn Ala Val Gln Ala Asp Glu Gly Glu Tyr Glu Cys
                85                  90                  95

Arg Val Ser Thr Phe Pro Ala Gly Ser Phe Gln Ala Arg Leu Arg Leu
            100                 105                 110

Arg Val Leu Val Pro Pro Leu Pro Ser Leu Asn Pro Gly Pro Ala Leu
        115                 120                 125

Glu Glu Gly Gln Gly Leu Thr Leu Ala Ala Ser Cys Thr Ala Glu Gly
    130                 135                 140

Ser Pro Ala Pro Ser Val Thr Trp Asp Thr Glu Val Lys Gly Thr Thr
145                 150                 155                 160

Ser Ser Arg Ser Phe Lys His Ser Arg Ser Ala Ala Val Thr Ser Glu
                165                 170                 175

Phe His Leu Val Pro Ser Arg Ser Met Asn Gly Gln Pro Leu Thr Cys
            180                 185                 190

Val Val Ser His Pro Gly Leu Leu Gln Asp Gln Arg Ile Thr His Ile
        195                 200                 205

Leu His Val Ser Phe Leu Ala Glu Ala Ser Val Arg Gly Leu Glu Asp
    210                 215                 220

Gln Asn Leu Trp His Ile Gly Arg Glu Gly Ala Met Leu Lys Cys Leu
225                 230                 235                 240

Ser Glu Gly Gln Pro Pro Pro Ser Tyr Asn Trp Thr Arg Leu Asp Gly
                245                 250                 255

Pro Leu Pro Ser Gly Val Arg Val Asp Gly Asp Thr Leu Gly Phe Pro
            260                 265                 270

Pro Leu Thr Thr Glu His Ser Gly Ile Tyr Val Cys His Val Ser Asn
        275                 280                 285

Glu Phe Ser Ser Arg Asp Ser Gln Val Thr Val Asp Val Leu Asp Pro
    290                 295                 300

Gln Glu Asp Ser Gly Lys Gln Val Asp Leu Val Ser Ala Ser Val Val
305                 310                 315                 320

Val Val Gly Val Ile Ala Ala Leu Leu Phe Cys Leu Leu Val Val Val
                325                 330                 335

Val Val Leu Met Ser Arg Tyr His Arg Arg Lys Ala Gln Gln Met Thr
            340                 345                 350

Gln Lys Tyr Glu Glu Glu Leu Thr Leu Thr Arg Glu Asn Ser Ile Arg
        355                 360                 365

Arg Leu His Ser His His Thr Asp Pro Arg Ser Gln Pro Glu Glu Ser
    370                 375                 380

Val Gly Leu Arg Ala Glu Gly His Pro Asp Ser Leu Lys Asp Asn Ser
385                 390                 395                 400

Ser Cys Ser Val Met Ser Glu Glu Pro Glu Gly Arg Ser Tyr Ser Thr
405 410 415

Leu Thr Thr Val Arg Glu Ile Glu Thr Gln Thr Glu Leu Leu Ser Pro
420 425 430

Gly Ser Gly Arg Ala Glu Glu Glu Glu Asp Gln Asp Glu Gly Ile Lys
435 440 445

Gln Ala Met Asn His Phe Val Gln Glu Asn Gly Thr Leu Arg Ala Lys
450 455 460

Pro Thr Gly Asn Gly Ile Tyr Ile Asn Gly Arg Gly His Leu Val
465 470 475

<210> SEQ ID NO 15
<211> LENGTH: 363
<212> TYPE: PRT
<213> ORGANISM: Artificial
<220> FEATURE:
<223> OTHER INFORMATION: Synthetic

<400> SEQUENCE: 15

Pro Pro Leu Pro Ser Leu Asn Pro Gly Pro Ala Leu Glu Glu Gly Gln
1 5 10 15

Gly Leu Thr Leu Ala Ala Ser Cys Thr Ala Glu Gly Ser Pro Ala Pro
20 25 30

Ser Val Thr Trp Asp Thr Glu Val Lys Gly Thr Thr Ser Ser Arg Ser
35 40 45

Phe Lys His Ser Arg Ser Ala Ala Val Thr Ser Glu Phe His Leu Val
50 55 60

Pro Ser Arg Ser Met Asn Gly Gln Pro Leu Thr Cys Val Val Ser His
65 70 75 80

Pro Gly Leu Leu Gln Asp Gln Arg Ile Thr His Ile Leu His Val Ser
85 90 95

Phe Leu Ala Glu Ala Ser Val Arg Gly Leu Glu Asp Gln Asn Leu Trp
100 105 110

His Ile Gly Arg Glu Gly Ala Met Leu Lys Cys Leu Ser Glu Gly Gln
115 120 125

Pro Pro Pro Ser Tyr Asn Trp Thr Arg Leu Asp Gly Pro Leu Pro Ser
130 135 140

Gly Val Arg Val Asp Gly Asp Thr Leu Gly Phe Pro Pro Leu Thr Thr
145 150 155 160

Glu His Ser Gly Ile Tyr Val Cys His Val Ser Asn Glu Phe Ser Ser
165 170 175

Arg Asp Ser Gln Val Thr Val Asp Val Leu Asp Pro Gln Glu Asp Ser
180 185 190

Gly Lys Gln Val Asp Leu Val Ser Ala Ser Val Val Val Val Gly Val
195 200 205

Ile Ala Ala Leu Leu Phe Cys Leu Leu Val Val Val Val Val Leu Met
210 215 220

Ser Arg Tyr His Arg Arg Lys Ala Gln Gln Met Thr Gln Lys Tyr Glu
225 230 235 240

Glu Glu Leu Thr Leu Thr Arg Glu Asn Ser Ile Arg Arg Leu His Ser
245 250 255

His His Thr Asp Pro Arg Ser Gln Pro Glu Glu Ser Val Gly Leu Arg
260 265 270

Ala Glu Gly His Pro Asp Ser Leu Lys Asp Asn Ser Ser Cys Ser Val
275 280 285

```
Met Ser Glu Glu Pro Glu Gly Arg Ser Tyr Ser Thr Leu Thr Thr Val
    290                 295                 300

Arg Glu Ile Glu Thr Gln Thr Glu Leu Leu Ser Pro Gly Ser Gly Arg
305                 310                 315                 320

Ala Glu Glu Glu Glu Asp Gln Asp Glu Gly Ile Lys Gln Ala Met Asn
                325                 330                 335

His Phe Val Gln Glu Asn Gly Thr Leu Arg Ala Lys Pro Thr Gly Asn
            340                 345                 350

Gly Ile Tyr Ile Asn Gly Arg Gly His Leu Val
        355                 360


<210> SEQ ID NO 16
<211> LENGTH: 263
<212> TYPE: PRT
<213> ORGANISM: Artificial
<220> FEATURE:
<223> OTHER INFORMATION: Synthetic

<400> SEQUENCE: 16

Ala Ser Val Arg Gly Leu Glu Asp Gln Asn Leu Trp His Ile Gly Arg
1               5                   10                  15

Glu Gly Ala Met Leu Lys Cys Leu Ser Glu Gly Gln Pro Pro Pro Ser
            20                  25                  30

Tyr Asn Trp Thr Arg Leu Asp Gly Pro Leu Pro Ser Gly Val Arg Val
        35                  40                  45

Asp Gly Asp Thr Leu Gly Phe Pro Pro Leu Thr Thr Glu His Ser Gly
    50                  55                  60

Ile Tyr Val Cys His Val Ser Asn Glu Phe Ser Ser Arg Asp Ser Gln
65                  70                  75                  80

Val Thr Val Asp Val Leu Asp Pro Gln Glu Asp Ser Gly Lys Gln Val
                85                  90                  95

Asp Leu Val Ser Ala Ser Val Val Val Val Gly Val Ile Ala Ala Leu
            100                 105                 110

Leu Phe Cys Leu Leu Val Val Val Val Val Leu Met Ser Arg Tyr His
        115                 120                 125

Arg Arg Lys Ala Gln Gln Met Thr Gln Lys Tyr Glu Glu Glu Leu Thr
    130                 135                 140

Leu Thr Arg Glu Asn Ser Ile Arg Arg Leu His Ser His His Thr Asp
145                 150                 155                 160

Pro Arg Ser Gln Pro Glu Glu Ser Val Gly Leu Arg Ala Glu Gly His
                165                 170                 175

Pro Asp Ser Leu Lys Asp Asn Ser Ser Cys Ser Val Met Ser Glu Glu
            180                 185                 190

Pro Glu Gly Arg Ser Tyr Ser Thr Leu Thr Thr Val Arg Glu Ile Glu
        195                 200                 205

Thr Gln Thr Glu Leu Leu Ser Pro Gly Ser Gly Arg Ala Glu Glu Glu
    210                 215                 220

Glu Asp Gln Asp Glu Gly Ile Lys Gln Ala Met Asn His Phe Val Gln
225                 230                 235                 240

Glu Asn Gly Thr Leu Arg Ala Lys Pro Thr Gly Asn Gly Ile Tyr Ile
                245                 250                 255

Asn Gly Arg Gly His Leu Val
            260
```

TREATMENT OF CANCER

CROSS-REFERENCE TO RELATED APPLICATIONS

This application is the U.S. national stage application of International Patent Application No. PCT/EP2021/051938, filed Jan. 28, 2021, which claims the benefit of U.S. Provisional Application No. 62/968,175 filed 31 Jan. 2020; which is incorporated herein by reference in its entirety; including any drawings.

REFERENCE TO SEQUENCE LISTING

The present application is being filed along with a Sequence Listing in electronic format. The Sequence Listing is provided as a file entitled "Nectin-4-1_ST25", created Jan. 25, 2021 which is 29,392 bytes in size. The information in the electronic format of the Sequence Listing is incorporated herein by reference in its entirety.

FIELD OF THE INVENTION

The present invention provides antigen-binding proteins capable of binding to Nectin-4 polypeptides conjugated to camptothecins for use in the treatment of cancers characterized by Nectin-4-expressing tumor cells, including in particular in tumors different levels of Nectin-4 expression including low and heterogeneous expression.

BACKGROUND OF THE INVENTION

In the United States in 2016, it was estimated that there were over 70,000 new diagnoses of bladder cancer, with about 16,000 deaths. Urothelial cancers encompass carcinomas of the bladder, ureters, and renal pelvis, which occur at a ratio of 50:3:1, respectively. Cancer of the urothelium is a multifocal process. Patients with cancer of the upper urinary tract have a 30% to 50% chance of developing cancer of the bladder at some point in their lives. Bladder cancer occurs when the cells in the bladder start to grow unusually or uncontrollably. The most common type of bladder cancer is called urothelial carcinoma (UC). In UC, unusual growth takes place on the inside lining (urothelium) of the bladder. As the disease progresses, it may spread. It can spread to the areas around the bladder or to other parts of the body (metastasis). This is called advanced urothelial carcinoma.

Urothelial carcinoma (UC) is characterized by increased expression of a range of different cell surface antigens, thus offering opportunities for specific therapeutic targeting with use of antibody-drug conjugates (ADCs). Among the surface antigens, several antigens have shown to be amenable to development of ADCs, including TROP-2 (human trophoblast cell-surface antigen), SLITRK family proteins (e.g. SLITRK6), EpCAM, HER2, TF-Ag (Thomsen-Friedrich antigen), FGF1V, Fn14 (FGF-inducible 14), PSMA (prostate-specific membrane antigen) and Nectin-4 (poliovirus receptor-related protein 4, also known as PVRL4.

Nectin-4 was initially cloned from human trachea by the Lopez group in 2001 (see Reymond et al. (2001) J. Biol. Chem. 276(46):43205-15). It has been reported that copy number gain of the Nectin-4 gene is a frequent event in carcinogenesis and further that it can promote epithelial-to-mesenchymal transition, invasion and metastasis. While nectin-4 protein expression is limited in healthy tissues, is expressed at significantly higher levels in several tumors, and it is particularly over-expressed in breast cancer, including triple negative breast cancer (TNBC) (See M-Rabet et al. Ann Oncol. 2017 Apr. 1; 28(4):769-776), pancreatic cancer and in UC. However, nectin-4 is also expressed in non-small cell lung cancer, ovarian cancer, head and neck squamous cell carcinoma and esophageal cancer tumor specimens. Challita-Eid et al. (2016) Cancer Res. 76(10): 3003-3013 reported that moderate to strong staining by immunohistochemistry (H-score≥100) in bladder (60%) and breast (53%) tumor tissues. Zeindler et al. 2019 Front. Med. 6:200 reported that a high expression of Nectin-4 was present in 86 (58%) of the 148 TNBC cases.

Challita-Eid et al. (2016), supra, developed an anti-Nectin-4 antibody conjugated to the highly potent microtubule-disrupting agent MMAE based on antibody AGS-22. The work gave rise to the ADC drug candidate enfortumab vedotin (see U.S. Pat. No. 8,637,642 and PCT publication No. WO2012/047724, Agensys Inc.) which has yielded promising results in human clinical trials in treatment of patients with locally advanced or metastatic urothelial cancer who have previously received a platinum-containing chemotherapy in the neoadjuvant/adjuvant, locally advanced, or metastatic setting and a PD-1/PD-L1 checkpoint inhibitor. Several other groups have also proposed anti-Nectin-4 agents bound to a variety of toxic agents. PCT patent application WO2018/158398 (INSERM) reports several anti-Nectin-4 antibodies and proposes potential coupling to a range of cytotoxic agents. Similarly, U.S. Pat. No. 8,637,642 (Agensys Inc.) also provides anti-Nectin-4 antibodies and proposes potential coupling to a range of cytotoxic agents. Yet further, Bicycle Therapeutics' has reported development of an anti-Nectin-4 targeting agent comprised of a Nectin-4 binding protein conjugated to a cytotoxic auristatin (MMAE) payload via a cleavable valine-citrulline dipeptide.

The ADCs for which there has been reports of development for UC include sacituzumab govitecan (IMMU-132, anti-TROP2), enfortumab vedotin (ASG-22ME, anti-Nectin-4), sirtratumab verdotin (ASG-15ME, anti-SLITRK6) for advanced UC, and oportuzumab monatox (VB4-845, anti-EpCAM) for non-muscle invasive bladder cancer.

Unfortunately, while ADCs have shown promising results, many targeted therapies do not provide sufficient and/or lasting anti-tumor responses patients. For example, while enfortumab vedotin (anti-Nectin-4 ADC) has shown impressive therapeutic responses with an ORR (objective response rate) of 44% and CR (complete response rate) of 12% in UC in the EV-201 Phase 2 study (2019), about half of the patients discontinued treatment. Most of the discontinuation was due to progressive disease as assessed by RECIST (48%) or clinical symptoms (5%). Also, 18% patients that discontinued experienced adverse events, notably neuropathy. The Nectin-4-targeted ADCs therefore have limitations, and there is a need in the art for improved benefit to patients afflicted with UC and other cancers.

In UC, individuals are generally first treated with cisplatin-based regimens (with or without radiation) both when the cancer has not spread to distant parts of the body, or when the cancer has spread. Camptothecin compounds are generally not used in the treatment of UC. de Jonge et al., 2004 Invest New Drugs 22: 329-333 studied the camptothecin analogue RFS2000 in patients with advanced or metastatic urothelial tract tumors. De Jonge et al. 2004 concluded that it did not exert significant activity in patients with advanced/metastatic urothelial tract tumors failing prior chemotherapy, and that the results of this study do not suggest further investigation of RFS2000. A great number of camptothecin analogues have been made over the last few decades, among them exatecan. Abou-Alfa et al., 2006 Journal of Clinical Oncology 24(27): 4441-4447 evaluated exatecan in the treatment of pancreatic cancer in a phase 3 trial of 349 patients, finding that exatecan in addition to gemcitabine was not superior in efficacy to gemcitabine alone.

SUMMARY OF THE INVENTION

In one aspect, the present disclosure provides a Nectin-4 binding agent conjugated to an exatecan molecule, as well as use thereof in the treatment of Nectin-4-expressing cancers, notably UC, breast cancer (e.g. TNBC), non-small cell lung cancer, pancreatic cancer, ovarian cancer, head and neck squamous cell carcinoma or an esophageal cancer. In one aspect, the present disclosure provides highly potent linkers comprising an intracellularly-cleavable di-peptide, a self-eliminating spacer and a camptothecin analogue. The highly potent linkers can be conjugated to an antibody that binds a tumor antigen. Accordingly, also provided are antibodies and antibody compositions conjugated to such linkers (e.g., where the antibody binds a tumor antigen, optionally Nectin-4). In one aspect, the present disclosure provides methods of treatment that can be used in individuals having a Nectin-4-expressing cancer irrespective of the level of Nectin-4 expression on tumor cells.

In one aspect, the present disclosure provides methods of treatment that can be used advantageously in individuals whose tumor cells express P-glycoprotein (Pgp).

In one aspect, the present disclosure provides methods of treatment that can be used advantageously in individuals having received prior treatment with a chemotherapeutic agent (e.g. a chemotherapeutic agent transported by P-glycoprotein (Pgp), a platinum agent (e.g., oxaliplatin, cisplatin, carboplatin, nedaplatin, phenanthriplatin, picoplatin, satraplatin), a taxane (e.g., Paclitaxel (Taxol) and docetaxel (Taxotere)).

In one aspect, the present disclosure provides methods of treatment that can be used advantageously in an individual whose tumor or cancer has resistance, that is not responsive to or that has progressed following treatment with a composition comprising an anti-HER2 antibody (e.g. trastuzumab, an ADC comprising the heavy and light variable regions, CDRs or polypeptide chains trastuzumab).

In one aspect, the present disclosure provides methods of treatment that can be used to mediate an anti-tumor effect in an individual at doses that are low or lower than those employed for conventional anti-Nectin-4 ADCs, e.g., less than 5 mg/kg body weight less than 3 mg/kg body weight, at less than 1.25 mg/kg body weight, less than 1 mg/kg body weight, less than 125 mg flat dose.

In one aspect, the present disclosure provides methods of treatment that can be used in an individual who has existing neuropathy, diabetes or hyperglycemia, cardiac insufficiency, an ocular pathology.

In one aspect, the present disclosure provides methods of treatment that can be used in an individual having a Nectin-4-expressing cancer characterized by low or moderate levels of tumor cell expression of Nectin-4 polypeptides (e.g. expression of Nectin-4 polypeptides at the tumor cell membrane).

Provided is a treatment comprising administration of a Nectin-4 binding agent conjugated to a camptothecin analogue or derivative (e.g., a 5-ring or 6-ring camptothecin, an exatecan or SN-38 molecule). Nectin-4 is generally expressed on tumor cells, however, expression levels of Nectin-4 can influence the therapeutic effect of anti-Nectin-4 agents such as ADCs. While Nectin-4 expression in tumor cells can be very high in some individuals (e.g., as assessed by immunohistochemistry), other individuals will have disease in which tumor cell Nectin-4 expression is low or moderate, or below the level considered as high expressing, and who in turn may be less responsive or not responsive to agents such as enfortumab verdotin. The ability to treat individuals having a Nectin-4-expressing cancer characterized by non-high levels of tumor cell Nectin-4-expression (e.g., low or moderate levels) provides advantage for use in the broader population without limitation to high Nectin-4 expression levels, e.g. treating a population of subjects characterized by subjects having different levels of Nectin-4 expression on tumor cells (for example, low or medium Nectin-4 subjects and high Nectin-4 subjects). This advantage is of interest in Nectin-4 expressing cancers known to often (but not always) show very high tumor Nectin-4 expression such as UC, and potentially of even greater interest in Nectin-4 expressing cancers where there is significant diversity in levels of tumor cell Nectin-4 expression such as breast cancer (e.g. TNBC, Her2+ breast cancer), non-small cell lung cancer, pancreatic cancer, ovarian cancer, head and neck squamous cell carcinoma or an esophageal cancer. In one embodiment, the Nectin-4 expressing cancer is additionally characterized by expression of Her2 polypeptides (e.g. Her2 overexpressing or high-expressing cancers, Her2-low expressing cancers).

The treatment of the disclosure can for example be used advantageously in cancer types known to be characterized by tumors within individuals in which tumor cells having high heterogeneity in the levels of tumor antigen (e.g. Nectin-4) at their surface.

In one aspect, the present disclosure provides a method of treating an individual having a Nectin-4-expressing cancer characterized by low or moderate levels of tumor cell Nectin-4-expression. The patient may have an advanced or refractory cancer, or may have an earlier stage cancer in which tumor Nectin-4 expression remains low or moderate. The treatment comprises administration of a Nectin-4 binding agent conjugated to a camptothecin analogue or derivative, e.g. an exatecan or SN-38 molecule. In one embodiment, the tumor is characterized by low or moderate Nectin-4 expression as determined by an immunohistochemistry score, e.g. an H-score of no more than, or less than, 290, 250, 200, 180, 170, 160, 150, 140, 130, 120 or 100. In one embodiment, said individual has an urothelial cancer or a breast cancer. In one embodiment, said individual has a non-small cell lung cancer, a pancreatic cancer, an ovarian cancer, a head and neck squamous cell carcinoma or an esophageal cancer. In one embodiment, the cancer or tumor is advanced recurrent or metastatic cancer, optionally an advanced recurrent or metastatic urothelial cancer. In one aspect, the present disclosure provides a method of treating a population of individuals having Nectin-4-expressing cancer, wherein the population includes individuals having a cancer or tumor characterized by low or moderate Nectin-4 expression as determined by an immunohistochemistry score, e.g. an H-score of no more than, or less than, 290, 250, 200, 180, 170, 160, 150, 140, 130, 120 or 100.

In one aspect, the anti-Nectin-4 antibody or antibody fragment is conjugated to a camptothecin analogue via an intracellularly-cleavable (e.g., protease cleavable) oligopeptide (e.g. di-, tri-, tetra- or penta-peptide). In one aspect, the anti-Nectin-4 antibody or antibody fragment is conjugated to a camptothecin analogue) via an intracellularly-cleavable (e.g. protease-cleavable) di-, tri-, tetra- or penta-peptide and a self-eliminating spacer (e.g. the self-eliminating spacer positioned between the intracellularly-cleavable peptide and the camptothecin. In one aspect, the anti-Nectin-4 antibody or antibody fragment is conjugated to a camptothecin analogue) via an intracellularly-cleavable (e.g., protease cleavable) di- or tri-peptide and a self-eliminating spacer. In one aspect, the anti-Nectin-4 antibody or antibody fragment is conjugated to a camptothecin analogue) via an intracellularly-cleavable (e.g., protease cleavable) tetra- or penta-peptide and a self- or non-self-eliminating spacer.

Optionally the antibody is functionalized with a linker-toxin of any one of Formulae I to XI.

In one aspect, the camptothecin analogue is an exatecan or SN-38 molecule.

In one aspect, the present disclosure provides a Nectin-4 binding protein, antibody or antibody fragment conjugated (e.g. covalently bound to) to a camptothecin, e.g. a camptothecin analogue, an exatecan or exatecan derivative or a SN-38 molecule.

In one aspect, the present disclosure provides a method of treating an individual having a cancer, the method comprising treating said individual with a Nectin-4 binding agent conjugated to a camptothecin analogue or derivative, e.g. an exatecan or SN-38 molecule. In one embodiment, said individual has an urothelial cancer or a breast cancer.

In one aspect, the present disclosure provides a method of treating an individual without a prior step of determining whether the individual is suitable for treatment based on tumor cell expression level of Nectin-4, the method comprising treating said individual with a Nectin-4 binding agent conjugated to a camptothecin analogue or derivative, e.g. an exatecan or SN-38 molecule. In one embodiment, said individual has an urothelial cancer or a breast cancer.

In one aspect, the present disclosure provides a Nectin-4 binding agent conjugated to a camptothecin analogue or derivative, e.g. an exatecan or SN-38 molecule, for use in treatment of cancer in a population of individuals that comprises both individuals having tumor characterized by high levels of Nectin-4 on tumor cells and individuals having tumor characterized by low levels of Nectin-4 on tumor cells. In one embodiment, said individual has an urothelial cancer or a breast cancer.

In one aspect, the present disclosure provides a method of treating an individual having a cancer (e.g. a Nectin-4-expressing cancer), wherein the individual has a cancer that is resistant, has not responded, has relapsed and/or progressed despite (e.g. during or following) treatment with an antibody or antigen binding molecule (e.g. a Nectin-4 antibody or antigen binding molecule) conjugated to an auristatin or MMAE molecule (e.g., enfortumab vedotin), the method comprising treating said individual with a Nectin-4 binding agent conjugated to a camptothecin analogue or derivative, e.g. an exatecan or SN-38 molecule. In one embodiment, said individual has an urothelial cancer, a breast cancer, a non-small cell lung cancer, pancreatic cancer, ovarian cancer, head and neck squamous cell carcinoma or an esophageal cancer. In one embodiment, the cancer or tumor is an advanced recurrent or metastatic cancer, optionally an advanced recurrent or metastatic urothelial cancer.

In one aspect, the present disclosure provides a method of treating an individual having a cancer (e.g. a Nectin-4-expressing cancer), wherein the individual has a locally advanced or metastatic urothelial cancer and has previously received treatment with an antibody or antigen-binding agent conjugated to an auristatin or MMAE molecule (e.g., enfortumab vedotin), the method comprising treating said individual with a Nectin-4 binding agent conjugated to a camptothecin analogue or derivative, e.g. an exatecan or SN-38 molecule.

In one aspect, the present disclosure provides a method of reducing or preventing drug resistance in an individual having a cancer (e.g. a Nectin-4-expressing cancer), the method comprising treating said individual with a Nectin-4 binding agent conjugated to a camptothecin analogue or derivative, e.g. an exatecan or SN-38 molecule.

In any embodiment herein, the individual can be specified to be resistant, non-responsive, relapsed and/or progressed following prior treatment with an antibody conjugated to an auristatin or MMAE molecule (e.g., enfortumab vedotin).

In any embodiment herein, the individual can be specified to have a HER2-positive tumor or cancer (e.g., a Nectin-4-positive, HER2-positive tumor or cancer), optionally a HER2 over-expressing or HER2 high-expressing tumor or cancer, optionally a HER2 low-expressing tumor or cancer. In other embodiments herein, the individual can be specified to have a Her2-negative tumor or cancer. Optionally, the tumor or cancer is a triple-negative breast cancer (TNBC).

In one aspect, the present disclosure provides a method of treating an individual having a cancer (e.g. a Nectin-4-expressing cancer) characterized by tumor cells that express Her2 polypeptides (e.g., tumor cells expressing at their surface both Nectin-4 and Her2), the method comprising treating said individual with a Nectin-4 binding agent conjugated (e.g. via an intracellularly cleavable linker) to a camptothecin analogue or derivative, e.g. an exatecan or SN-38 molecule. In one embodiment, the cancer is characterized by tumor cells that over-express or express at their surface high levels of Her2. In one embodiment, the cancer is characterized by tumor cells that express at their surface low levels of Her2. In one embodiment, the method further comprises treating the individual (e.g. administering to the individual in combination) with an antibody that binds a Her2 polypeptide (e.g. trastuzumab, pertuzumab); optionally wherein the antibody that binds Her2 is an ADC; optionally wherein the antibody that binds Her2 is conjugated to a cytotoxic agent, optionally an auristatin, a maytansinoid (e.g. DM1) or a camptothecin analogue or derivative (e.g. exatecan or derivative thereof, SN-38); optionally wherein the antibody that binds Her2 is trastuzumab emtansine or trastuzumab deruxtecan (DS-8201a). In one embodiment, the individual has a breast cancer. In one embodiment, the individual has a gastric cancer. In one embodiment, the individual has a colorectal cancer. In one embodiment, the individual has a pancreatic cancer. In one embodiment, the individual has a bladder cancer. In one embodiment, the individual has a head and neck cancer.

The Nectin-4 binding agent conjugated to a camptothecin analogue or derivative can be advantageously administered 1-4 times per month, for example once every two weeks, once every three weeks or once every four weeks.

The Nectin-4 binding agent conjugated to a camptothecin analogue or derivative, e.g. an exatecan or SN-38 molecule, can be advantageously administered at a dose of 0.1-10 or 1-10 mg/kg body weight, 1-4 times per month, for example once every two weeks, once every three weeks or once every four weeks.

In one aspect, the present disclosure provides a Nectin-4 binding agent conjugated (e.g. covalently bound to) to a camptothecin analogue or derivative, e.g. an exatecan or exatecan derivative, or an SN-38 molecule.

In any embodiment herein, a Nectin-4 binding agent conjugated (e.g. covalently bound to) to a camptothecin analogue or derivative, e.g. an exatecan or SN-38 molecule, can be characterized as comprising an antigen binding protein (e.g., antibody, non-antibody peptide or protein scaffold) that specifically binds to a human Nectin-4 polypeptide having one or more amino acid residues (e.g. cysteine, lysine, glutamine residues, a non-natural amino acid residue) functionalized, via a linker, with a molecule comprising the structure of Compounds 1 or 2, or functionalized with the linker-camptothecin molecule of Formulas I or II. In any embodiment herein, a anti-Nectin-4 antibody or antibody fragment can be characterized as being functionalized with a linker-camptothecin molecule having a structure of Formulas III, IV, V, VI, VII, VII, IX, X or XI, or with any of Compounds 3 to 17.

In one embodiment, the anti-Nectin-4 antibody or antibody fragment conjugated to a camptothecin analogue is a Nectin-4 binding antibody or antibody fragment conjugated to an exatecan molecule, e.g. a molecule having the structure of Compound 1 (1a or 1 b). In one embodiment, the Nectin-4 binding antibody or antibody fragment conjugated to a camptothecin analogue is a Nectin-4 binding antibody or antibody fragment conjugated to a SN-38 molecule, e.g., a molecule having the structure of Compound 2. In one embodiment, the Nectin-4 binding antibody or antibody fragment can be characterized as comprising an antibody that specifically binds to a human Nectin-4 polypeptide having one or more amino acid residues (e.g. cysteine, lysine, glutamine or non-natural amino acid residues) functionalized, via a linker (e.g. a cleavable linker molecule with or without an additional spacer, for example spacer (Y') described herein), with a molecule having the structure:

Compound 1a

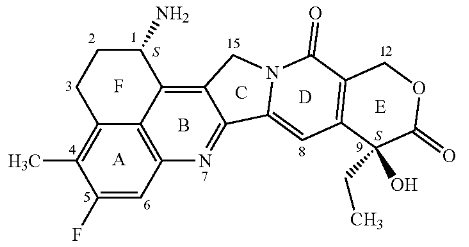

or

Compound 1b

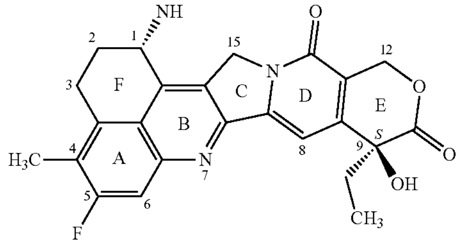

or

Compound 2

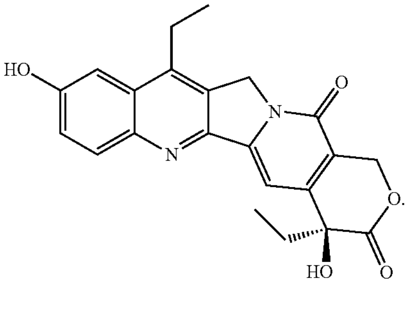

In one embodiment, the Nectin-4 binding protein, antibody or antibody fragment conjugated to a cytotoxic agent can be specified as being an immunoconjugate represented by Formula (I):

Ab-X—Z Formula (I)

wherein,

Ab is an antigen binding protein (e.g. antibody) that specifically binds to a human Nectin-4 polypeptide;

X is a linker molecule which connects Ab and Z (e.g., is covalently bound to each of Ab and Z), wherein X comprises a moiety that is cleavable, e.g., under physiological conditions, optionally under intracellular conditions, optionally a protease-cleavable di-, tri-, tetra- or penta-peptide, optionally wherein X further comprises a self-eliminating or non-self-eliminating spacer system (Y') positioned between the cleavable moiety and Z, optionally wherein X further comprises a spacer (Y) positioned between the Ab and the cleavable moiety; and Z is a camptothecin analogue, optionally an exatecan molecule or a SN-38 molecule.

In one embodiment, provided herein are cleavable peptide-containing linkers (e.g. oligopeptide, or di-, tri-, tetra- or penta-peptide containing linkers) and linker-toxin molecules that can be conjugated to an antibody or other antigen binding peptide or protein, e.g. an antibody or non-antibody peptide or protein scaffold that binds a tumor antigen (e.g. Nectin-4 or another suitable tumor antigen), as well as antibodies and antibody compositions conjugated to such linkers, and method of use thereof in the treatment of cancer. In one embodiment, a di-peptide-containing linker-toxin molecule comprises a structure (X-Z), wherein X is a linker molecule comprising a reactive group, optionally protected, suitable for reacting with a complementary reactive group on an antigen binding protein, a spacer moiety (Y) positioned between the reactive group and the cleavable dipeptide, a cleavable di-peptide selected from valine-citrulline, valine-alanine or phenylalanine-lysine, a self-eliminating spacer system (Y') positioned between the cleavable di-peptide and Z, and wherein Z is a camptothecin analogue, optionally an exatecan molecule or a SN-38 molecule. Further provided are methods of conjugating such a cleavable peptide-containing linkers to an antigen binding protein.

In one embodiment, an antibody conjugated to a camptothecin analogue can be specified as being an immunoconjugate represented by Formula (I):

Ab-X—Z Formula (I)

wherein,

Ab is an antigen binding protein (e.g. antibody) that specifically binds to a human tumor antigen;

X is a linker molecule which connects Ab and Z (e.g., is covalently bound to each of Ab and Z), wherein X comprises a valine-citrulline, valine-alanine or phenylalanine-lysine dipeptide, wherein X further comprises a self-eliminating or non-self-eliminating spacer system (Y') positioned between the cleavable moiety and Z, and wherein X further comprises a spacer (Y) positioned between the Ab and the cleavable moiety; and Z is a camptothecin analogue, optionally an exatecan molecule or a SN-38 molecule.

In one embodiment, provided is a method of delivering or targeting a camptothecin analogue to a tumor or a method of releasing a camptothecin analogue in a tumor (e.g. in a subject having cancer), the method comprising administering to a subject having a cancer an immunoconjugate represented by Formula (I):

Ab-X—Z Formula (I)

wherein,

Ab is an antigen binding protein (e.g. antibody) that specifically binds to a human tumor antigen;

X is a linker molecule which connects Ab and Z (e.g., is covalently bound to each of Ab and Z), wherein X comprises a valine-citrulline, valine-alanine or phenylalanine-lysine dipeptide, wherein X further comprises a self-eliminating or non-self-eliminating spacer system (Y') positioned between the cleavable moiety and Z, and wherein X further comprises a spacer (Y) positioned between the Ab and the cleavable moiety; and Z is a camptothecin analogue, optionally an exatecan molecule or a SN-38 molecule.

In one embodiment, the antibody or Nectin-4 binding agent conjugated to a camptothecin analogue can be specified as being an immunoconjugate represented by Formula (II):

$Ab\text{-}(X—(Z)_n)_m$ Formula (II)

wherein,

Ab is an antigen binding protein (e.g. antibody) that specifically binds to a human Nectin-4 polypeptide or other tumor antigen;

X is a linker molecule which connects Ab and Z, wherein X comprises a moiety that is cleavable, e.g., under physiological conditions, optionally under intracellular conditions, optionally a protease-cleavable di-, tri-, tetra- or penta-peptide, optionally wherein X further comprises a self-eliminating or non-self-eliminating spacer system (Y') positioned between the cleavable moiety and Z, optionally wherein X further comprises a spacer (Y) positioned between the Ab and the cleavable moiety;

Z is a camptothecin analogue, optionally Z is a molecule comprising an exatecan molecule or a SN-38 molecule, e.g., a molecule having the structure of Compounds 1 or 2;

n is 1; and m is from 4 to 8, or optionally m is an integer selected from among 4, 5, 6, 7 or 8.

In one embodiment, a Nectin-4 binding agent conjugated to a camptothecin analogue can be characterized as a composition of immunoconjugates represented by Formula (II):

$Ab\text{-}(X—(Z)_n)_m$ Formula (II)

wherein,

Ab is an antigen binding protein (e.g. antibody) that specifically binds to a human Nectin-4 polypeptide;

X is a molecule which connects Ab and Z, wherein X comprises a moiety that is cleavable, e.g., under physiological conditions, optionally under intracellular conditions, optionally a protease-cleavable di-, tri-, tetra- or penta-peptide, optionally wherein X further comprises a self-eliminating or non-self-eliminating spacer system (Y') positioned between the cleavable moiety and Z, optionally wherein X further comprises a spacer (Y) positioned between the Ab and the cleavable moiety;

Z is a camptothecin analogue, optionally Z is a molecule comprising an exatecan molecule or a SN-38 molecule;

wherein n is 1, and at least 50%, 60%, 70%, 80%, 90%, 95%, 98% or 99% of immunoconjugates in the composition have an m (the number of X—Z moieties) that is between 2 and 4, between 4 and 8, optionally between 6 and 8. Optionally at least 50%, 60%, 70%, 80%, 90%, 95%, 98% or 99% of immunoconjugates in the composition have an m that is, or that is at least, 4, 6, 7 or 8.

In Formulae I or II, the (X—Z) moiety can optionally be characterized having a structure of any of Formulae III to XI or of any of Compounds 3-17.

In Formulae I or II, molecule X or spacer Y can optionally be specified as comprising a reactive group (R) or a residue of the reaction of a reactive group (R) with an amino acid of the antigen binding protein (e.g., antibody) or with a complementary reactive group (R') that is attached to an amino acid of the antigen binding protein (e.g., antibody).

In any embodiment herein, the exatecan molecule can be specified as being bound to linker (X) via the amine at position 1 of the exatecan (NH replaces $NH_2$ at position 1 when the exatecan molecule is incorporated in a linker). In any embodiment herein, the SN-38 molecule can be specified as being bound to linker (X) via the OH at position 9 (O replaces OH at position 9 when the SN-38 molecule shown in Compound 2 is incorporated in a linker).

In one embodiment, the Nectin-4 binding agent conjugated to an exatecan can be characterized as comprising an antibody that specifically binds to a human Nectin-4 polypeptide having one or more amino acid residues (e.g. cysteine residues, glutamine residues) functionalized, via a spacer (Y), with a linker-exatecan molecule comprising the following structure:

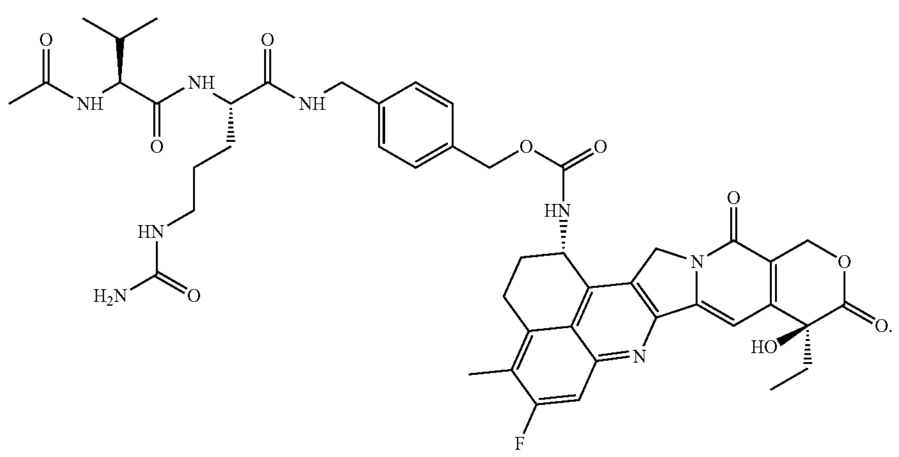 [SMILES: CC[C@@]1(O)C(=O)OCc2c1cc1n(c2=O)Cc2c-1nc1cc(F)c(C)c3c1c2[C@@H](NC(=O)OCc1ccc(CNC(=O)[C@H](CCCNC(N)=O)NC(=O)[C@@H](NC(C)=O)C(C)C)cc1)CC3]

In one embodiment, the Nectin-4 binding agent conjugated to an exatecan can be characterized as comprising an antibody that specifically binds to a human Nectin-4 polypeptide having one or more amino acid residues (e.g. cysteine residues, glutamine residues) functionalized, via a spacer (Y), with a linker-exatecan comprising the following structure:

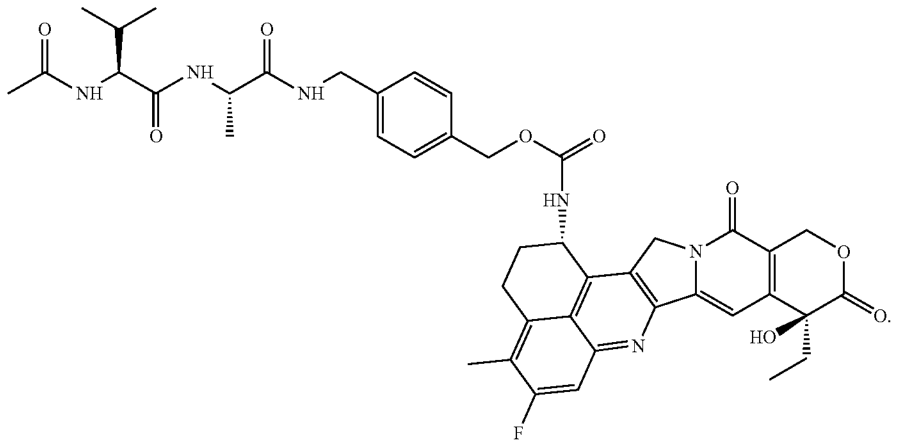 [SMILES: CC[C@@]1(O)C(=O)OCc2c1cc1n(c2=O)Cc2c-1nc1cc(F)c(C)c3c1c2[C@@H](NC(=O)OCc1ccc(CNC(=O)[C@H](C)NC(=O)[C@@H](NC(C)=O)C(C)C)cc1)CC3]

In one embodiment, the Nectin-4 binding agent conjugated to an exatecan can be characterized as comprising an antibody that specifically binds to a human Nectin-4 polypeptide having one or more amino acid residues (e.g. cysteine residues, glutamine residues) functionalized, via a spacer (Y), with a linker-exatecan molecule comprising the following structure:

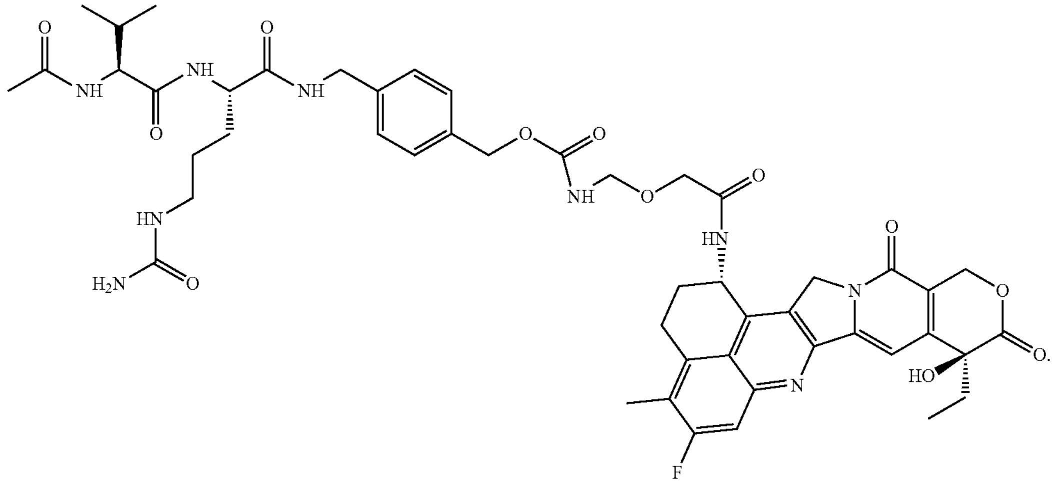 [SMILES: CC[C@@]1(O)C(=O)OCc2c1cc1n(c2=O)Cc2c-1nc1cc(F)c(C)c3c1c2[C@@H](NC(=O)COCNC(=O)OCc1ccc(CNC(=O)[C@H](CCCNC(N)=O)NC(=O)[C@@H](NC(C)=O)C(C)C)cc1)CC3]

In one embodiment, the Nectin-4 binding agent conjugated to an exatecan can be characterized as comprising an antibody that specifically binds to a human Nectin-4 polypeptide having one or more amino acid residues (e.g. cysteine residues, glutamine residues) functionalized, via a spacer (Y), with a linker-exatecan molecule comprising the following structure:

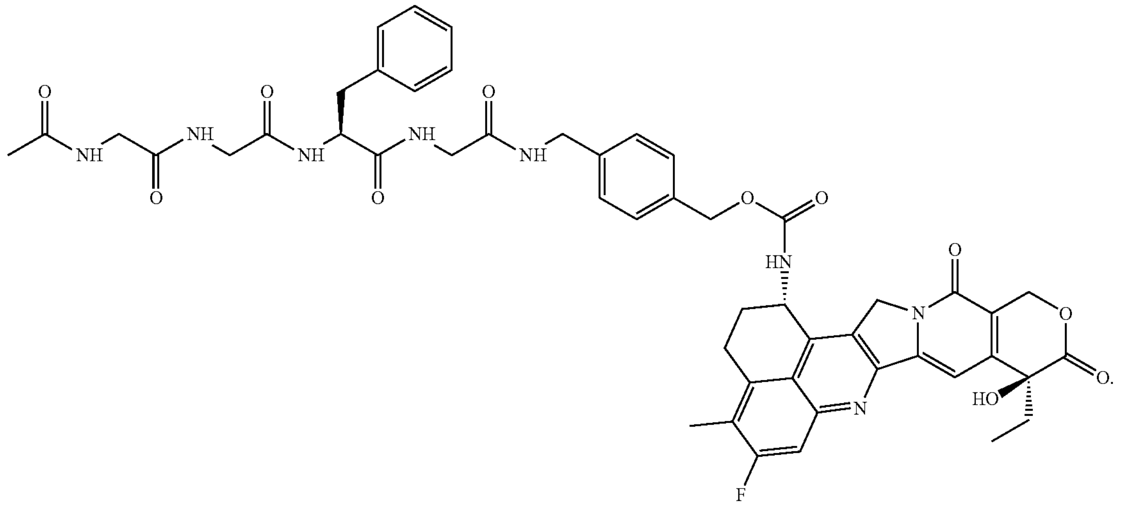 [SMILES: CC[C@@]1(O)C(=O)OCc2c1cc1n(c2=O)Cc2c-1nc1cc(F)c(C)c3c1c2[C@@H](NC(=O)OCc1ccc(CNC(=O)CNC(=O)[C@H](Cc2ccccc2)NC(=O)CNC(=O)CNC(C)=O)cc1)CC3]

Spacer (Y) can be specified as being or comprising a substituted or unsubstituted alkyl or heteroalkyl chain, optionally wherein Y has a chain length of 2-100 atoms or 2-40 atoms, optionally 2-30, 2-20, 4-40, 4-30 or 4-20 atoms, optionally where one or more atoms can be other than carbon, for example oxygen, sulfur, nitrogen, or other atoms, optionally wherein any carbon of the chain is substituted with an alkoxy, hydroxyl, alkylcarbonyloxy, alkyl-S—, thiol, alkyl-C(O)S—, amine, alkylamine, amide, or alkylamide. For example Y may comprise one or more ethylene oxide monomers, optionally Y comprises a polyethylene oxide moiety, optionally Y comprises a structure $-(CH_2CH_2O)_x-$ where x is 1 to 12, optionally 1 to 8, optionally 1 to 6.

In one aspect, the present disclosure provides a treatment showing improved (lower) drug resistance compared to existing anti-Nectin-4 ADC therapies (e.g. an anti-Nectin-4 antibody conjugated to an auristatin; enfortumab verdotin). In one aspect, provided is a method of treating and/or preventing a cancer and/or killing tumor cells in an individual in need thereof, wherein the treatment comprises 2, 3, 4, 5, 6, 7, 8, 9 or 10 or more administrations of a Nectin-4 binding agent conjugated to a camptothecin analogue (e.g. an exatecan or SN-38 molecule) at a frequency of 1 to 2 times per month (e.g. once every two weeks, once every three weeks or once every four weeks).

In one aspect, the present disclosure provides a method of treating and/or preventing a cancer and/or killing tumor cells in an individual in need thereof, or a method of delivering and/or releasing a camptothecin molecule in a tumor in an individual, comprising treating said individual with Nectin-4 binding protein (e.g. antibody or antibody fragment) conjugated to a camptothecin molecule such as camptothecin analogue (e.g., an anti-Nectin-4 antibody or antibody fragment conjugated to one or more camptothecin moieties), optionally wherein the camptothecin is an exatecan or SN-38. In one embodiment, said individual has a Nectin-4-expressing tumor, optionally wherein the tumor is an HER2-expressing tumor or a HER-negative tumor, e.g. an urothelial cancer, a breast cancer, a non-small cell lung cancer, pancreatic cancer, ovarian cancer, head and neck squamous cell carcinoma or an esophageal cancer. In one embodiment, the cancer or tumor is advanced recurrent or metastatic cancer, optionally an advanced recurrent or metastatic urothelial cancer. In one embodiment, the cancer or tumor is a triple-negative breast cancer (TNBC).

In one aspect of any embodiment herein, the individual has received prior treatment with radiotherapy, surgery, chemotherapy, and/or treatment with a biological agent.

Provided also are compositions of immunoconjugates of the disclosure. Provided also are pharmaceutically acceptable compositions and kits comprising the immunoconjugates of the disclosure, and typically one or more additional ingredients that can be active ingredients or inactive ingredients that promote formulation, delivery, stability, or other characteristics of the composition (e.g., various carriers). Provided also are methods of screening, testing and making immunoconjugates and ADCs.

These aspects are more fully described in, and additional aspects, features, and advantages will be apparent from, the description of the invention provided herein.

DETAILED DESCRIPTION

Definitions

Figure 1:
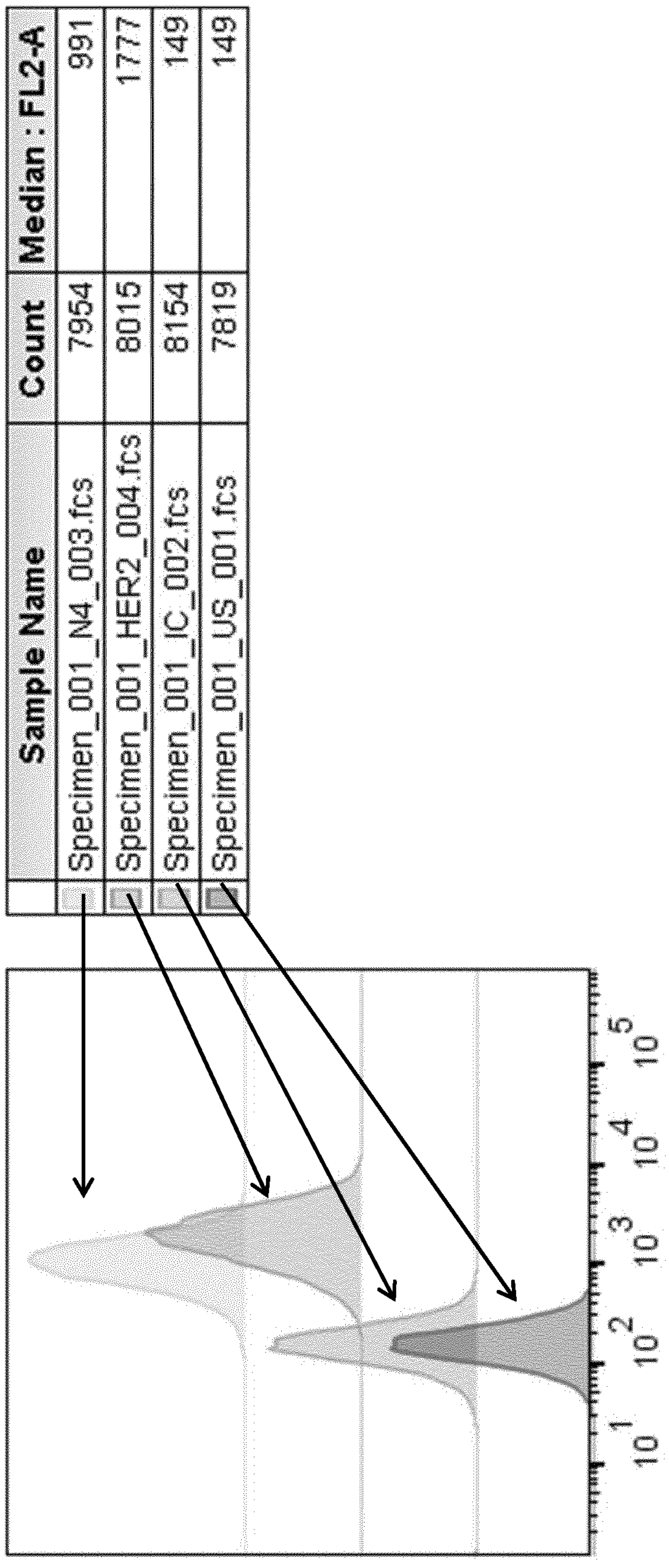
FIG. 1 shows expression levels of HER2 and Nectin-4 polypeptides at the surface of SUM190 human breast cancer tumor cells, as determined by FACS (MFI:Mean of fluorescence intensity). The SUM190 tumor cells expressed HER2 at low to moderate levels (median fluorescence units 1777) as well as Nectin-4 at lower levels (median 991 fluorescence units).

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

"Nectin-4" and "Nectin-4 polypeptide" refer to a protein or polypeptide encoded by the NECTIN4 gene (see Uniprot accession number Q96NY8) or by a cDNA prepared from such a gene. Any naturally occurring isoform, allele or variant is encompassed by the term Nectin-4 polypeptide (e.g., an Nectin-4 polypeptide 95%, 98% or 99% identical to SEQ ID NO: 1, or to a contiguous sequence of at least 100, 200, 300, 400 or 500 amino acid residues thereof). The 510 amino acid residue sequence of canonical human Nectin-4 (isoform 1), including the 31 amino acid signal peptide, is shown as follows:

```
                                             (SEQ ID NO: 1)
MPLSLGAEMW GPEAWLLLLL LLASFTGRCP AGELETSDVV

TVVLGQDAKL PCFYRGDSGE QVGQVAWARV DAGEGAQELA

LLHSKYGLHV SPAYEGRVEQ PPPPRNPLDG SVLLRNAVQA

DEGEYECRVS TFPAGSFQAR LRLRVLVPPL PSLNPGPALE

EGQGLTLAAS CTAEGSPAPS VTWDTEVKGT TSSRSFKHSR

SAAVTSEFHL VPSRSMNGQP LTCVVSHPGL LQDQRITHIL

HVSFLAEASV RGLEDQNLWH IGREGAMLKC LSEGQPPPSY

NWTRLDGPLP SGVRVDGDTL GFPPLTTEHS GIYVCHVSNE

FSSRDSQVTV DVLDPQEDSG KQVDLVSASV VVVGVIAALL

FCLLVVVVVL MSRYHRRKAQ QMTQKYEEEL TLTRENSIRR

LHSHHTDPRS QPEESVGLRA EGHPDSLKDN SSCSVMSEEP

EGRSYSTLTT VREIETQTEL LSPGSGRAEE EEDQDEGIKQ

AMNHFVQENG TLRAKPTGNG IYINGRGHLV.
```

SEQ ID NO: 1 corresponds to UniProt KB identifier Q96NY8-1, the disclosure of which is incorporated herein by reference.

Certain aspects of the present disclosure provide anti-Nectin-4 antibodies that bind to a human Nectin-4, or a homolog thereof, including without limitation a mammalian Nectin-4 protein and Nectin-4 orthologs from other species, e.g. non-human primates, *Macaca fascicularis*.

The term "HER2" (also known as HER2/neu and ErbB-2) stands for "Human Epidermal growth factor Receptor 2". It includes variants and isoforms of HER2.

The term "tumor antigen", used interchangeably with "cancer antigen", refers to an antigen that is differentially expressed by cancer cells, or to an antigen that is expressed by non-tumoral cells (e.g. immune cells) in tumor or tumor-adjacent tissues that have a pro-tumoral effect (e.g. an immunosuppressive effect), and can thereby be exploited in order to target cancer. Tumor antigens are antigens which can potentially stimulate apparently tumor-specific immune responses. Some of these antigens are encoded, although not necessarily expressed, or expressed at lower levels or less frequently, by normal cells. These antigens can be characterized as those which are normally silent (i.e., not expressed) in normal cells, those that are expressed only at certain stages of differentiation and those that are temporally expressed such as embryonic and fetal antigens. Other tumor antigens are encoded by mutant cellular genes, such as oncogenes (e.g., activated ras oncogene), suppressor genes (e.g., mutant p53), fusion proteins resulting from internal deletions or chromosomal translocations. Still other tumor antigens can be encoded by viral genes such as those carried on RNA and DNA tumor viruses. Still other tumor antigens can be expressed on immune cells capable of contributing to or mediating a pro-tumoral effect, e.g. cell that contributes to immune evasion, a monocyte or a macrophage, optionally a suppressor T cell, regulatory T cell, or myeloid-derived suppressor cell. Tumor antigens are often normal cell surface antigens which are either over-expressed or expressed at abnormal times, or are expressed by a targeted population of cells. Ideally the target antigen is expressed only on proliferative cells (e.g., tumor cells) or pro-tumoral cells present in tumor or tumor-adjacent tissues (e.g. immune cells having an immunosuppressive effect), however this is rarely observed in practice. As a result, target antigens are in many cases selected on the basis of differential expression between proliferative/disease tissue and healthy tissue. Example of tumor antigens include: Nectin-4, Receptor Tyrosine Kinase-like Orphan Receptor 1 (ROR1), Crypto, CD4, CD20, CD30, CD19, CD38, CD47, Glycoprotein NMB, CanAg, a Siglec family member, for example CD22 (Siglec2) or CD33 (Siglec3), CD79, CD123, CD138, CD171, PSCA, L1-CAM, PSMA (prostate specific membrane antigen), BCMA, CD52, CD56, CD80, CD70, E-selectin, EphB2, Melanotransferrin, Mud 6 and TMEFF2. Examples of tumor antigens also include Immunoglobulin superfamily (IgSF) such as cytokine receptors, Killer-Ig Like Receptor, CD28 family proteins, for example, Killer-Ig Like Receptor 3DL2 (KIR3DL2), B7-H3, B7-H4, B7-H6, PD-L1, IL-6 receptor. Examples also include MAGE, MART-1/Melan-A, gp100, major histocompatibility complex class I-related chain A and B polypeptides (MICA and MICB), or optionally an antigen other than MICA and/or MICB, adenosine deaminase-binding protein (ADAbp), cyclophilin b, colorectal associated antigen (CRC)-0017-1A/GA733, protein tyrosine kinase 7(PTK7), receptor protein tyrosine kinase 3 (TYRO-3), nectins (e.g. nectin-4), proteins of the UL16-binding protein (ULBP) family, proteins of the retinoic acid early transcript-1 (RAET1) family, prostate specific antigen (PSA), B-cell maturation antigen (BCMA), anti-Müllerian hormone Type II receptor, delta-like ligand 4 (DLL4), DR5, ROR1 (also known as Receptor Tyrosine Kinase-Like Orphan Receptor 1 or NTRKR1 (EC 2.7.10.1), TROP2, BAGE, RAGE, LAGE-1, NAG, GnT-V, MUM-1, CDK4, MUC family, VEGF, VEGF receptors, Angiopoietin-2, PDGF, TGF-alpha, EGF, EGF receptor, members of the human EGF-like receptor family, e.g., HER-2, HER-3, HER-4 or a heterodimeric receptor comprised of at least one HER subunit, gastrin releasing peptide receptor antigen, Muc-1, CA125, integrin receptors, αvβ3 integrins, α5β1 integrins, αIIbβ3-integrins, PDGF beta receptor, SVE-cadherin, IL-8 receptor, hCG, IL-6 receptor, CSF1R (tumor-associated monocytes and macrophages), α-fetoprotein, E-cadherin, α-catenin, β-catenin, p120ctn, PRAME, NY-ESO-1, gp75, GM2 and GD2 gangliosides, although this is not intended to be exhaustive. In one aspect, the antigen of interest is an antigen (e.g. any one of the antigens listed above) capable of undergoing intracellular internalization, for example when bound by a human antibody.

The term "immunoconjugate" refers to an antigen binding agent (e.g., an antibody binding polypeptide or an antibody) that is conjugated to another molecule (e.g., a camptothecin analogue, an exatecan molecule, a SN-38 molecule). When an immunoconjugate comprises an antibody conjugated to a therapeutic agent (e.g., a camptothecin analogue, an exatecan molecule, a SN-38 molecule), the immunoconjugate can also be referred to as an "antibody drug conjugate" or an "ADC".

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it such as a preventive early asymptomatic intervention; (b) inhibiting the disease, e.g., arresting its development; or relieving the disease, e.g., causing regression of the disease and/or its symptoms or conditions such as improvement or remediation of damage, for example in a subject who has been diagnosed as having the disease. Optionally, treatment may cause (e.g. may be characterized as a method of causing) a decrease in tumor burden, a decrease in the size and/or number of lesions, a decrease or delay in the progression of cancer (e.g., an increase in progression-free survival), a delay or prevention of cancer metastasis and/or an increase in survival. Optionally, treatment may cause or provide (e.g. may be characterized as a method of causing or providing) stable disease, a partial response or a complete response in a subject, e.g. according to standard criteria, optionally RECIST criteria.

Whenever "treatment of cancer" or the like is mentioned with reference to a Nectin-4 binding agent (e.g. antibody or antibody fragment), are comprised:

(a) a method of treatment of cancer, said method comprising the step of administering (for at least one treatment) a Nectin-4 binding agent to an individual, a mammal, especially a human, in need of such treatment, in a dose that allows for the treatment of cancer, (a therapeutically effective amount), optionally in a dose (amount) as specified herein;

(b) the use of a Nectin-4 binding agent for the treatment of cancer;

(c) the Nectin-4 binding agent, for use in the treatment of cancer (especially in a human);

(d) the use of a Nectin-4 binding agent for the manufacture of a pharmaceutical preparation for the treatment of cancer;

(e) a method of using a Nectin-4 binding agent for the manufacture of a pharmaceutical preparation for the treatment of cancer, comprising admixing a Nectin-4 binding agent with a pharmaceutically acceptable carrier;

(f) a pharmaceutical preparation comprising an effective dose of a Nectin-4 binding agent that is appropriate for the treatment of cancer;

(g) any combination of (a), (b), (c), (d), (e) and (f), in accordance with the subject matter allowable for patenting in a country where this application is filed.

The term "biopsy" as used herein is defined as removal of a tissue for the purpose of examination, such as to establish diagnosis. Examples of types of biopsies include by application of suction, such as through a needle attached to a syringe; by instrumental removal of a fragment of tissue; by removal with appropriate instruments through an endoscope; by surgical excision, such as of the whole lesion; and the like.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon,"

"gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" includes full-length antibodies as well as any fragment or derivative of any of the herein described antibodies.

The amino acid residues of an antibody that are responsible for antigen binding can also be referred to hypervariable region. The hypervariable region generally comprises amino acid residues from a "complementarity-determining region" or "CDR" (e.g., residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g., residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917), or a similar system for determining essential amino acids responsible for antigen binding. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "specifically binds to" means that an antibody can bind preferably in a competitive binding assay to the binding partner, e.g. Nectin-4, as assessed using either recombinant forms of the proteins, epitopes therein, or native proteins present on the surface of isolated target cells. Competitive binding assays and other methods for determining specific binding are well-known in the art. For example, binding can be detected via radiolabels, physical methods such as mass spectrometry, or direct or indirect fluorescent labels detected using, e.g., cytofluorometric analysis (e.g. FACScan). Binding above the amount seen with a control, non-specific agent indicates that the agent binds to the target.

When an antibody is said to "compete with" a particular monoclonal antibody, it means that the antibody competes with the monoclonal antibody in a binding assay using either recombinant molecules (e.g., Nectin-4) or surface expressed molecules (e.g., Nectin-4). For example, if a test antibody reduces the binding of an antibody having a heavy chain variable region of any of SEQ ID NOS: 3, 7, or 9 and a respective light chain variable region of SEQ ID NO: 4, 8 or 10 to a Nectin-4 polypeptide or Nectin-4-expressing cell in a binding assay, the antibody is said to "compete" respectively with such antibody.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of monoclonal antibodies can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of monoclonal antibodies is the use of surface plasmon resonance (SPR) screening (such as by analysis with a BIAcore™ SPR analytical device).

Within the context herein a "determinant" designates a site of interaction or binding on a polypeptide.

The term "epitope" refers to an antigenic determinant and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "agent" is used herein to denote a chemical compound, a mixture of chemical compounds, a biological macromolecule, or an extract made from biological materials. The term "therapeutic agent" refers to an agent that has biological activity.

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, MD).

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

As used herein, "alkyl" refers to a straight or branched hydrocarbon chain that comprises a fully saturated (no double or triple bonds) hydrocarbon group. The alkyl group may have, for example, 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, the term "heteroalkyl" refers to a straight or branched alkyl group that contains one or more heteroatoms, that is, an element other than carbon (including but not limited to oxygen, sulfur, nitrogen, phosphorus) in place of one or more carbon atoms.

Whenever a group is described as being "substituted" that group substituted with one or more of the indicated substituents. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, heteroalkyl, aryl, heteroaryl, heteroalicyclyl, aralkyl, heteroaralkyl, (heteroalicyclyl)alkyl, hydroxy, alkoxy, aryloxy, acyl, mercapto, alkylthio, arylthio, cyano, halogen, thiocarbonyl, carbamyl, thiocarbamyl, amido, sulfonamido, sulfonamido, carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, and protected derivatives thereof.

Where the number of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

Reference to a "Compound" or "Formula" having a particular number (e.g. "Compound 1", "Compound 2", "Formula I" or "Formula II"), unless the context clearly indicates otherwise, designates all compounds derived from the Compound or Formula having the particular number. Compound 1, for example includes reference to Compound 1a and 1b.

Nectin-4 Binding Agents

Nectin-4 binding domains used to prepare the Nectin-4 binding ADC compositions of the disclosure can be readily derived from any of a variety of immunoglobulin or non-immunoglobulin scaffolds, for example affibodies based on the Z-domain of staphylococcal protein A, engineered Kunitz domains, monobodies or adnectins based on the 10th extracellular domain of human fibronectin III, anticalins derived from lipocalins, DARPins (designed ankyrin repeat domains, multimerized LDLR-A module, avimers or cysteine-rich knottin peptides. The hypervariable regions, heavy and light chain CDRs, heavy and light chain variable regions, and antibodies, e.g., full-length antibodies or antibody fragments, that comprise them, will bind human Nectin-4 expressed on the surface of a cell, e.g., a tumor cell. When used in therapy for the elimination of Nectin-4-expressing tumor cells, the Nectin-4 binding agent will be capable of causing the death of Nectin-4-expressing tumor cells when conjugated to a cytotoxic molecule as disclosed herein, e.g. as determined in an assay in which the Nectin-4 binding ADC is brought into contact with the tumor cells, in the absence of immune effector and/or cells other than the tumor cells.

In one embodiment, an anti-Nectin-4 antigen binding protein or antibody binds to the mature Nectin-4 polypeptide, e.g. a polypeptide having the amino acid sequence of residue 32-510 of SEQ ID NO: 1.

In one embodiment, an anti-Nectin-4 antigen binding protein or antibody binds to the Ig-like V type domain of a Nectin-4 polypeptide. For example, the antigen binding protein or antibody can be characterized as being capable of binding to (or binds an epitope within or at least partly within) the domain of Nectin-4 having the amino acid sequence of residues 32-144 of SEQ ID NO: 1, also shown as SEQ ID NO: 2, below.

(SEQ ID NO: 2)

GELETSDVVTVVLGQDAKLPCFYRGDSGEQVGQVAWARVDAGEG

AQELALLHSKYGLHVSPAYEGRVEQPPPPRNPLDGSVLLRNAVQ

ADEGEYECRVSTFPAGSFQARLRLR

In one embodiment, an antigen binding protein or antibody comprises the hypervariable region (e.g. the heavy and light chain CDR1, 2 and 3, according to Kabat numbering) of any known anti-Nectin-4 antibody. In one embodiment, an antigen binding protein or antibody competes for binding to the Nectin-4 polypeptide with any one or more known anti-Nectin-4 antibodies such as antibodies ASG-22ME, 14A5.2 or N41. In one embodiment, an antigen binding protein or antibody recognizes, binds to, or has immunospecificity for substantially or essentially the same, or the same, epitope or "epitopic site" on a Nectin-4 polypeptide as antibody any of antibodies ASG-22ME, 14A5.2 or N41.

In some embodiments, anti-Nectin-4 antibody can be selected to exhibit significantly lower binding for a mutant human Nectin-4 polypeptide in which 1, 2, 3, 4 or more residues within the binding site or epitope on Nectin-4 of any of antibodies ASG-22ME, 14A5.2 or N41 are substituted with a different amino acid, compared to a wild-type Nectin-4 polypeptide.

In some embodiments, anti-Nectin-4 antibody can be characterized as lacking binding or exhibiting significantly lower binding for a mutant human Nectin-4 polypeptide lacking the Ig-like V type domain (e.g. the domain has been deleted), compared to a wild-type Nectin-4 polypeptide. In some embodiments, anti-Nectin-4 antibody can be selected to exhibit significantly lower binding for a mutant human Nectin-4 polypeptide in which 1, 2, 3, 4 or more residues within the Ig-like V type domain are substituted with a different amino acid, compared to a wild-type Nectin-4 polypeptide.

In some embodiments, anti-Nectin-4 antibody can be selected or characterized as exhibiting significantly lower binding for a mutant human Nectin-4 polypeptide in which the Ig-like V type domain (or a portion thereof) is absent or is substituted with an amino acid sequence from a different polypeptide or different domain (e.g. a non-human or non-primate Nectin-4 polypeptide, a non-Nectin-4 polypeptide, a non-Ig-like V type domain), compared to a wild-type Nectin-4 polypeptide.

Binding of anti-Nectin-4 antibody to cells transfected with the Nectin-4 mutants can be measured and compared to the ability of anti-Nectin-4 agent to bind wild-type Nectin-4 polypeptide (e.g., SEQ ID NO: 1). A reduction in binding between an anti-Nectin-4 agent and a mutant Nectin-4 polypeptide means that there is a reduction in binding affinity (e.g., as measured by known methods such FACS testing of cells expressing a particular mutant, or by Biacore testing of binding to mutant polypeptides) and/or a reduction in the total binding capacity of the anti-Nectin-4 agent (e.g., as evidenced by a decrease in Bmax in a plot of anti-Nectin-4 agent concentration versus polypeptide concentration). A significant reduction in binding indicates that the mutated residue is directly involved in binding to the anti-Nectin-4 agent or is in close proximity to the binding protein when the anti-Nectin-4 agent is bound to Nectin-4.

In some embodiments, a significant reduction in binding means that the binding affinity and/or capacity between an anti-Nectin-4 antibody and a mutant Nectin-4 polypeptide is reduced by greater than 40%, greater than 50%, greater than 55%, greater than 60%, greater than 65%, greater than 70%, greater than 75%, greater than 80%, greater than 85%, greater than 90% or greater than 95% relative to binding between the antibody and a wild type Nectin-4 polypeptide. In certain embodiments, binding is reduced below detectable limits. In some embodiments, a significant reduction in binding is evidenced when binding of an anti-Nectin-4 antibody to a mutant Nectin-4 polypeptide is less than 50% (e.g., less than 45%, 40%, 35%, 30%, 25%, 20%, 15% or 10%) of the binding observed between the anti-Nectin-4 antibody and a wild-type Nectin-4 polypeptide.

In some embodiments, an anti-Nectin-4 antibody exhibits significantly lower binding for (e.g. displays a loss of binding to) a mutant Nectin-4 polypeptide in which a residue in a segment corresponding to residues 32-144 (or a subsequence thereof, optionally a subsequence of at least 4, 5, 6, 10, 20 or 40 residues) in a wild-type Nectin-4 polypeptide (e.g., comprising a sequence of SEQ ID NO: 1) is lacking (e.g., is deleted or substituted with a different amino acid).

Antibodies may be produced by a variety of techniques known in the art. Typically, they are produced by immunization of a non-human animal, preferably a mouse, with an immunogen comprising a Nectin-4 polypeptide, preferably a human Nectin-4 polypeptide. The Nectin-4 polypeptide may comprise the full length sequence of a human Nectin-4 polypeptide, or a fragment or derivative thereof, typically an immunogenic fragment, i.e., a portion of the polypeptide comprising an epitope exposed on the surface of cells expressing a Nectin-4 polypeptide, for example the epitope recognized by the ASG-22ME, 14A5.2 or N41 antibody. Such fragments typically contain at least about 7 consecutive amino acids of the mature polypeptide sequence, even more preferably at least about 10 consecutive amino acids thereof. Fragments typically are essentially derived from the extra-cellular domain of the receptor. In one embodiment, the immunogen comprises a wild-type human Nectin-4 polypeptide in a lipid membrane, typically at the surface of a cell. In a specific embodiment, the immunogen comprises intact cells, particularly intact human cells, optionally treated or lysed. In another preferred embodiment, the polypeptide is a recombinant Nectin-4 polypeptide. In a specific embodiment, the immunogen comprises intact Nectin-4-expressing cells.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, NY (1988), the entire disclosure of which is herein incorporated by reference).

Antibodies may also be produced by selection of combinatorial libraries of immunoglobulins, as disclosed for instance in (Ward et al. Nature, 341 (1989) p. 544, the entire disclosure of which is herein incorporated by reference).

The identification of one or more antibodies that compete for binding to Nectin-4, with monoclonal antibody ASG-22ME, 14A5.2 or N41 can be readily determined using any one of a variety of immunological screening assays in which antibody competition can be assessed. Many such assays are routinely practiced and are well known in the art (see, e.g., U.S. Pat. No. 5,660,827, which is incorporated herein by reference).

For example, where the test antibodies to be examined are obtained from different source animals, or are even of a different Ig isotype, a simple competition assay may be employed in which the control (ASG-22ME, 14A5.2 or N41, for example) and test antibodies are admixed (or pre-adsorbed) and applied to a sample containing Nectin-4 polypeptides. Protocols based upon western blotting and the use of Surface Plasmon Resonance (e.g. Biacore™) analysis are suitable for use in such competition studies.

In certain embodiments, one pre-mixes the control antibodies (ASG-22ME, 14A5.2 or N41, for example) with varying amounts of the test antibodies (e.g., about 1:10 or about 1:100) for a period of time prior to applying to the Nectin-4 antigen sample. In other embodiments, the control and varying amounts of test antibodies can simply be admixed during exposure to the Nectin-4 antigen sample. As long as one can distinguish bound from free antibodies (e.g., by using separation or washing techniques to eliminate unbound antibodies) and ASG-22ME, 14A5.2 or N41 from the test antibodies (e.g., by using species-specific or isotype-specific secondary antibodies or by specifically labeling ASG-22ME, 14A5.2 or N41 with a detectable label) one can determine if the test antibodies reduce the binding of ASG-22ME, 14A5.2 or N41 to the antigens. The binding of the (labeled) control antibodies in the absence of a completely irrelevant antibody can serve as the control high value. The control low value can be obtained by incubating the labeled (ASG-22ME, 14A5.2 or N41) antibodies with unlabelled antibodies of exactly the same type (ASG-22ME, 14A5.2 or N41), where competition would occur and reduce binding of the labeled antibodies. A test antibody may for example reduce the binding of ASG-22ME, 14A5.2 or N41 to Nectin-4 antigens by at least about 50%, such as at least about 60%, or more preferably at least about 80% or 90% (e.g., about 65-100%), at any ratio of ASG-22ME, 14A5.2 or N41:test antibody between about 1:10 and about 1:100. Optionally, such test antibody will reduce the binding of ASG-22ME, 14A5.2 or N41 to the Nectin-4 antigen by at least about 90% (e.g., about 95%).

Competition can also be assessed by, for example, a flow cytometry test. In such a test, cells bearing a given Nectin-4 polypeptide can be incubated first with ASG-22ME, 14A5.2 or N41, for example, and then with the test antibody labeled with a fluorochrome or biotin. The antibody is said to compete with ASG-22ME, 14A5.2 or N41 if the binding obtained upon preincubation with a saturating amount of ASG-22ME, 14A5.2 or N41 is about 80%, preferably about 50%, about 40% or less (e.g., about 30%, 20% or 10%) of the binding (as measured by mean of fluorescence) obtained by the antibody without preincubation with ASG-22ME, 14A5.2 or N41. Alternatively, an antibody is said to compete with ASG-22ME, 14A5.2 or N41 if the binding obtained with a labeled ASG-22ME, 14A5.2 or N41 antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a Nectin-4 antigen is immobilized may also be employed. The surface in the simple competition assay is preferably a Biacore™ chip (or other media suitable for surface plasmon resonance analysis). The control antibody (e.g., ASG-22ME, 14A5.2 or N41) is then brought into contact with the surface at a Nectin-4-saturating concentration and the Nectin-4 and surface binding of the control antibody is measured. This binding of the control antibody is compared with the binding of the control antibody to the Nectin-4-containing surface in the absence of test antibody. In a test assay, a significant reduction in binding of the Nectin-4-containing surface by the control antibody in the presence of a test antibody indicates that the test antibody recognizes substantially the same region on Nectin-4 as the control antibody such that the test antibody "cross-reacts" with the control antibody. A test antibody may for example reduce the binding of control (such as ASG-22ME, 14A5.2 or N41) antibody to a Nectin-4 antigen by at least about 30% or more, preferably about 40%. Optionally, such a test antibody will reduce the binding of the control antibody (e.g., ASG-22ME, 14A5.2 or N41) to the Nectin-4 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the Nectin-4 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

The antibodies will bind to Nectin-4-expressing tumor cells from an individual or individuals with a cancer characterized by Nectin-4-positive tumor cells, i.e., an individual that is a candidate for treatment with one of the herein-described methods using an anti-Nectin-4 antibody. Accordingly, once an antibody that specifically recognizes Nectin-4 on cells is obtained, it can optionally be tested for its ability to bind to Nectin-4-positive cells (e.g., cancer cells). It can optionally be tested for its ability to bind to tumor cells that express at their surface high and/or o tumor cells that express at their surface low levels of Nectin-4 polypeptides. In particular, prior to treating a patient with one of the present antibodies, one may optionally test the ability of the antibody to bind malignant cells taken from the patient, e.g., in a blood sample or tumor biopsy, to maximize the likelihood that the therapy will be beneficial in the patient.

In one embodiment, the antibodies are validated in an immunoassay to test their ability to bind to Nectin-4-expressing cells, e.g., malignant cells. For example, a blood sample or tumor biopsy is performed and tumor cells are collected. The ability of a given antibody to bind to the cells is then assessed using standard methods well known to those in the art. To assess the binding of the antibodies to the cells, the antibodies can either be directly or indirectly labeled. When indirectly labeled, a secondary, labeled antibody is typically added.

Determination of whether an antibody binds within an epitope region can be carried out in ways known to the person skilled in the art. As one example of such mapping/characterization methods, an epitope region for an anti-Nectin-4 antibody may be determined by epitope "footprinting" using chemical modification of the exposed amines/carboxyls in the Nectin-4 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g., by using trypsin in a ratio of about 1:50 to Nectin-4 or o/n digestion at and pH 7-8, followed by mass spectrometry (MS) analysis for peptide identification. The peptides protected from trypsin cleavage by the anti-Nectin-4 binder can subsequently be identified by comparison of samples subjected to trypsin digestion and samples incubated with antibody and then subjected to digestion by e.g., trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the Nectin-4 polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence over-all fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE™) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody can be identified in one or more of the exemplary competition assays described herein.

Upon immunization and production of antibodies in a vertebrate or cell, or upon generation of a library of candidate antibodies or amino acid sequences (e.g., by phage display techniques), particular selection steps may be performed to isolate antibodies or non-antibody peptide or protein scaffolds. In this regard, in a specific embodiment, provided are methods of producing such antibodies, comprising: (a) immunizing a non-human mammal with an immunogen comprising a Nectin-4 polypeptide or preparing a library of antibodies or polypeptide sequences; and (b) preparing antibodies from said immunized animal, or from said library of antibodies or sequences; and (c) selecting antibodies from step (b) that are capable of binding Nectin-4, optionally selecting antibodies from step (b) that are capable of binding to the mg-like V set domain of Nectin-4.

In one aspect an antibody can have an average disassociation constant ($K_D$) of no more than $1\times10^{-8}$ M, optionally less than $1\times10^{-9}$ M with respect to human Nectin-4, as determined by, e.g., surface plasmon resonance (SPR) screening (such as by analysis with a BIAcore™ SPR analytical device). In a more particular exemplary aspect, provided are anti-Nectin-4 antibodies that have a KD of about $1\times10^{-8}$ M to about $1\times10^{-10}$ M, or about $1\times10^{-9}$ M to about $1\times10^{-11}$ M, for Nectin-4.

In one aspect of any of the embodiments, the antibodies prepared according to the present methods are monoclonal antibodies. In another aspect, the non-human animal used to produce antibodies is a mammal, such as a rodent, bovine, porcine, fowl, horse, rabbit, goat, or sheep. Antibodies of the invention can optionally be specified to be antibodies other than any of antibodies ASG-22ME, 14A5.2 or N41, or derivatives thereof, e.g., that comprise their respective heavy and light chain CDRs or the antigen binding region in whole or in part.

DNA encoding an antibody that binds an epitope present on Nectin-4 polypeptides is isolated from a hybridoma and placed into an expression vector(s), which is then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. In one embodiment, provided is an isolated nucleic acid sequence encoding a light chain and/or a heavy chain of an antibody, as well as a recombinant host cell comprising (e.g., in its genome) such nucleic acid.

In any embodiment, the anti-Nectin-4 binding protein (e.g. antibody or antibody fragment) can be assessed for its ability to induce intracellular internalization of Nectin-4 expressed by a tumor cell. For example, the Fab-Zap assay described in the Examples herein can be used as a convenient method of assessing internalization in Nectin-4 expressing cells (e.g. tumor cells). In any embodiment herein, the anti-Nectin-4 binding protein, antibody or antibody fragment, or the antibody-drug conjugate comprising such antibody or fragment, is characterized as being capable, upon binding to Nectin-4 on the surface of a tumor cell, of undergoing intracellular internalization.

In one aspect, the anti-Nectin-4 antibody is an antibody that is a function-conservative variant of any of the exemplary antibodies described herein, for example a function-conservative variant of the antibody (ASG-22ME) having a heavy chain variable region of SEQ ID NO: 3 and a light chain variable region of SEQ ID NO: 4, a function-conservative variant of the antibody (14A5.2) having a heavy chain variable region of SEQ ID NO: 7 and a light chain variable region of SEQ ID NO: 8, or a function-conservative variant of the antibody (N41) having a heavy chain variable region of SEQ ID NO: 9 and a light chain variable region of SEQ ID NO: 10. "Function-conservative variants" are those in which a given amino acid residue in a protein (e.g., an antibody or antibody fragment) has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native, reference or parent protein to which it is compared.

An exemplary anti-Nectin-4 VH and VL pair that can be used to prepare an ADC for use according to the disclosure can be derived from antibody enfortumab (or ASG-22ME) by employing the VH and VL (or the hypervariable region amino acid residues) of ASG-22ME, the antibody component used in enfortumab vedotin, the amino acid sequence of the heavy chain variable region of which is listed below (SEQ ID NO: 3), and the amino acid sequence of the light chain variable region of which is listed below (SEQ ID NO: 4). The CDRs according to Kabat numbering are underlined in SEQ ID NOS: 3 and 4. See also U.S. Pat. No. 8,637,642 and PCT publication No. WO2012/047724, the disclosures of which are incorporated herein by reference. Optionally, the VH and VL comprise (e.g., are modified to incorporate) human acceptor frameworks. In one embodiment, an anti-Nectin-4 antibody for use according to the disclosure comprises the VH CDR1, CDR2 and/or CDR3 (e.g., according to Kabat numbering) of the heavy chain variable region having the amino acid sequence of SEQ ID NO: 3. In one embodiment, an anti-Nectin-4 antibody comprises the VL CDR1, CDR2 and/or CDR3 (e.g., according to Kabat numbering) of the light chain variable region having the amino acid sequence of SEQ ID NO: 4.

ASG-22ME (enfortumab) VH:
(SEQ ID NO: 3)
EVQLVESGGG LVQPGGSLRL SCAASGFTFS SYNMNWVRQA

PGKGLEWVSY ISSSSSTIYY ADSVKGRFTI SRDNAKNSLS

LQMNSLRDED TAVYYCARAY YYGMDVWGQG TTVTVSS.

ASG-22ME (enfortumab) VL:
(SEQ ID NO: 4)
DIQMTQSPSS VSASVGDRVT ITCRASQGIS GWLAWYQQKP

GKAPKFLIYA ASTLQSGVPS RFSGSGSGTD FTLTISSLQP

EDFATYYCQQ ANSFPPTFGG GTKVEIKRTV A .

The full heavy and light chains of enfortumab or ASG-22CE/ASG-22ME are shown in SEQ ID NOS: 5 and 6. In one embodiment, an anti-Nectin-4 antibody comprises a heavy chain having an amino acid sequence shown in SEQ ID NO: 5 and a light chain having an amino acid sequence shown in SEQ ID NO: 6.

ASG-22CE/ASG-22ME (enfortumab) full heavy chain:
(SEQ ID NO: 5)
EVQLVESGGG LVQPGGSLRL SCAASGFTFS SYNMNWVRQA

PGKGLEWVSY ISSSSSTIYY ADSVKGRFTI SRDNAKNSLS

LQMNSLRDED TAVYYGARAY YYGMDVWGQG TTVTVSSAST

KGPSVFPLAP SSKSTSGGTA ALGCLVKDYF PEPVTVSWNS

GALTSGVHTF PAVLQSSGLY SLSSVVTVPS SSLGTQTYIC

NVNHKPSNTK VDKRVEPKSC DKTHTCPPCP APELLGGPSV

FLFPPKPKDT LMISRTPEVT CVVVDVSHED PEVKFNWYVD

-continued

```
GVEVHNAKTK PREEQYNSTY RVVSVLTVLH QDWLNGKEYK

CKVSNKALPA PIEKTISKAK GQPREPQVYT LPPSREEMTK

NQVSLTCLVK GFYPSDIAVE WESNGQPENN YKTTPPVLDS

DGSFFLYSKL TVDKSRWQQG NVFSCSVMHE ALHNHYTQKS

LSLSPGK.
```

ASG-22CE/ASG-22ME (enfortumab) full light chain: (SEQ ID NO: 6)

```
DIQMTQSPSS VSASVGDRVT ITCRASQGIS GWLAWYQQKP

GKAPKFLIYA ASTLQSGVPS RFSGSGSGTD FTLTISSLQP

EDFATYYCQQ ANSFPPTFGG GTKVEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC.
```

Another exemplary anti-Nectin-4 VH and VL pair that can be used to prepare an ADC for use according to the disclosure can be derived from antibody 14A5.2, the amino acid sequence of the heavy chain variable region of which is listed below (SEQ ID NO: 7), and the amino acid sequence of the light chain variable region of which is listed below (SEQ ID NO: 8). The CDRs according to Kabat numbering are underlined in SEQ ID NOS: 7 and 8. The antibody sequences are also disclosed in PCT publication No. WO2018/158398, the disclosure of which is incorporated herein by reference. Optionally, the VH and VL comprise (e.g., are modified to incorporate) human acceptor frameworks. In one embodiment, an anti-Nectin-4 antibody for use according to the disclosure comprises the VH CDR1, CDR2 and/or CDR3 (e.g., according to Kabat numbering) of the heavy chain variable region having the amino acid sequence of SEQ ID NO: 7. In one embodiment, an anti-Nectin-4 antibody comprises the VL CDR1, CDR2 and/or CDR3 (e.g., according to Kabat numbering) of the light chain variable region having the amino acid sequence of SEQ ID NO: 8.

14A5.2 VH: (SEQ ID NO: 7)

```
EVLLQQSGPELVKPGASVKIPCKASGYTFTDYTMDWVKQSHGKS

LEWIGDINPNNDVTMYNEKFKGRATLTVDKSSSTAYMEVRSLTS

EDTAVYYCVRGRGFAYWGQGTLVTVSA.
```

14A5.2 VL: (SEQ ID NO: 8)

```
DIVLTQSPASLIVSLGQRATISCRASQSVSTSSNSYMHWYQQKP

GQPPKLLIRFASNLESGVPARFSGSGSGTYFTLNIHPVEEEDSA

TYYCQHSWEIPYTFGGGTKLEIK.
```

Another exemplary anti-Nectin-4 VH and VL pair that can be used to prepare an ADC for use according to the disclosure can be obtained from antibody N41 the amino acid sequence of the heavy chain variable region of which is listed below (SEQ ID NO: 9), and the amino acid sequence of the light chain variable region of which is listed below (SEQ ID NO: 10). The CDRs according to Kabat numbering are underlined in SEQ ID NOS: 9 and 10. The antibody VH, VL and respective CDR sequences are also disclosed in PCT publication No. WO2017/042210, the disclosure of which is incorporated herein by reference. Optionally, the VH and VL comprise (e.g., are modified to incorporate) human acceptor frameworks. In one embodiment, an anti-Nectin-4 antibody for use according to the disclosure comprises the VH CDR1, CDR2 and/or CDR3 (e.g., according to Kabat numbering) of the heavy chain variable region having the amino acid sequence of SEQ ID NO: 9. In one embodiment, an anti-Nectin-4 antibody comprises the VL CDR1, CDR2 and/or CDR3 (e.g., according to Kabat numbering) of the light chain variable region having the amino acid sequence of SEQ ID NO: 10.

N41 VH: (SEQ ID NO: 9)

```
QVQLKQSGPGLVQPSQSLSITCTVSGFSLTNYGVHWVRQSPGKG

LEWLGVIWSGGSTDYNAAFISRLSISKDTSKSQVFFKMNSLQAD

DTAIYYCARELIHAMDNWGQGTSVTVSS.
```

N41 VL: (SEQ ID NO: 10)

```
DIQMTQSPASLSVSVGETVTITCRASENIYSNLAWYQQKQGNSP

QLLVFAATNLADGVPSRFSGSGSGTQYSLKINSLQSEDFGTYYC

QHFWGTPTFGGGTKLEIK.
```

Fragments and derivatives of antibodies (which are encompassed by the term "antibody" or "antibodies" as used in this application, unless otherwise stated or clearly contradicted by context), can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain molecule and (3) single chain polypeptides containing only one heavy chain variable region, or a fragment thereof containing the three CDRs of the heavy chain variable region, without an associated light chain molecule; and multispecific antibodies formed from antibody fragments. Included, inter alia, are a nanobody, domain antibody, single domain antibody or a "dAb".

In one embodiment, the antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for Nectin-4 and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding. In a one example, the FRs of a humanized antibody chain are derived from a human variable region having at least about 60% overall sequence identity, and preferably at least about 70%, 75% or 80% overall sequence identity, with the variable region of the nonhuman donor (e.g., an ASG-22ME, 14A5.2 or N41 antibody). Optionally, the humanized heavy and/or light chain variable region shares at least about 60%, 70% or 80% overall sequence identity with the respective heavy and/or light chain variable region of the nonhuman donor (e.g., an ASG-22ME, 14A5.2 or N41 antibody). Another method of making "humanized" monoclonal antibodies is to use a XenoMouse (Abgenix, Fremont, CA) as the mouse used for immunization. A XenoMouse is a murine host that has had its immunoglobulin genes replaced by functional human immunoglobulin genes. Thus, antibodies produced by this mouse or in hybridomas made from the B cells of this mouse, are already humanized. The XenoMouse is described in U.S. Pat. No. 6,162,963, which is herein incorporated in its entirety by reference. Human antibodies may also be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

Advantageously, camptothecin analogue-containing linkers of the disclosure can be used in processes for preparing a conjugated antigen binding agent (e.g. peptide, polypeptide, antibody or antibody fragment), so as to obtain an antigen binding agent-drug conjugate, e.g. an antibody drug conjugate (ADC). In one embodiment, a process for preparing an antigen binding agent-conjugate comprises conjugating a camptothecin analogue (Z) to an antigen binding agent. In one embodiment, camptothecin analogue (Z) can be specified as being conjugated to the antigen binding agent via a linker (X). X is a linker which connects the antigen binding agent such an antibody (Ab) and camptothecin analogue (Z), e.g., upon conjugation X is the residue of a linker following covalent linkage to one or both of Ab and Z.

In embodiments herein, a process for preparing the antibody-drug conjugates comprises a step of contacting and/or reacting an antigen binding agent such as antibody (Ab) with a camptothecin analogue (Z). The contacting can be carried out under conditions suitable such that an antigen binding agent drug conjugate of an aspect of the disclosure is formed or obtained. Z may for example be comprised in a compound comprising a camptothecin analogue (Z) and a linker (X) or portion of linker (X), such that the step comprises contacting an antigen binding agent with a compound comprising a camptothecin analogue (Z) and a linker (X) or portion of linker (X). A process can optionally specify a step of isolating or recovering the antigen binding agent drug conjugate that is formed, and, optionally, further processing the composition for use as a medicament, optionally formulating said antigen binding agent conjugate (e.g., with a pharmaceutical excipient) for administration to a human subject.

Optionally, a method of making an ADC comprises conjugating the antibody Ab) to 2, 3, 4, 5, 6, 7 or 8 molecules of camptothecin analogue. Optionally, the composition obtained is characterized by a DAR of between 2 and 4, between 4 and 6, between 6 and 8. Optionally, the method comprises conjugating the antibody to 4 molecules of camptothecin analogue. Optionally, the method further comprises assessing the DAR, and if the DAR corresponds to a pre-determined specification (e.g. a DAR or DAR range as disclosed herein, a DAR of about 2, 4, 6, or 8, etc.), further processing the composition for use as a medicament, optionally formulating said antibody (e.g., with a pharmaceutical excipient) for administration to a human subject.

In some embodiments, the linker (X)—(Z) elements are prepared and isolated prior to contacting (and reacting) the compound comprising (X) and (Z) with the (Ab), thereby forming the drug conjugate.

In some embodiments, the method comprises:

(a) contacting and/or reacting linker (X) or a portion of linker (X) with the (Ab) to form a Ab-X conjugate, and (b) contacting and/or reacting Ab-X of step (a) with a camptothecin analogue (Z) or a compound comprising a second portion of linker (X) and (Z), thereby forming the antibody drug conjugate.

X can for example represent a molecule comprising a moiety that is cleavable, e.g., under physiological conditions, optionally under intracellular conditions. In one embodiment, X represents a molecule comprising (i) a spacer (Y), (ii) a cleavable moiety and (iii) an optional self-eliminating or non-self-eliminating spacer system (Y'). The cleavable moiety can for example be an oligopeptide (e.g. a di-, tri-, tetra- or penta-peptide). The spacer Y can be positioned between the Ab and the cleavable moiety, and the spacer system (Y') can be positioned between the cleavable moiety and Z.

In some embodiments, linker X or spacer Y can optionally be specified as comprising a reactive group (R) capable of reacting (e.g. under suitable conditions, optionally after deprotection) with an amino acid of the antibody or with a complementary reactive group (R') that is attached to an amino acid of the antibody. Optionally, R is a group reactive with a free amino, hydroxyl, sulfhydryl or carboxyl group on the antibody.

In some embodiments, linker X or spacer Y can optionally be specified as comprising the residue of the reaction of reactive group R with an amino acid of the antibody or with a complementary reactive group (R') that is attached to an amino acid of the antibody. Optionally, R is the residue of the reaction of a group reactive with a free amino, hydroxyl, sulfhydryl or carboxyl group on the antibody and said free amino, hydroxyl, sulfhydryl or carboxyl group.

In any embodiment, prior to the step of contacting and/or reacting an antibody or antibody fragment with a compound (e.g. linker and/or camptothecin analogue), the method comprises a step of preparing, selecting or providing an antibody or antibody fragment. In one embodiment, the step comprise preparing, selecting or providing an anti-Nectin-4 antibody or antibody fragment and determining or testing whether the antibody or antibody fragment has feature(s) of an anti-Nectin-4 antibody or antibody fragment disclosed herein.

For example, an anti-Nectin-4 antibody or antibody fragment can be tested for the ability to bind to Nectin-4, or to the V domain of Nectin-4. An antibody or antibody fragment that is determined to bind to Nectin-4 (or to the V domain) is then contacted and/or reacted with the compound (e.g. linker (X) and/or camptothecin analogue (Z)). For example, an anti-Nectin-4 antibody or antibody fragment can be tested for the ability to bind to a mutant Nectin-4 polypeptide (e.g. a mutant Nectin-4 polypeptide lacking the Ig-like V set domain). An antibody or antibody fragment that is determined to have decreased or loss of binding to the mutant Nectin-4 polypeptide (e.g. compared to binding a wild-type Nectin-4 polypeptide) is then contacted and/or reacted with the compound (e.g. linker (X) and/or camptothecin analogue (Z)).

As further described herein, some well-known methods for conjugating cytotoxic agents to antibodies involve multiple reactions steps in which an antibody is first modified with a linker or part of a linker, followed by a reaction in which the cytotoxic agent is conjugated to the antibody-linker composition.

In one embodiment, provided is a process for preparing antigen binding agent-drug conjugate, comprising:

(i) contacting an antigen binding agent (e.g. peptide, polypeptide, antibody or antibody fragment (e.g. that binds Nectin-4) with a compound (L) comprising (a) a first reactive group capable of reacting with an amino acid (e.g., a side chain or glycan of the amino acid, or a group attached to an amino acid or glycan of the amino acid) of the agent and (b) a second reactive group (R'), to obtain a modified agent comprising one or more amino acids functionalized with the compound (L); and (ii) reacting the modified agent of step (i) with a compound comprising (a) a reactive group (R) that is complementary to reactive group (R'), (b) an amino acid unit (e.g. a di-, tri-, tetra- or penta-peptide) that is cleaved by an intracellular peptidase or protease enzyme, (c) optionally a non-self immolative or a self immolative spacer (Y'), and (d) a cytotoxic agent (Z). Optionally, the compound of step (ii) further comprises a spacer (Y) placed between R and the amino acid unit.

In one embodiment, R and R' are capable of undergoing a click reaction or a cycloaddition, optionally wherein R comprises or is an alkyne moiety and R' comprises or is an azide moiety, or wherein R' comprises or is an alkyne moiety and R comprises or is an azide moiety, and wherein the reaction of step (ii) is a 1,3-dipolar cycloaddition.

In one embodiment, the reaction of step (i) is carried out in presence of a catalyst, optionally the catalyst is an enzyme (e.g., a transglutaminase).

In one embodiment, prior to contacting an anti-Nectin-4 antibody or antibody fragment with a compound (L), step (i) comprises a step of modifying the anti-Nectin-4 antibody or antibody fragment. For example, the antibody or antibody fragment can be modified by reacting or contacting it with an enzyme capable of modifying antibody glycosylation (e.g., at Kabat residue N297). In one example, the modification comprises the deglycosylation of an antibody glycan having a core N-acetylglucosamine, in the presence of an endoglycosidase, in order to obtain an antibody comprising a core N-acetylglucosamine substituent, wherein said core N-acetylglucosamine and said core N-acetylglucosamine substituent are optionally fucosylated. Examples of endoglycosidases include EndoS, EndoA, EndoE, EfEndo18A, EndoF, EndoM, EndoD, EndoH, EndoT and EndoSH and/or a combination thereof.

The antigen binding protein (e.g. antibody) molecule and camptothecin analogue molecule are connected by means of a linker. In such embodiments, the immunoconjugate can for example be represented by Formula (II):

$$Ab\text{-}(X\text{—}(Z)_n)_m \qquad \text{Formula (II)}$$

wherein,

Ab is an anti-Nectin4 antigen binding protein (e.g. an antibody);

X is a linker which connects Ab and Z, e.g., the residue of a linker following covalent linkage to one or both of Ab and Z;

Z a camptothecin analogue, optionally Z comprises a structure of Compounds 1 or 2 (exatecan or a SN-38 molecule);

n is 1 or 2; and when n is 1, m is from among 1 to 8, or optionally m is an integer selected from among 1 to 8 or 1 to 6, optionally m is an integer selected from among 1 to 4, optionally m is 2 or 4; optionally, m is 2, 3, 4, 5, 6, 7 or 8; and when n is 2, m is from among 1 to 4, or optionally m is an integer selected from among 1 to 4 or 1 to 3, optionally m is an integer selected from among 1 to 4, optionally m is 2 or 4; optionally, m is 1, 2, 4 or 4. Optionally, "n" can be specified to represent the degree of branching or polymerization. "n" and "m" can be specified to represent the average in a composition comprising a plurality of antibodies.

In one embodiment, X represents a molecule comprising a moiety that is cleavable, e.g., under physiological conditions, optionally under intracellular conditions. In one embodiment, X represents a molecule comprising (i) a spacer (Y), (ii) a cleavable moiety and (iii) an optional self-eliminating or non-self-eliminating spacer system (Y'). The spacer Y can be positioned between the Ab and the cleavable moiety, and the spacer system (Y') can be positioned between the cleavable moiety and Z. Molecule X or spacer Y can optionally be specified as comprising a reactive group (R) or the residue of the reaction of reactive group R with an amino acid of the antibody or with a complementary reactive group (R') that is attached to an amino acid of the antibody.

The variable m represents the number of —X—$(Z)_n$ moieties per antibody molecule in an immunoconjugate. In a composition comprising a plurality of anti-Nectin-4 ADCs, the number "m" of number of —X—Z moieties per antibody molecule may vary. Thus, in exemplary compositions comprising a plurality of immunoconjugates of the formulae herein, m is the average number of —X—$(Z)_n$ moieties per Ab, in which case m can also be referred to as the average drug loading or drug:antibody ratio (DAR). Average drug loading or DAR may advantageously range from 1 to about 8 (—X—$(Z)_n$) moieties per Ab. The number of Z moieties attached to a moiety X, "n", can for example be 1 or 2. Typically, n is 1. In some embodiments, n is 1, and m represents the average drug loading, m is between 2 and 8. In some embodiments, n is 1, and m represents the average drug loading, m is between 2 and 6. In some embodiments, n is 1, and m represents the average drug loading, m is between 4 and 8. In some embodiments, n is 1, and m represents the average drug loading, m is between 6 and 8, optionally about 6, 7 or 8. In some embodiments, n is 1, and m represents the average drug loading, m is between 4 and 6, optionally about 4, 5 or 6.

The number of (—X—Z) moieties per Ab may be characterized by conventional means such as mass spectroscopy, ELISA assay, and HPLC. The quantitative distribution of immunoconjugates in terms of m may also be determined. In some instances, separation, purification, and characterization of homogeneous immunoconjugates where m is a certain value, as distinguished from immunoconjugates with other drug loadings, may be achieved by means such as reverse phase HPLC or electrophoresis.

In one embodiment, an anti-Nectin-4 composition used in the treatment methods of the disclosure is characterized as comprising a plurality immunoconjugates represented by Formula (I):

$$Ab\text{-}(X—(Z)_n)_m \qquad \text{Formula (II)}$$

wherein,

Ab is an anti-Nectin-4 antigen binding protein (e.g. an antibody or antibody fragment);

X is a molecule which connects Ab and Z, e.g., the residue of a linker following covalent linkage to one or both of Ab and Z;

Z is a camptothecin analogue comprising an exatecan or a SN-38 molecule, e.g., a molecule comprising the structure of Compounds 1 or 2;

n is 1 or 2; and wherein at least 50%, 60%, 70%, 80%, 90%, 95%, 98% or 99% of immunoconjugates in an antibody sample have an m (the number of X—Z moieties) that is 2 or 4, at least 2, between 2 and 4, at least 4, between 4 and 6 or between 4 and 8, optionally wherein n is 1 and at least 50%, 60%, 70%, 80%, 90%, 95%, 98% or 99% of immunoconjugates in an antibody sample have an m (the number of X—Z moieties) that is 2 or 4, at least 2, between 2 and 4, at least 4, between 4 and 6 or between 4 and 8.

In one embodiment, an anti-Nectin-4 composition used in the treatment methods of the disclosure is characterized as comprising a plurality immunoconjugates represented by Formula (I):

$$Ab\text{-}(X—(Z)_n)_m \qquad \text{Formula (II)}$$

wherein,

Ab is an anti-Nectin-4 antigen binding protein (e.g. an antibody or antibody fragment);

X is a molecule which connects Ab and Z, e.g., the residue of a linker following covalent linkage to one or both of Ab and Z;

Z a camptothecin analogue comprising an exatecan or a SN-38 molecule, e.g., a molecule comprising the structure of Compounds 1 or 2;

n is 1; and wherein at least 50%, 60%, 70%, 80%, 90%, 95%, 98% or 99% of immunoconjugates in an antibody sample have an m (the number of X—Z moieties) that is 6, at least 6, between 6 and 8, or 8.

In one embodiment, an anti-Nectin-4 composition used in the treatment methods of the disclosure is characterised as comprising a plurality immunoconjugates represented by Formula (I):

$$Ab\text{-}(X—(Z)_n)_m \qquad \text{Formula (II)}$$

wherein,

Ab is an anti-Nectin-4 antigen binding protein (e.g. an antibody or antibody fragment);

X is a molecule which connects Ab and Z, e.g., the residue of a linker following covalent linkage to one or both of Ab and Z;

Z a camptothecin analogue comprising an exatecan or a SN-38 molecule, e.g., a molecule comprising the structure of Compounds 1 or 2;

n is 1; and wherein at least 50%, 60%, 70%, 80%, 90%, 95%, 98% or 99% of immunoconjugates in an antibody sample have an m (the number of X—Z moieties) that is 8.

A variety of methods can be used to covalently link the linker comprising the cytotoxic agent to the antibody or antigen binding protein, either non-specifically or specifically to a particular amino acid residue. The linker (X) can comprise a moiety that is cleavable, e.g., under physiological conditions, optionally as shown in the Examples under intracellular conditions, such that cleavage of the linker releases the cytotoxic agent in the intracellular environment. The linker can be bonded to a chemically reactive group on the antibody molecule, e.g., to a free amino, imino, hydroxyl, thiol or carboxyl group (e.g., to the N- or C-terminus, to the epsilon amino group of one or more lysine residues, the free carboxylic acid group of one or more glutamic acid or aspartic acid residues, or to the sulfhydryl group of one or more cysteinyl residues), to a carbohydrate, or generally to any reactive group introduced or engineered into an antibody. The site to which the linker is bound can be a natural residue in the amino acid sequence of the antibody molecule or it can be introduced into the antibody molecule, e.g., by DNA recombinant technology (e.g., by introducing a cysteine or protease cleavage site in the amino acid sequence, by introducing a non-natural amino acid residue) or by protein biochemistry (e.g., reduction, pH adjustment or proteolysis, by glycoengineering, enzymatic modification of an amino acid-bound glycan).

In certain embodiments, an intermediate, which is the precursor of the linker (X), is reacted with the cytotoxic agent (Z) under appropriate conditions. In certain embodiments, reactive groups are used on the cytotoxic agent and/or the intermediate. In some embodiments, the product of the reaction between the cytotoxic agent and the intermediate, or the derivatized cytotoxic agent, is subsequently reacted with the antibody molecule under appropriate conditions. In other embodiments, a precursor of the linker (X) is first reacted with the antibody molecule under appropriate conditions so at to yield an antibody bound to the precursor of the linker (X), and the antibody is subsequently reacted with a molecule comprising the cytotoxic agent (Z).

In some embodiments, the linker (X) is cleavable by a cleaving agent that is present in the intracellular environment (e.g., within a lysosome or endosome or caveolea). The linker can comprise for example a peptidyl linker or amino acid unit that is cleaved by an intracellular peptidase or protease enzyme, including, but not limited to, a lysosomal or endosomal protease. In some embodiments, a peptidyl linker moiety is at least two amino acids long or at least three amino acids long. Cleaving agents can include cathepsins B and D and plasmin, all of which are known to hydrolyze dipeptide drug derivatives resulting in the release of active drug inside target cells. Most typical are peptidyl linkers that are cleavable by enzymes that are present in cells. In a specific embodiment, the peptidyl linker cleavable by an intracellular protease is a Val-Cit linker or a phenylalanine-lysine (Phe-Lys) linker (see, e.g., U.S. Pat. No. 6,214,345, which describes the synthesis of doxorubicin with the valine-citrulline linker). A valine-citrulline (Val-Cit) element can have the structure shown below:

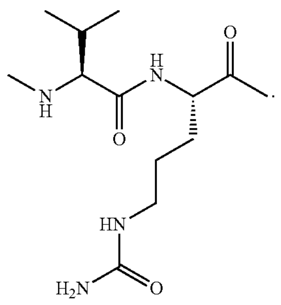 [SMILES: CN[C@H](C(=O)N[C@@H](CCCNC(N)=O)C(C)=O)C(C)C]

In another specific embodiment, the peptidyl linker cleavable by an intracellular protease is a valine-alanine (Val-Ala) linker. A val-ala element can have the structure is shown below:

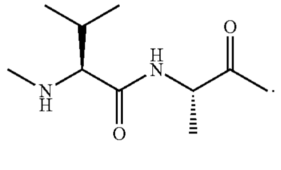

In another specific embodiment, the peptidyl linker cleavable by an intracellular protease is a glycine-containing oligopeptide linker, for example glycine- and phenylalanine-containing oligopeptide linker, optionally a GGFG, GGFGG or GGFGGG linker (see, e.g., U.S. Pat. No. 6,835,807, the disclosure of which is incorporated herein by reference).

In some embodiments, and optionally in addition to being cleavable by an intracellular protease, a linker can function to act as a spacer or stretcher to distance an antibody from Z in order to avoid interference with the ability of the antibody to bind Nectin-4 and/or inhibit cell-cell interactions mediated by Nectin-4. A linker may comprise a spacer unit (Y) and/or a spacer or spacer system (Y'). The spacer Y can thus be positioned between the Ab and the cleavable moiety. The spacer system (Y') can be positioned between the cleavable moiety and Z. or spacer Y (or linker X that comprises it) can optionally be specified as comprising a reactive group (R) or the residue of the reaction of reactive group R with an amino acid of the antibody or with a complementary reactive group (R') that is attached to an amino acid of the antibody. The spacer Y can for example be a molecule that forms a bond (e.g. via its reactive group R) with an amino acid of the antibody, e.g., a sulfur atom, a primary or secondary amino group or a carbohydrate group of the antibody, and which spacer or stretcher (Y) links the antibody to the cytotoxic agent (Z) or to a cleavable amino acid unit (e.g. the peptidyl linker, a cleavable di-, tri-, tetra- or penta-peptide, optionally further with a self-eliminating and/or non-self-eliminating spacer (Y') which is in turn linked to Z. Thus, when the spacer (Y) is linked at one end to an amino acid unit (e.g. a cleavable di-, tri-, tetra- or penta-peptide), the cleavable amino acid unit can in turn be directly linked to Z or can comprise a further spacer (Y') such as a non-self immolative or a self immolative spacer which links the amino acid unit and Z.

Spacer (Y) can optionally be specified as being or comprising a substituted or unsubstituted alkyl or heteroalkyl chain, optionally wherein Y has a chain length of 2-100 atoms, optionally 2-40, 2-30, 2-20, 4-40, 4-30 or 4-20 atoms, optionally where one or more atoms can be other than carbon, for example oxygen, sulfur, nitrogen, or other atoms, optionally wherein any carbon of the chain is substituted with an alkoxy, hydroxyl, alkylcarbonyloxy, alkyl-S—, thiol, alkyl-C(O)S—, amine, alkylamine, amide, or alkylamide. Spacer (Y) can optionally be specified as comprising a stability-enhancing moiety.

For example, spacer Y can orthogonal poly-ethyleneglycol (PEG) moieties or polysarcosine (poly-N-methylglycine or PSAR) moieties in the linker design (see, e.g., WO2019/081455, WO2015/057699 and WO2016/059377, the disclosure of which are incorporated herein by reference).

In some specific embodiments, spacer (Y) may comprise one or more ethylene oxide monomers, optionally Y comprises a polyethylene oxide moiety, optionally Y comprises between 1 and 24, optionally 1 and 12, optionally 1 and 8, optionally 1 and 6 polyethylene oxide moieties, optionally Y comprises a structure $—(CH_2CH_2O)_x—$ where x is 1 to 12, optionally 1 to 8, optionally 1 to 6.

An example of a suitable stability-enhancing moiety, spacer chain Y can comprise a stability-enhancing moiety disclosed in PCT publication nos. WO2015/057699 or WO2019/081455. For example, spacer chain Y can comprise an orthogonal connector moiety and stability-enhancing moiety. The stability-enhancing moiety can be a PEG homopolymer, or generally any single molecular weight homopolymer (e.g. a PEG or polysarcosine homopolymer) bound to the orthogonal connector moiety. The homopolymer can have for example 1-4, 1-6, 1-8, 1-10, 1-12, at least 6, 8 or 10, or 6-12, 6-24, 6-72 units of the PEG or other monomer. The term orthogonal connector refers to a branched linker unit component that connects a linker moiety (e.g. the chain of spacer Y) to a homopolymer unit and via a linker (e.g. a cleavable oligopeptide (Pep) and spacer Y') to a cytotoxic agent (Z) so that the homopolymer unit is in a parallel configuration (as opposed to a series configuration) in relation to the cytotoxic agent (the homopolymer is in parallel to the Pep-Y'—Z moiety). The orthogonal connector moiety can for example be one or more natural or non-natural amino acids optionally selected from glutamic acid, lysine and glycine. Optionally, the amino acid orthogonal connector moiety is placed at the end of spacer chain Y such that the orthogonal connector moiety amino acid residue is connected, via a peptide bond between the α-carboxyl group of one amino acid to the α-amino group of the other amino acid, to an amino acid residue of the peptidyl linker (e.g. (Pep) in Formula V or VI). Y can for example comprise the result of the reaction of the orthogonal connector moiety with a moiety of Formula D:

Formula D

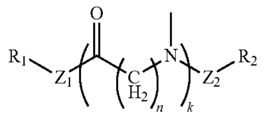

wherein $R_1$ and $R_2$ are different, and one of $R_1$ and $R_2$ is H or an inert group, the other one of $R_1$ and $R_2$ being functionalized reactive group, said group being reactive for covalently binding to a bindable group of the orthogonal connector moiety, in such reaction conditions that the inert group is non-reactive, $Z_1$ and $Z_2$, identical or different, are optional spacers, and n is 1 or more and k is 2 or more.

In another example, spacer Y comprises a group disclosed in US patent publication no. US2017/0072068A1, the disclosures of which are incorporated herein by reference, for example a group according to formula (E) or a salt thereof:

Formula E

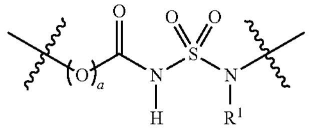

wherein a is 0 or 1; and $R^1$ is selected from the group consisting of hydrogen, $C_1$-$C_{24}$ alkyl groups, $C_3$-$C_{24}$ cycloalkyl groups, $C_2$-$C_{24}$ (hetero)aryl groups, $C_3$-$C_{24}$ alkyl(hetero)aryl groups and $C_3$-$C_{24}$ (hetero)arylalkyl groups, the $C_1$-$C_{24}$ alkyl groups, $C_3$-$C_{24}$ cycloalkyl groups, $C_2$-$C_{24}$ (hetero)aryl groups, $C_3$-$C_{24}$ alkyl (hetero)aryl groups and $C_3$-$C_{24}$ (hetero)arylalkyl groups optionally substituted and optionally interrupted by one or more heteroatoms selected from O, S and $NR^3$ wherein $R^3$ is independently selected from the group consisting of hydrogen and $C_1$-$C_4$ alkyl groups; and wherein the group according to formula E, or the salt thereof, is situated in between said the first end and the second end of the spacer chain Y.

The spacer or spacer system (Y') placed between the amino acid unit (e.g. a cleavable di-, tri-, tetra- or penta-peptide) and Z may be self-eliminating or non-self-eliminating. A spacer Y' may for example comprise a substituted or unsubstituted alkyl or heteroalkyl chain, optionally wherein Y has a chain length of 2-30 atoms, optionally 2-20, 4-20, 2-10 or 4-20 atoms, optionally where one or more atoms can be other than carbon, for example oxygen, sulfur, nitrogen, or other atoms, optionally wherein any carbon of the chain is substituted with an alkoxy, hydroxyl, alkylcarbonyloxy, alkyl-S—, thiol, alkyl-C(O)S—, amine, alkylamine, amide, or alkylamide. In one embodiment, Y' comprises a p-aminobenzyloxycarbonyl group. In one embodiment, Y' is a non-self-eliminating spacer and comprises a (CH2-C(=O)) group, for example Y' can be or can comprise a —O—CH2-C(=O)—, HO—O—CH2-C(=O)—, —CH2CH2-C(=O)—, —CH2CH2CH2-C(=O)—, —CH2-O—CH2-C(=O)— or a —CH2CH2-O—CH2-C(=O)— group.

A "self-eliminating" spacer unit allows for release of the drug moiety without a separate hydrolysis step. When a self-eliminating spacer is used, after cleavage or transformation of the amino acid unit, the side of the spacer linked to the amino acid unit becomes unblocked, which results in eventual release of one or more moieties Z. The self-elimination spacer systems may for example be those described in WO02/083180 and WO2004/043493, the disclosures of which are incorporated herein by reference in their entirety, as well as other self-elimination spacers known to a person skilled in the art. In certain embodiments, a spacer unit of a linker comprises a p-aminobenzyl unit. In one such embodiment, a p-aminobenzyl alcohol is attached to an amino acid unit via an amide bond, and a carbamate, methylcarbamate, or carbonate is made between the benzyl alcohol and a cytotoxic agent. In one embodiment, the spacer unit is p-aminobenzyloxycarbonyl (PAB). Examples of self-eliminating spacer units further include, but are not limited to, aromatic compounds that are electronically similar to p-aminobenzyl alcohol (see, e.g., US 2005/0256030 A1), such as 2-aminoimidazol-5-methanoi derivatives (Hay et al. (1999) Bioorg. Med. Chem. Lett. 9:2237) and ortho- or para-aminobenzylacetals. Spacers can be used mat undergo cyclization upon amide bond hydrolysis, such as substituted and unsubstituted 4-aminobutyric acid amides (Rodrigues et al., Chemistry Biology, 1995, 2, 223) and 2-aminophenylpropionic acid amides (Amsberry, et al., J. Org. Chem., 1990, 55. 5867). Elimination of amine-containing drugs that are substituted at the a-position of glycine (Kingsbury, et al., J. Med. Chem., 1984, 27, 1447) are also examples of self-immolative spacers. A p-aminobenzyl self-eliminating spacer (e.g. PAB) is particularly suited for use together with a Phe-Lys, Val-Ala or Val-Cit cleavable dipeptide unit (the PAB is placed between the dipeptide and the camptothecin analogue (Z).

A "non-self-eliminating" spacer unit is one in which part or all of the spacer unit remains bound to the moiety Z upon enzymatic (e.g., proteolytic) cleavage of the antibody-moiety-of-interest conjugate. Examples of non-self-eliminating spacer units adapted for use as a spacer between a Gly-Gly-Phe-Gly amino acid unit and an exatecan molecule include, but are not limited to, include —O—$CH_2$—C(=O)—, HO—O—$CH_2$—C(=O)—, —$CH_2CH_2$—C(=O)—, —$CH_2CH_2CH_2$—C(=O)—, —$CH_2$—O—$CH_2$—C(=O)— and —$CH_2CH_2$—O—$CH_2$—C(=O)— (e.g., to form a GGFG-$CH_2CH_2$—O—$CH_2$—C(=O)-exatecan unit). Use of such a spacer between the GGFG amino acid unit and exatecan results in the release of an exatecan-comprising molecule having the structure of Compound 3. Other examples of non-self-eliminating spacer units include, but are not limited to, a glycine spacer unit and a glycine-glycine spacer unit. Other known combinations of peptidic spacers susceptible to sequence-specific enzymatic cleavage can be used in a similar manner. For example, enzymatic cleavage of an antibody-moiety-of-interest conjugate containing a glycine-glycine spacer unit by a tumor cell associated protease would result in release of a glycine-glycine-drug moiety from the remainder of the antibody-moiety-of-interest conjugate. In one such embodiment, the glycineglycine-drug moiety is then subjected to a separate hydrolysis step in the tumor cell, thus cleaving the glycine-glycine spacer unit from the drug moiety.

An exemplary linker-camptothecin moiety (X—Z) can comprise any of the structures shown below in Formulae III and IV, wherein Z is the camptothecin analogue and Y and Y' are spacers.

Formula IIIa

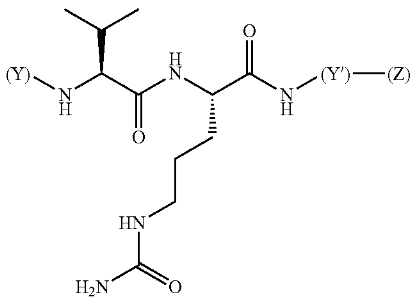

Formula IIIb

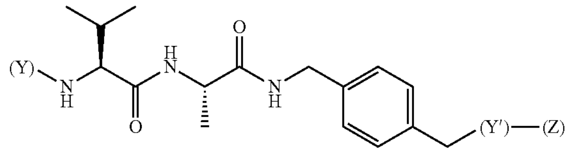

Formula IIIc

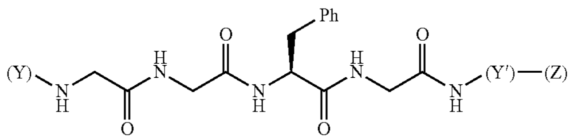

Formula IVa

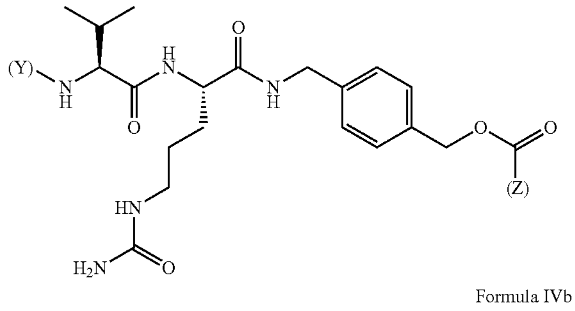

Formula IVb

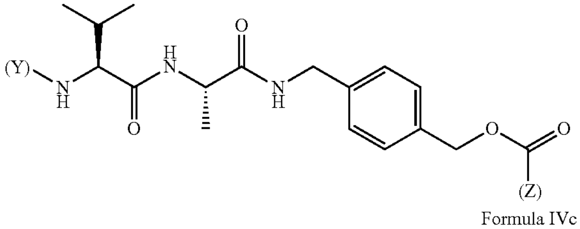

Formula IVc

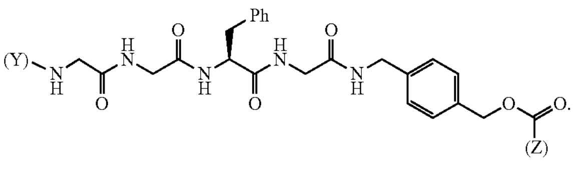

Spacers (Y) and (Y') can optionally be specified as being independently selected from the group consisting of linear or branched $C_1$-$C_{20}$ alkylene groups, $C_2$-$C_{20}$ alkenylene groups, $C_2$-$C_{20}$ alkynylene groups, $C_3$-$C_{20}$ cycloalkylene groups, $C_5$-$C_{20}$ cycloalkenylene groups, $C_8$-$C_{20}$ cycloalkynylene groups, $C_7$-$C_{20}$ alkylarylene groups, $C_7$-$C_{20}$ arylalkylene groups, $C_8$-$C_{20}$ arylalkenylene groups and $C_9$-$C_{20}$ arylalkynylene groups, alkylene groups, alkenylene groups, alkynylene groups, cycloalkylene groups, cycloalkenylene groups, cycloalkynylene groups, alkylarylene groups, arylalkylene groups, arylalkenylene groups and arylalkynylene groups being optionally substituted and optionally interrupted by one or more heteroatoms selected from the group of O, S and $NR^1$, wherein $R^1$ is independently selected from the group consisting of hydrogen, $C_1$-$C_{24}$ alkyl groups, $C_2$-$C_{24}$ alkenyl groups, $C_2$-$C_{24}$ alkynyl groups and $C_3$-$C_{24}$ cycloalkyl groups, the alkyl groups, alkenyl groups, alkynyl groups and cycloalkyl groups being optionally substituted.

Spacer (Y) and (Y') can optionally be specified as being or comprising a $C_1$-$C_{10}$ alkylene-, —$C_1$-$C_{10}$ heteroalkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$heterocyclo)-$C_1$-$C_{10}$ alkylene-, —$C_1$-$C_{10}$ alkylene-C(═O)—, —$C_1$-$C_{10}$ heteroalkylene-C(═O)—, —$C_3$-$C_8$carbocyclo-C(═O)—, —O—($C_1$-$C_8$alkyl)-C(═O)—, -arylene-C(═O)—, —$C_1$-$C_{10}$ alkylene-arylene-C(═O)—, -arylene-$C_1$-$C_{10}$ alkylene-C(═O)—, —$C_1$-$C_{10}$ alkylene-($C_3$-$C_8$carbocyclo)-C(═O)—, —($C_3$-$C_8$carbocyclo)-$C_1$-$C_{10}$ alkylene-C(═O)—, —$C_3$-$C_8$heterocyclo-C(═O)—, —$C_1$-$C_{10}$ alkylene-($C_3$-$C_8$heterocyclo)-C(═O)—, —($C_3$-$C_8$heterocyclo)-$C_1$-$C_{10}$ alkylene-C(═O)—, —$C_1$-$C_{10}$ alkylene-NH—, —$C_1$-$C_{10}$ heteroalkylene-NH—, —$C_3$-$C_8$carbocyclo-NH—, —O—($C_1$-$C_8$alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$carbocyclo)-NH—, —($C_3$-$C_8$carbocyclo)-$C_1$-$C_{10}$ alkylene-NH—, —$C_3$-$C_8$heterocyclo-NH—, —$C_1$-$C_{10}$ alkylene-($C_3$-$C_8$heterocyclo)-NH—, —($C_3$-$C_8$ heterocyclo)-$C_1$-$C_{10}$ alkylene-NH—, —$C_1$-$C_{10}$ alkylene-S—, —$C_1$-$C_{10}$ heteroalkylene-S—, —$C_3$-$C_8$carbocyclo-S—, —O—($C_1$-$C_8$ alkyl)-)—S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$carbocyclo)-S—, —($C_3$-$C_8$ carbocyclo)-$C_1$-$C_{10}$alkylene-S—, —$C_3$-$C_8$ heterocyclo-S—, —$C_1$-$C_{10}$alkylene-($C_3$-$C_8$ heterocyclo)-S—, —($C_3$-$C_8$ heterocyclo)-$C_1$-$C_{10}$ alkylene-S—, —$C_1$-$C_{10}$ alkylene-O—C(═O)—, —$C_3$-$C_8$carbocyclo-O—C(═O)—, —O—($C_1$-$C_8$alkyl)-O—C(═O)—, -arylene-O—C(═O)—, —$C_1$-$C_{10}$ alkylene-arylene-O—C(═O)—, -arylene-$C_1$-$C_{10}$ alkylene-O—C(═O)—, —$C_1$-$C_{10}$ alkylene-($C_3$-$C_8$carbocyclo)-O—C(═O)—, —($C_3$-$C_8$carbocyclo)-$C_1$-$C_{10}$ alkylene-O—C(═O)—, —$C_3$-$C_8$heterocyclo-O—C(═O)—, —$C_1$-$C_{10}$ alkylene-($C_3$-$C_8$heterocyclo)-O—C(═O)—, —($C_3$-$C_8$heterocyclo)-$C_1$-$C_{10}$ alkylene-O—C(═O)—, in each case optionally substituted with one or more of the substituents selected from: —X, —R', —O, —OR', ═O, —SR', —$S^-$, —$NR'_2$, ═NR', —$CX_3$, —CN, —OCN, —SCN, —N═C═O, —NCS, —NO, —$NO_2$, ═$N_2$, —$N_3$, —NR'C(═O)R', —C(═O)R', —C(═O)$NR'_2$, —$SO_3^-$, —$SO_3H$, —S(═$O)_2$R', —OS(═$O)_2$OR', —S(═$O)_2$NR', —S(═O)R', —OP(═O)$(OR')_2$, —P(═O)$(OR')_2$, —$PO_3$, —$PO_3H_2$, —C(═O)X, —C(═S)R', —$CO_2$R', —$CO_2$, —C(═S)OR', C(═O)SR', C(═S)SR', C(═O)$NR'_2$, C(═S)$NR'_2$, and C(═NR')$NR'_2$, where each X is independently a halogen: —F, —Cl, —Br, or —I; and each R' is independently —H, —$C_1$-$C_{20}$ alkyl, —$C_6$-$C_{20}$ aryl, or —$C_3$-$C_{14}$heterocycle.

Spacer (Y) can optionally be specified as comprising, e.g., at one end of the chain, a reactive group (R) that is reactive with a free amino, hydroxyl, sulfhydryl or carboxyl group, or carbohydrate, on the antibody, or reactive with a complementary reactive group (R') that is attached to an amino acid (e.g., via a free amino, hydroxyl, sulfhydryl or carboxyl group, or carbohydrate) of the antibody, or, upon conjugation to an anti-Nectin-4 antibody, the residue of the reaction of a reactive group (R) with a free amino, hydroxyl, sulfhydryl or carboxyl group on the antibody or with a complementary reactive group (R') that is attached to an amino acid of the antibody. Examples of reactive group pairs R and R' include a range of groups capable of biorthogonal reaction, preferably a cycloaddition, for example a Diels-Alder reaction or a 1,3-dipolar cycloaddition, for example between azides and cyclooctynes (copper-free click chemistry), between nitrones and cyclooctynes, oxime/hydrazone formation from aldehydes and ketones and the tetrazine ligation (see also WO2013/092983 or US2017/0072068A1, the disclosures of which are incorporated herein by reference). For example R can be an alkyne and R' can be an azide, or R can be an azide and R' an alkyne. The resulting linker and functionalized antibody, or the Y element thereof, can thus in any embodiment comprise a group (RR') resulting from the reaction of R and R', for example RR' can be or comprise a triazole resulting from the reaction of an alkyne and an azide.

In one embodiment, the reactive groups R and R' are complementary reagents together capable of undergoing a "click" reaction (i.e., a Click Chemistry reagent or reactive group). For example a 1,3-dipole-functional compound can react with an alkyne in a cyclization reaction to form a heterocyclic compound, preferably in the substantial absence of added catalyst (e.g., Cu(I)). A variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

Examples include o-phosphenearomatic ester, an azide, a fulminate, an alkyne (including any strained cycloalkyne), a cyanide, an anthracene, a 1,2,4,5-tetrazine, or a norbornene (or other strained cycloalkene).

In one embodiment, R is a moiety having a terminal alkyne or azide; such moieties are described for example in U.S. Pat. No. 7,763,736, the disclosure of which is incorporated herein by reference. Suitable reaction conditions for use of copper (and other metal salt) as catalysts of click-reactions between terminal alkynes and azides are provided in U.S. Pat. No. 7,763,736.

In one embodiment, R is a substituted or unsubstituted cycloalkyne. Cycloalkynes, including specific compounds, are described for example in U.S. Pat. No. 7,807,619, the disclosure of which is incorporated herein by reference.

In some embodiments, a cycloalkyne may be a compound of Formula A:

Formula A

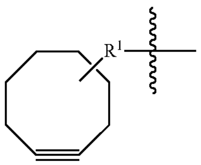

where:

$R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, and a halosulfonyl;

$R^1$ can be at any position on the cyclooctyne group other than at the two carbons joined by the triple bond.

In some embodiments, the modified cycloalkyne is of Formula A, wherein one or more of the carbon atoms in the cyclooctyne ring, other than the two carbon atoms joined by a triple bond, is substituted with one or more electron-withdrawing groups, e.g., a halo (bromo, chloro, fluoro, iodo), a nitro group, a cyano group, a sulfone group, or a sulfonic acid group. Thus, e.g., in some embodiments, a subject modified cycloalkyne is of Formula B:

Formula B

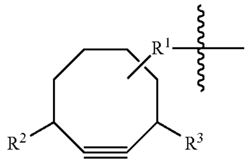

where:

each of $R^2$ and $R^3$ is independently: (a) H; (b) a halogen atom (e.g., bromo, chloro, fluoro, iodo); (c) $-W-(CH_2)_n-Z$ (where: n is an integer from 1-4 (e.g., n=1, 2, 3, or 4); W, if present, is O, N, or S; and Z is nitro, cyano, sulfonic acid, or a halogen); (d) $-(CH_2)_n-W-(CH_2)_m-R^4$ (where: n and m are each independently 1 or 2; W is O, N, S, or sulfonyl; if W is O, N, or S, then $R^4$ is nitro, cyano, or halogen; and if W is sulfonyl, then $R^4$ is H); or (e) $-CH_2)_n-R^4$ (where: n is an integer from 1-4 (e.g., n=1, 2, 3, or 4); and $R^4$ is nitro, cyano, sulfonic acid, or a halogen); and $R^1$ is selected from a carbonyl, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone and a halosulfonyl. $R^1$ can be at any position on the cyclooctyne group other than at the two carbons linked by the triple bond.

In one embodiment, R is a substituted or unsubstituted heterocyclic strained alkyne. Cycloalkynes, including specific compounds, are described for example in U.S. Pat. No. 8,133,515, the disclosure of which is incorporated herein by reference. In one embodiment, the alkyne is of the Formula C:

Formula C

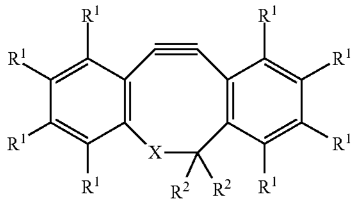

wherein:

each $R^1$ is independently selected from the group consisting of hydrogen, halogen, hydroxy, alkoxy, nitrate, nitrite, sulfate, and a $C_1$-$C_{10}$ alkyl or heteroalkyl;

each $R^2$ is independently selected from the group consisting of hydrogen, halogen, hydroxy, alkoxy, nitrate, nitrite, sulfate, and a $C_1$-$C_{10}$ organic group; X represents N—$R^3R^4$, NH—$R^4$, CH—N—$OR^4$, C—N—$NR^3R^4$, $CHOR_4$, or $CHNHR_4$; and each $R^3$ represents hydrogen or an organic group and $R^4$ represents linking moiety C of a linker. In one embodiment, R or R' is a DBCO (dibenzycyclooctyl) group below:

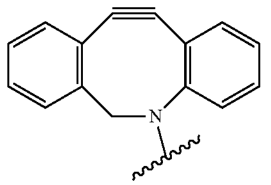

DBCO

Alkynes such as those described herein above can be reacted with at least one 1,3-dipole-functional compound in a cyclization reaction to form a heterocyclic compound, preferably in the substantial absence of added catalyst (e.g., Cu(I)). A wide variety compounds having at least one 1,3-dipole group attached thereto (having a three-atom pi-electron system containing 4 electrons delocalized over the three atoms) can be used to react with the alkynes disclosed herein. Exemplary 1,3-dipole groups include, but are not limited to, azides, nitrile oxides, nitrones, azoxy groups, and acyl diazo groups.

In the Formulae herein, Y' can be optionally absent or can be a spacer, optionally a self-eliminating spacer, for example comprising a p-aminobenzyl unit, or a non-self-eliminating spacer. Optionally, Y' is or comprises a substituted or unsubstituted alkyl or heteroalkyl chain, optionally wherein Y' has a chain length of 2-40 atoms, optionally 2-30, 2-20, 4-40, 4-30 or 4-20 atoms, optionally where one or more atoms can be other than carbon, for example oxygen, sulfur, nitrogen, or other atoms, optionally wherein any carbon of the chain is substituted with an alkoxy, hydroxyl, alkylcarbonyloxy, alkyl-S—, thiol, alkyl-C(O)S—, amine, alkylamine, amide, or alkylamide.

An exemplary linker-camptothecin molecule (e.g. an X—Z moiety of Formulae I to XI) that can be conjugated to an anti-Nectin-4 binding protein can optionally be represented by Formula V:

(R)—(Y)-(Pep)-(Y')—(Z) Formula (V)

wherein,

R is a group reactive with a free amino, hydroxyl, sulfhydryl or carboxyl group on the antibody, or reactive with a complementary reactive group (R') that is attached to an amino acid of the antibody, or, upon conjugation to the anti-Nectin-4 binding protein R is the residue of the reaction of a reactive group (R) with a free amino, hydroxyl, sulfhydryl or carboxyl group on the antibody or with a complementary reactive group (R') that is attached to an amino acid of the antibody;

Y is optionally absent or is a spacer;

Pep is or comprises a peptidyl linker that is cleaved by an intracellular peptidase or protease enzyme, for example a valine-citrulline, valine-alanine or phenylalanine-lysine dipeptide;

Y' is optionally absent or is a spacer, optionally a self-eliminating spacer or a non-self-eliminating spacer; and Z is a camptothecin analogue or derivative, optionally an exatecan or SN-38 molecule.

A resulting Nectin-4 binding immunoconjugate according to the invention can for example be represented by Formula (VI):

Ab-(Y)-(Pep)-(Y')—(Z) Formula (VI)

wherein,

Ab is an anti-Nectin-4 antigen binding protein (e.g. an antibody);

Y is optionally absent or is a spacer. Optionally Formula VI comprises, between (Ab) and (Y), the residue of the reaction of a reactive group (e.g. a maleimide, a primary amine) with the side chain or carbohydrate of an amino acid of anti-Nectin-4 antigen binding protein (Ab). Alternatively, the residue of the reaction of a reactive group (e.g. a maleimide, a primary amine) with the side chain of an amino acid of anti-Nectin-4 antigen binding protein (Ab) can be specified as being comprised in Y;

Pep is or comprises an amino acid unit (e.g. peptidyl linker) that is cleaved by an intracellular peptidase or protease enzyme, (e.g., (Pep) is a protease-cleavable di-, tri-, tetra- or penta-peptide, for example a valine-citrulline, valine-alanine or phenylalanine-lysine unit);

Y' is optionally absent or is a spacer, optionally a self-eliminating spacer or a non-self-eliminating spacer; and Z is a camptothecin analogue or derivative, optionally an exatecan or SN-38 molecule.

Optionally, the formula can be specified as comprising (e.g. between (Ab) and the end of Y (or (Pep or X) if Y is absent)) the residue (RR') of the reaction of a reactive group (R) with a free amino, hydroxyl, sulfhydryl or carboxyl group on the antibody or with a complementary reactive group (R') that is attached to an amino acid of the antibody.

In one example, where (RR') is the residue of the reaction of a reactive group (R) with a complementary reactive group (R') that is attached to the antibody (e.g. R' is attached to a side chain or glycan of an amino acid of the antibody), the Nectin-4 binding immunoconjugate according to the invention can for example be represented by Formula ($VI_{bis}$):

Ab-(RR')—(Y)-(Pep)-(Y')—(Z) Formula ($VI_{bis}$)

wherein, Ab, Y, Pep, Y' and Z are as defined in Formula VI, and RR' is the result of biorthogonal reaction, preferably a cycloaddition, for example a Diels-Alder reaction or a 1,3-dipolar cycloaddition. In one embodiment, RR' has a structure selected from the group consisting of:

($RR'^a$)

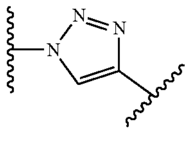

($RR'^b$)

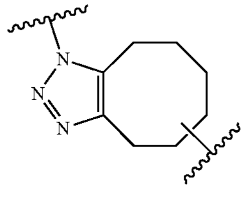

-continued (RR'$^c$)

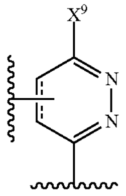

(RR'$^d$)

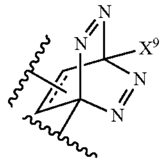

(RR'$^e$)

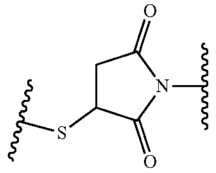

(RR'$^f$)

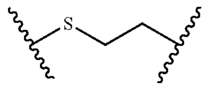

(RR'$^g$)

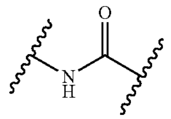

(RR'$^h$)

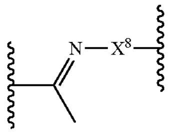

wherein $X^8$ is O or NH, $X^9$ is selected from H, methyl and pyridyl, and in structure (RR'$^c$) and (RR'$^d$), and the ⎓ bond represents either a single or a double bond.

In any embodiment, an exatecan molecule (or other 6-ring camptothecin) can be specified as being bound to Y' (or (Pep) if Y' is absent) via the amine at position 1 of exatecan.

In any embodiment, a SN-38 molecule (or other 5-ring camptothecin) can be specified as being bound to Y' (or (Pep) if Y' is absent) via the amine at position 9 of SN-38.

Camptothecin is well known, as are a wide range of camptothecin derivatives and analogues that share the core ring system with various substitutions, but preferably have modifications or substitutions in rings A and/or B compared to the basic camptothecin structure below:

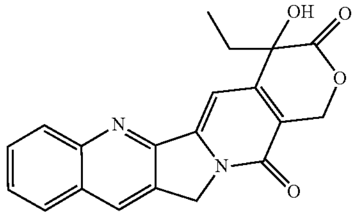

Ring (A) (B) (C) (D) (E)

Many camptothecin analogues have been reported including, topotecan, inirotecan, exatecan, DXd, 9-aminocamptothecin, 9-nitrocamptothecin, 10-hydroxycamptothecin, lurtotecan, camptothecin, gimatecan, belotecan, and rubitecan. Further camptothecin analogues are disclosed in Li et al., ACS Med. Chem. Lett. 2019, 10, 10, 1386-1392, Jpn. J. Cancer Res. 86: 776-782 and in Takiguchi et al. 1997 Jpn. J. Cancer Res. 88: 760-769, the disclosures of which are incorporated herein by reference. The four analogues topotecan, irinotecan, belotecan, and DXd (as part of trastuzumab deruxtecan) have been approved by the FDA. In one embodiment, the camptothecin analogue is a five-ring compound (e.g., the camptothecin lacks an F ring). In one embodiment, the camptothecin analogue is a six-ring compound, e.g., comprising the F ring.

Some examples such as the basic camptothecin structure, the SN-38 molecule (7-Ethyl-10-hydroxycamptothecin; active metabolite of irinotecan) and the camptothecin analogues disclosed in Li et al., ACS Med. Chem. Lett. 2019, 10, 10, 1386-139 have five rings (A, B, C, D and E rings) and can for example be attached to the linker (e.g. spacer Y or Y', or linker X) via a substituent on the B ring.

SN-38:

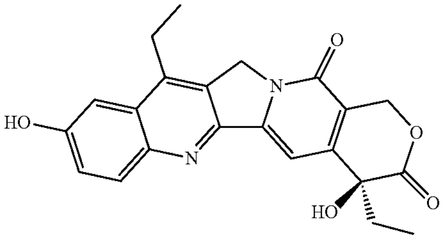 [SMILES: CCc1c2c(nc3ccc(O)cc13)-c1cc3c(c(=O)n1C2)COC(=O)[C@]3(O)CC]

Compounds of Li et al., ACS Med. Chem. Lett. 2019, 10, 10, 1386-1392:

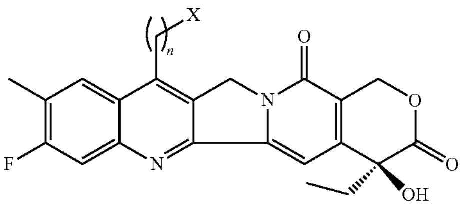

Optionally a camptothecin analogue is a six-ring compound (additionally an F ring), where the compound is attached to the linker through a substituent on such F ring. Examples of such six rings compounds include but are not limited to DXd and exatecan.

Camptothecin analogues thus include exatecan, SN-38, and any of a range of molecules that comprise such a moiety, for example an exatecan can unsubstituted or can be substituted at the position 1 amine, for example wherein the substituent is or comprises a —O—$CH_2$—C(═O)—, HO—O—$CH_2$—C(=O)—, —$CH_2CH_2$—C(=O)—, —$CH_2CH_2CH_2$—C(=O)—, —$CH_2$—O—$CH_2$—C(=O)—, —$CH_2CH_2$—O—$CH_2$—C(=O)— group or other group shown in U.S. Pat. No. 6,835,807, the disclosure of which is incorporated herein by reference.

In one embodiment, the antibody of the disclosure releases, in vivo or in vitro in presence of Nectin-4 expressing tumor cells (e.g. upon enzymatic cleavage of the cleavable moiety followed by self-elimination of the spacer Y') an exatecan molecule having the structure of Compound 1.

The camptothecin analogue or analogue exatecan is described in Mitsui et al. 1995 Jpn. J. Cancer Res. 86: 776-782 and in Takiguchi et al. 1997 Jpn. J. Cancer Res. 88: 760-769, the disclosures of which are incorporated herein by reference. The structure of exatecan is shown below in Compound 1a:

Compound 1a

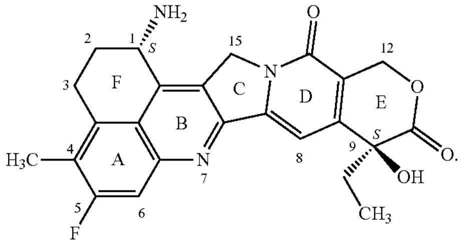

Exatecan can be coupled to a linker via the nitrogen atom of the amino group at position 1, such that the exatecan moiety, when bound to a linker or present within a linker-exatecan molecule (an (X—Z) molecule), for example as conjugated to an antibody, exatecan will have the structure of Compound 1 b:

Compound 1b

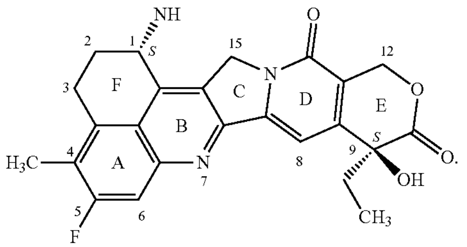

Thus, it will be understood that when exatecan of Compound 1a is attached to a linker (and, for example, when the linker is in turn attached to the antibody) via the amine at position 1, exatecan will be understood to be modified group at position 1 (i.e. the $NH_2$ group at position 1 is replaced by an NH, or alternatively an OH or O group). For example exatecan can be coupled to the antibody via a linker comprising a cleavable oligopeptide. Examples include di-, tri-, tetra- and penta-peptides such as the glycine and phenylalanine-containing peptides shown in U.S. Pat. No. 6,835,807, or the dipeptides valine-citrulline or valine-alanine attached to a PAB molecule, or the disclosures of which are incorporated herein by reference. Various suitable linker-Z structures are known that can liberate active exatecan or exatecan derivatives at the amino at position 1. For example, exatecan can be linked to a cleavable oligopeptide via a ($CH_2$—C(=O)) group attached to the position 1 amine, as shown in Formula III and Compound 13, resulting in the liberation of the exatecan-containing Compound 13. Examples of substituents at the $NH_2$ of position 1 of exatecan of Compound 1a include a ($CH_2$—C(=O)) comprising group such as —O—$CH_2$—C(=O)—, HO—O—$CH_2$—C(=O)—, —$CH_2CH_2$—C(=O)—, —$CH_2CH_2CH_2$—C(=O)—, —$CH_2$—O—$CH_2$—C(=O)— and —$CH_2CH_2$—O—$CH_2$—C(=O)—. An exatecan can be specified to be an exatecan derivative in which the $NH_2$ at position 1 is substituted, e.g. by an NH group, by an OH—$CH_2$—C(=O)—NH group. In one embodiment, a substituted exatecan or exatecan derivative (e.g. derived at position 1) has the structure of compound 13.

In one embodiment, the linker moiety (X—Z) is or comprises the structure shown in Formula VII, below, wherein (Y) is a spacer comprising (e.g., at its terminus) the residue of the reaction of a reactive group (R) with an amino acid residue, for example a free amino, hydroxyl, sulfhydryl or carboxyl group on the antibody (e.g., on the epsilon amino group of one or more lysine residues, the free carboxylic acid group of one or more glutamic acid or aspartic acid residues, or to the S atom of one or more cysteinyl residues). An anti-Nectin-4 binding protein functionalized with a linker comprising the structure of Formula VII or Compounds 3 or 4 will release or yield (e.g. intracellularly, in the presence of Nectin-4 expressing tumor cells) a compound having the structure of Compound 1a.

Formula VII

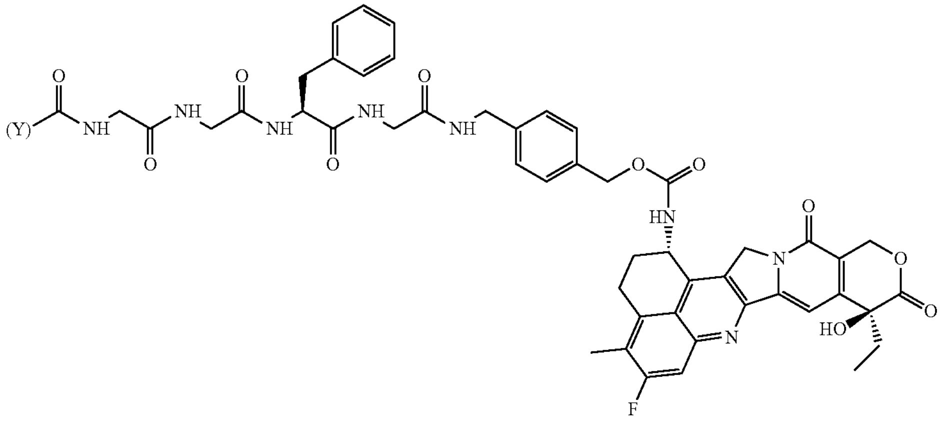

An exemplary linker having a maleimide as R group can have the structure of Compound 3, below. Such linker can be conjugated to an antibody via cysteine residues in the antibody after the interchain disulfide bounds are reduced with a reducing agent, e.g. tris (2-carboxyethyl) phosphine hydrochloride.

Compound 3

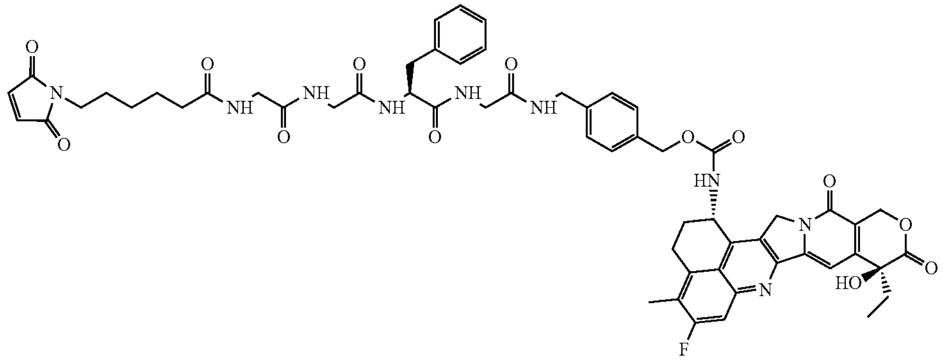

The resulting antibody-drug conjugate will comprise an antibody comprising one or a plurality of cysteine residues functionalized with a compound having the structure of Compound 3 (wherein Compound 3 is bound via the S atom of the cysteine residue).

In another embodiment, a linker can have a primary amine as R group, and when reacted with an antibody in the presence of a transglutaminase enzyme, can yield an antibody comprising one or a plurality of acceptor glutamine residues functionalized with the linker. For example, a linker (X—Z), or an antibody functionalized therewith, has or comprises the structure shown as Compound 4, below:

Compound 4

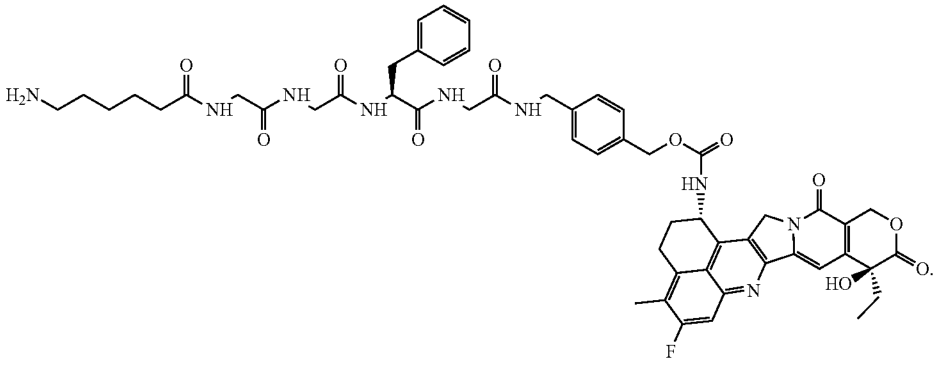

In one embodiment, the linker moiety (X—Z) is or comprises the structure shown in Formula VIII, below, wherein (Y) is a spacer comprising (e.g., at its terminus) the residue of the reaction of a reactive group (R) with an amino acid residue, for example a free amino, hydroxyl, sulfhydryl or carboxyl group on the antibody (e.g., on the epsilon amino group of one or more lysine residues, the free carboxylic acid group of one or more glutamic acid or aspartic acid residues, or to the S atom of one or more cysteinyl residues), or for example a glycan structure of a glycosylated amino acid residue (e.g. a native, truncated or otherwise modified N-glycan bound to Kabat residue N297 of an antibody). An anti-Nectin-4 binding protein functionalized with a linker comprising the structure of Formula VIII or Compounds 5, 6 or 7 will release or yield (e.g. intracellularly, in the presence of Nectin-4 expressing tumor cells) a compound having the structure of Compound 1a.

Formula VIII
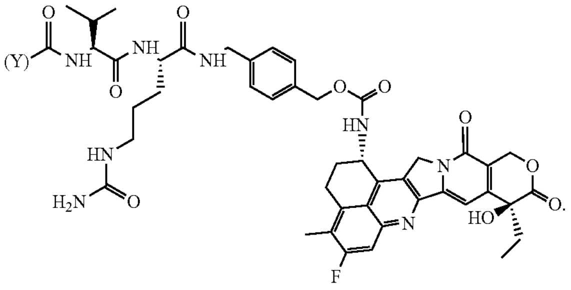
Exemplary linkers having a maleimide as R group can have the structure of Compounds 5, 6 or 7, below. Such linker can be conjugated to an antibody via cysteine residues in the antibody after the interchain disulfide bounds are reduced with a reducing agent.
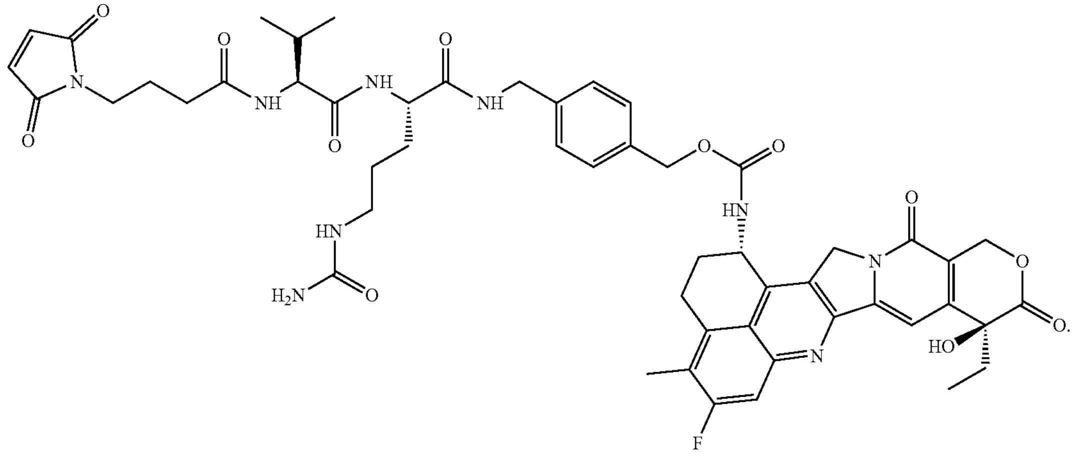
Compound 5 (mal-Val-Cit-PAB-exatecan)
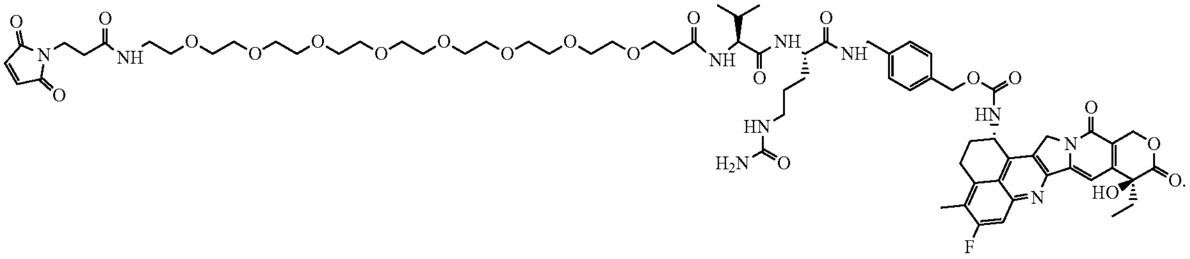
Compound 6 (mal-PEG8-Val-Cit-PAB-exatecan)

-continued

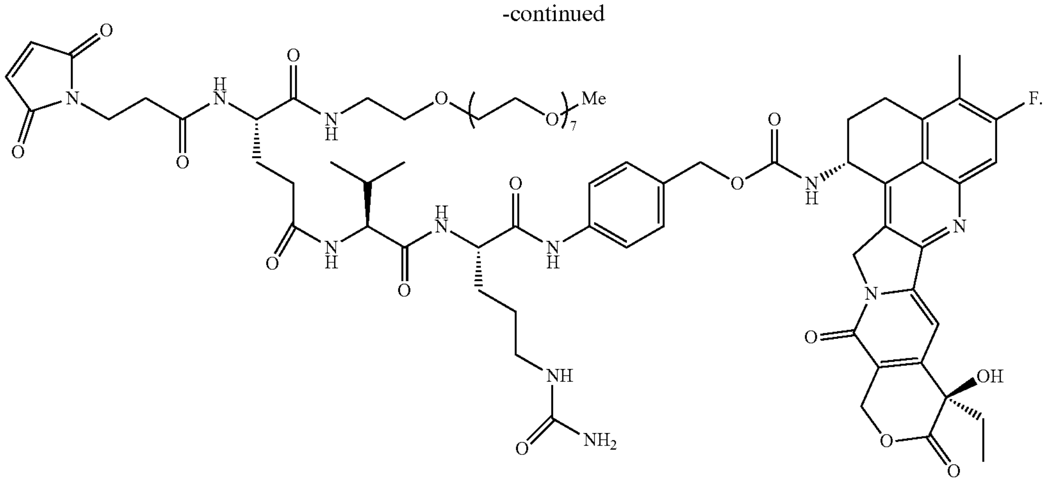

Compound 7 (Mal-Glu-(Val-Cit-PAB-exatecan)-PEG8))

In another embodiment, a linker can have a primary amine as R group, and when reacted with an antibody in the presence of a transglutaminase enzyme, can yield an antibody comprising one or a plurality of acceptor glutamine residues functionalized with the linker. For example, a linker (X—Z), or an antibody functionalized therewith, has or comprises the structure shown as Compound 8, below:

Compound 8

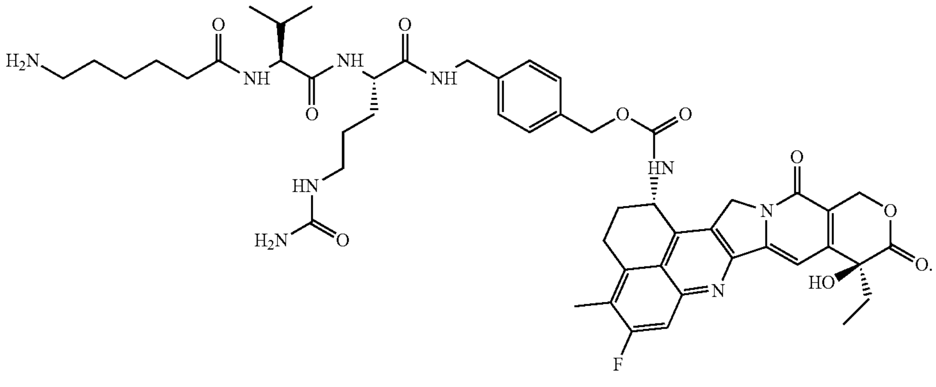

In one embodiment, the linker moiety (X—Z) is or comprises the structure shown in Formula IX, below, wherein (Y) is a spacer comprising (e.g., at its terminus) the residue of the reaction of a reactive group (R) with an amino acid residue, for example a free amino, hydroxyl, sulfhydryl or carboxyl group on the antibody (e.g., on the epsilon amino group of one or more lysine residues, the free carboxylic acid group of one or more glutamic acid or aspartic acid residues, or to the S atom of one or more cysteinyl residues), or for example a glycan structure of a glycosylated amino acid residue (e.g. a native, truncated or otherwise modified N-glycan bound to Kabat residue N297 of an antibody). An anti-Nectin-4 binding protein functionalized with a linker comprising the structure of Formula IX will release (e.g. intracellularly, in the presence of Nectin-4 expressing tumor cells) a compound having the structure of Compound Ia.

Formula IX

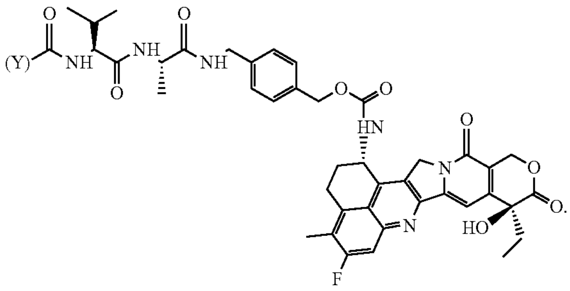

Exemplary linkers having a maleimide as R group can have the structure of Compound 9a, 9b, 9c and 9d, below. Such linkers can be conjugated to an antibody via cysteine residues in the antibody after the interchain disulfide bounds are reduced with a reducing agent.

Compound 9a
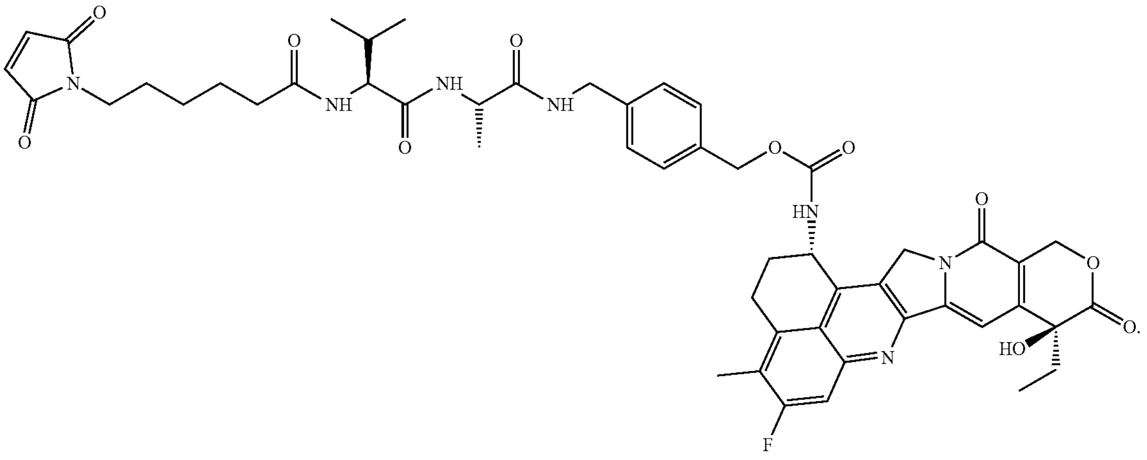
Compound 9b
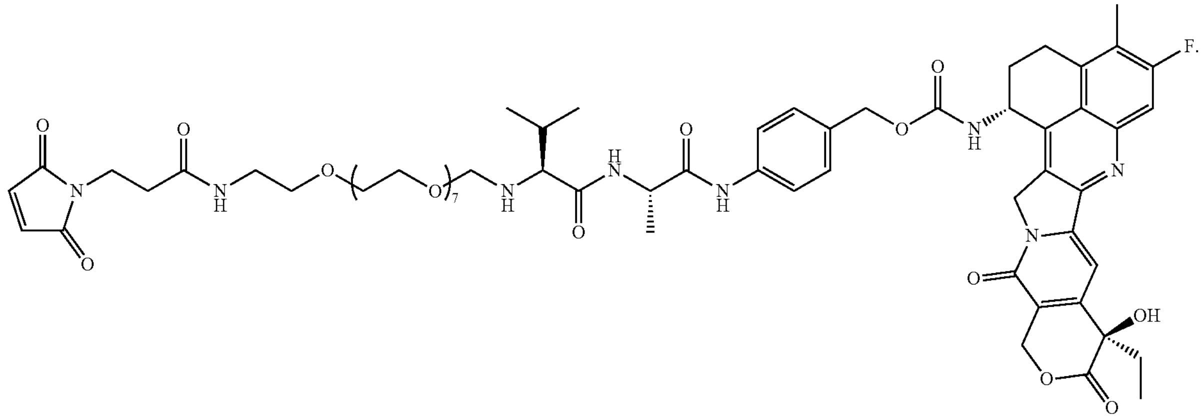
1-Mal-PEG(8u)-Val-Ala-PAB-Exatecan
Compound 9c
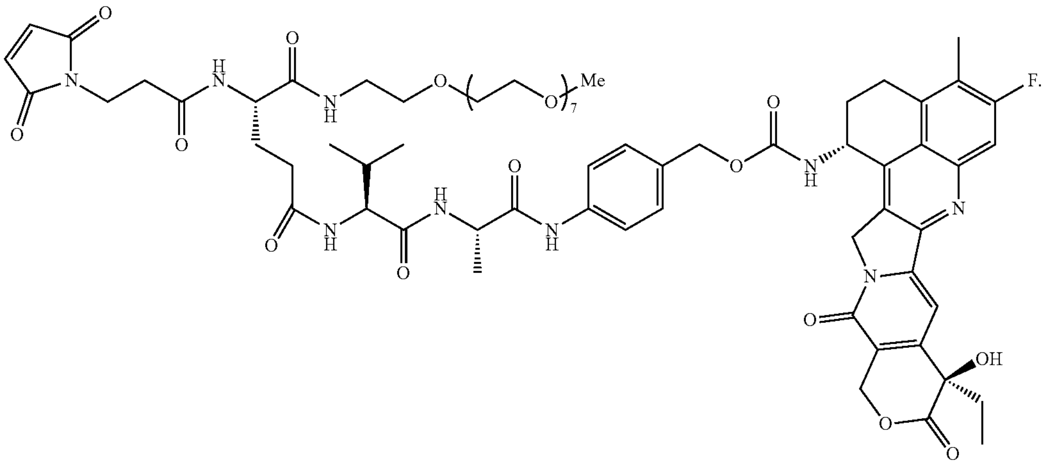
3-Mal-Glu-(Val-Ala-PAB-Exatecan)-PEG(8u)

-continued

Compound 9d

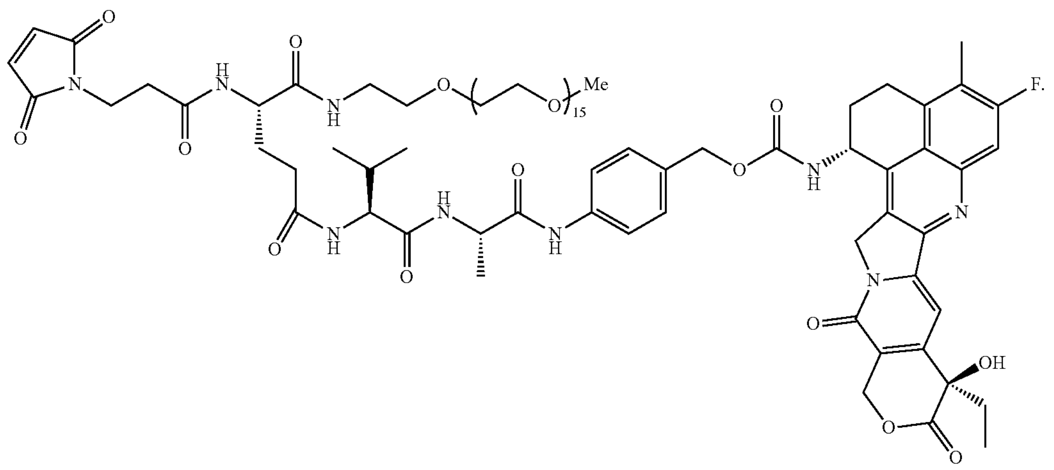

6-Mal-Glu-(Val-Ala-PAB-Exatecan)-PEG(16u)

In another embodiment, a linker can have a primary amine as R group, and when reacted with an antibody in the presence of a transglutaminase enzyme, can yield an antibody comprising one or a plurality of acceptor glutamine residues functionalized with the linker. For example, a linker (X—Z), or an antibody functionalized therewith, has or comprises the structure shown as Compound 10, below:

Compound 10

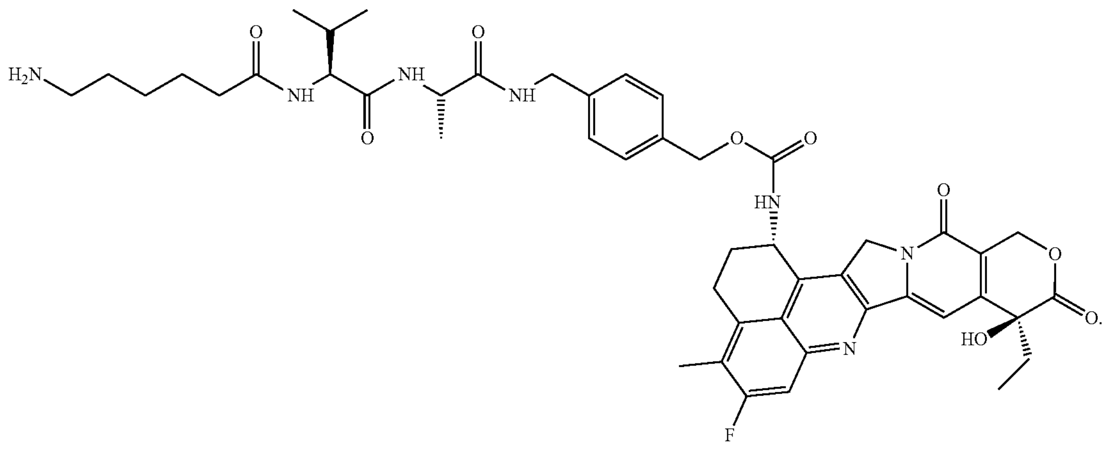

In one embodiment, the linker moiety (X—Z) is or comprises the structure shown in Formula X, below, wherein (Y) is a spacer comprising (e.g., at its terminus) the residue of the reaction of a reactive group (R) with an amino acid residue, for example a free amino, hydroxyl, sulfhydryl or carboxyl group on the antibody (e.g., on the epsilon amino group of one or more lysine residues, the free carboxylic acid group of one or more glutamic acid or aspartic acid residues, or to the S atom of one or more cysteinyl residues), or for example a glycan structure of a glycosylated amino acid residue (e.g. a native, truncated or otherwise modified N-glycan bound to Kabat residue N297 of an antibody).

Formula X

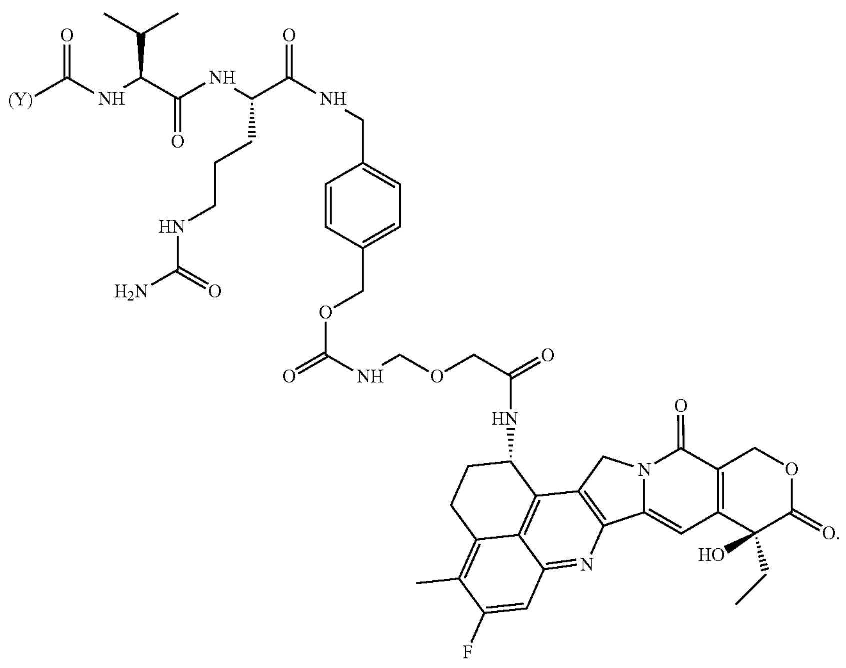

An exemplary linker having a maleimide as R group can have the structure of Compound 11, below. Such linker can be conjugated to an antibody via cysteine residues in the antibody after the interchain disulfide bounds are reduced with a reducing agent, e.g. tris (2-carboxyethyl) phosphine hydrochloride.

wherein (Y) is a spacer comprising (e.g., at its terminus) the residue of the reaction of a reactive group (R) with an amino acid residue, for example a free amino, hydroxyl, sulfhydryl or carboxyl group on the antibody (e.g., on the epsilon amino group of one or more lysine residues, the free carboxylic acid group of one or more glutamic acid or Compound 11

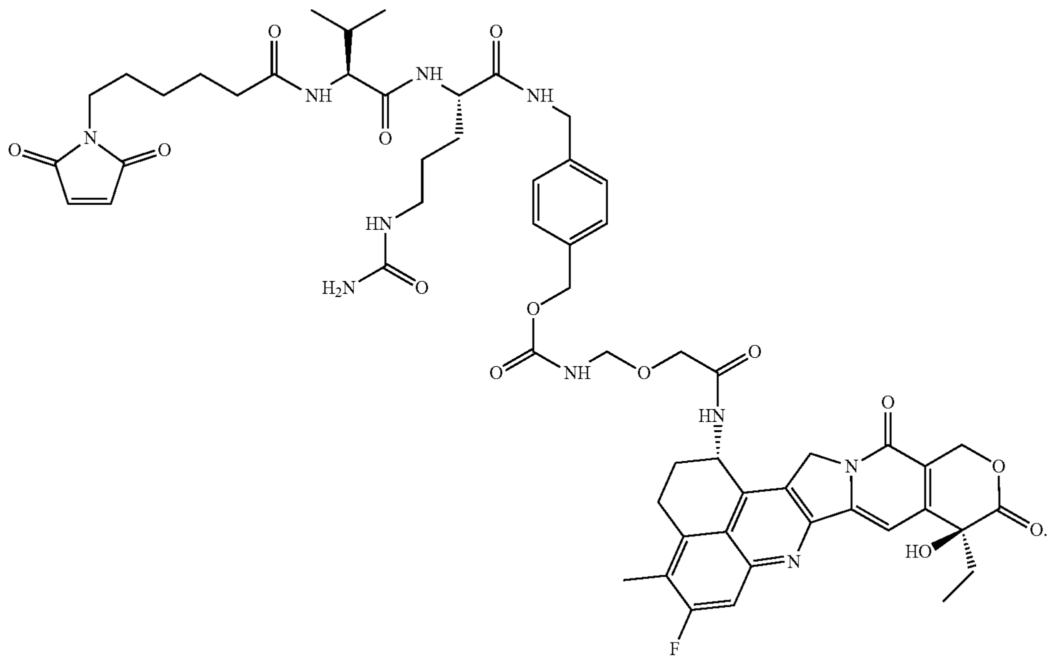

In one embodiment, the linker moiety (X—Z) is or comprises the structure shown in Formula XI, below, aspartic acid residues, or to the S atom of one or more cysteinyl residues), or for example a glycan structure of a glycosylated amino acid residue (e.g. a native, truncated or otherwise modified N-glycan bound to Kabat residue N297 of an antibody).

Formula XI

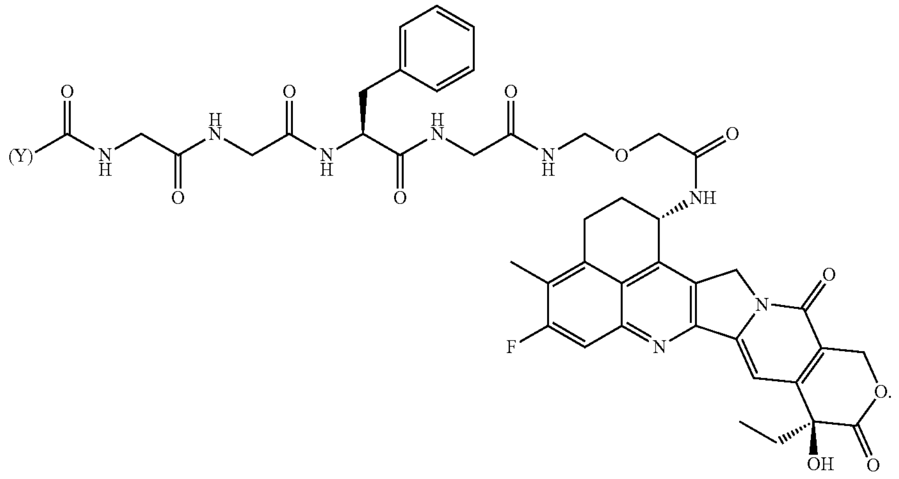

An exemplary linker having a maleimide as R group can have the structure of Compound 12, below. Such linker can be conjugated to an antibody via cysteine residues in the antibody after the interchain disulfide bounds are reduced with a reducing agent.

Compound 12

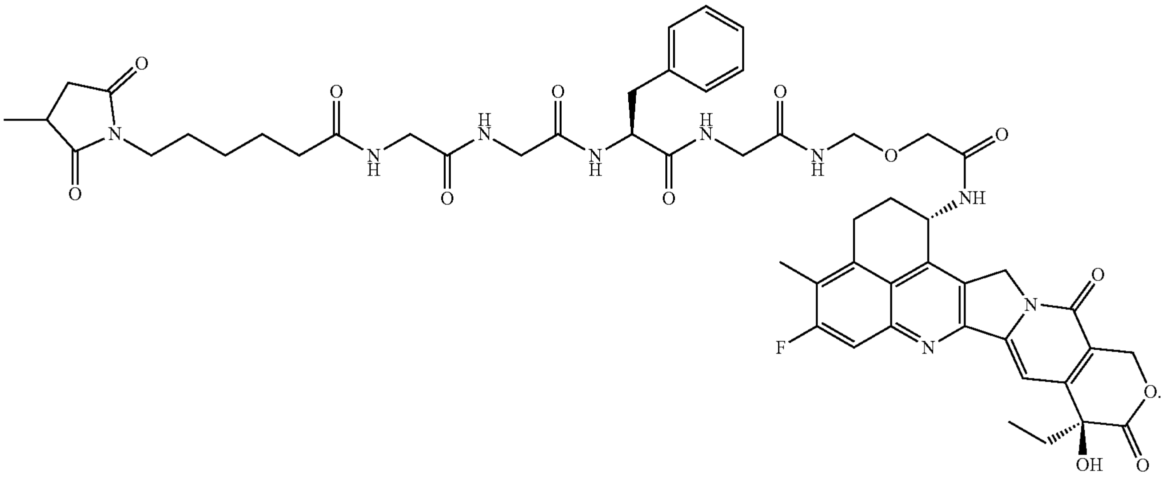

In another embodiment, a linker can have a primary amine as R group, and when reacted with an antibody in the presence of a transglutaminase enzyme, can yield an antibody comprising one or a plurality of acceptor glutamine residues functionalized with the linker. For example, a linker (X—Z), or an antibody functionalized therewith, has or comprises the structure shown as Compound 13, below:

Compound 13

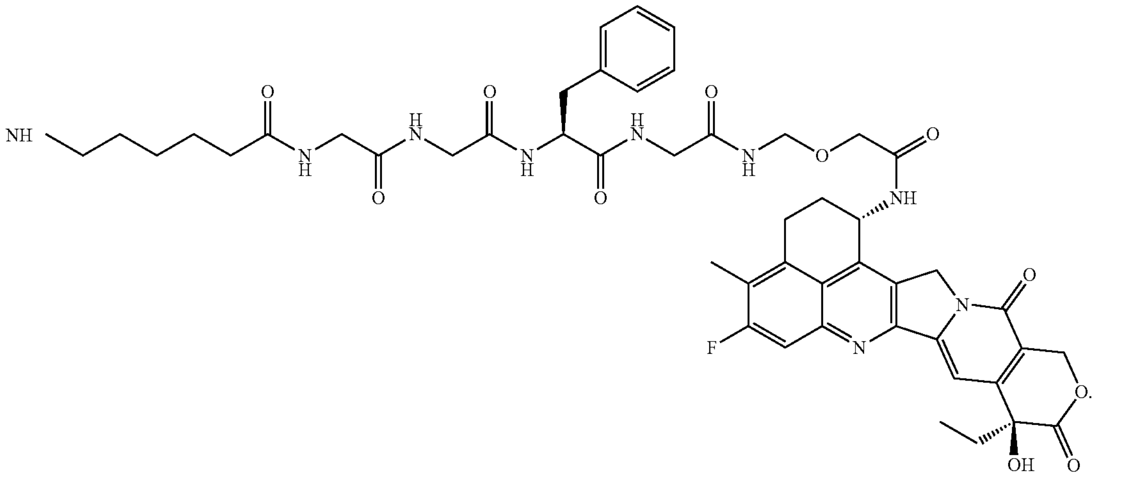

An anti-Nectin-4 binding protein functionalized with an oligopeptide-containing linker of Formulae XI or Compounds 12 and 13 result in the release (e.g. intracellularly, in the presence of Nectin-4 expressing tumor cells) of a substituted exatecan having a OH—$CH_2$—C(═O) substituent present at position 1 amine, as shown in the exatecan-comprising structure below:

Compound 14

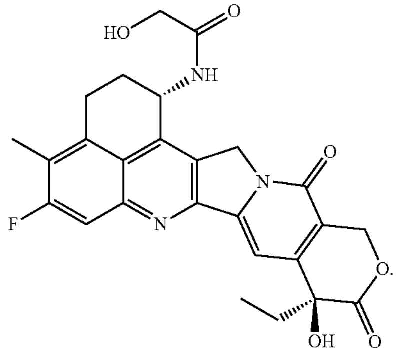

Further examples of suitable linkers shown below in Compounds 15 and 16 have maleimide as R group and phenylalanine-containing peptides attached to a PAB molecule.

Compound 15

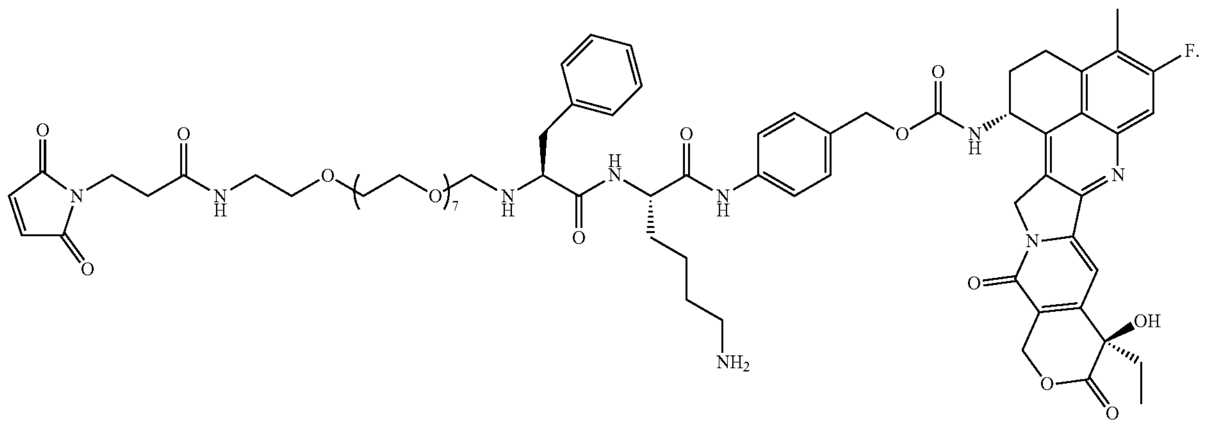

2-Mal-PEG(8u)-Phe-Lys-PAB-Exatecan

Compound 16

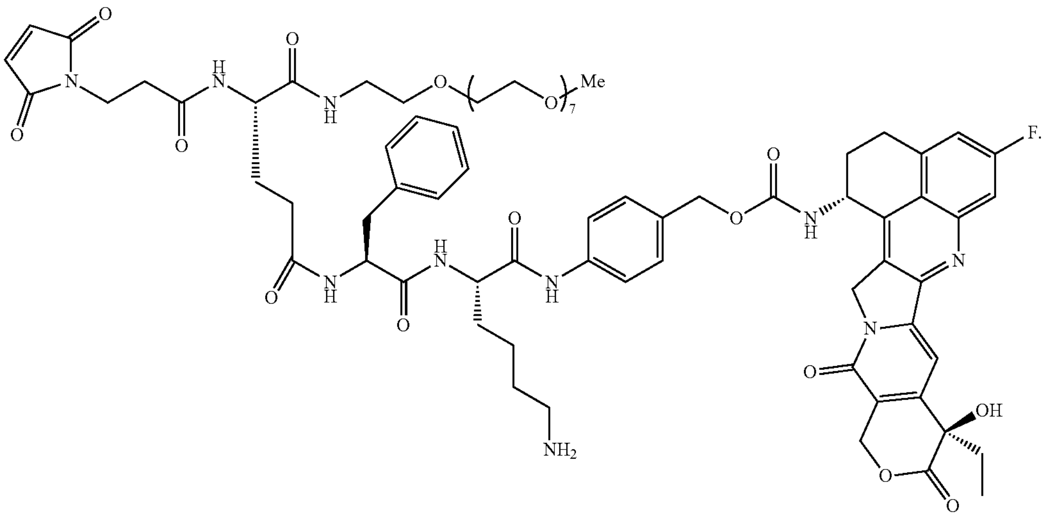

5-Mal-Glu-(Phe-Lys-PAB-Exatecan)-PEG(8u

An exemplary linker having a maleimide as R group and an orthogonal polysarcosine moiety is shown can have the structure of Compound 17, below. Such linker can be conjugated to an antibody via cysteine residues in the antibody after the interchain disulfide bounds are reduced with a reducing agent.

Compound 17

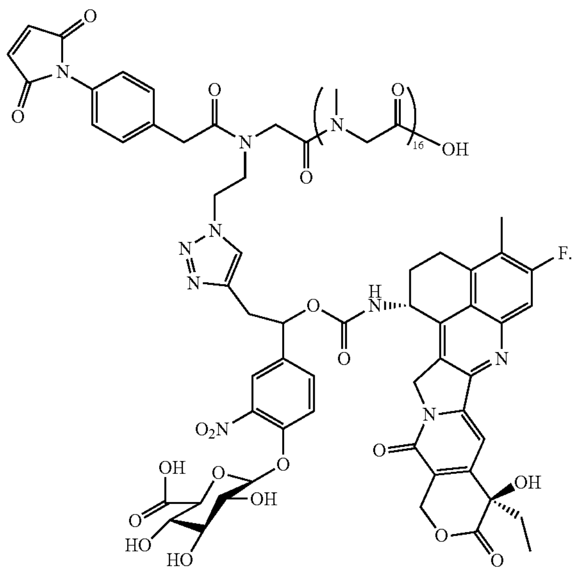

(mal-PSAR16-exatecan)

In any of the exemplary linkers, when bound to an antibody, the reactive group at the terminus can be specified as being replaced by the residue of the reaction of the reactive group with an amino acid residue on the antibody, for example a free amino, hydroxyl, sulfhydryl or carboxyl group of an amino acid.

The exemplary linkers of Formulae III, IV, V, VI, VII, VIII, IX, X or XI when prepared as a structure having a primary amine can reacted with antibody in the presence of a transglutamine enzyme (e.g. Bacterial Transglutaminase, BTG) such that the transglutaminase enzyme catalyzes the conjugation of the linker to an acceptor glutamine residue within the primary structure of the antibody, for example within an immunoglobulin constant domain or within a TGase recognition tag inserted or appended to (e.g., fused to) a constant region. Methods and linkers for use in BTG-mediated conjugation to antibodies is described in PCT publication no. WO2014/202773, the disclosure of which is incorporated by reference. Conjugation catalyzed by BTG permits precise control of the average drug:antibody ratio in a composition. The term "transglutaminase", used interchangeably with "TGase" or "TG", refers to an enzyme capable of cross-linking proteins through an acyl-transfer reaction between the γ-carboxamide group of peptide-bound glutamine and the ε-amino group of a lysine or a structurally related primary amine such as amino pentyl group, e.g. a peptide-bound lysine, resulting in a ε-(γ-glutamyl)lysine isopeptide bond. TGases include, inter alia, bacterial transglutaminase (BTG) such as the enzyme having EC reference EC 2.3.2.13 (protein-glutamine-γ-glutamyl-transferase). The term "acceptor glutamine" residue, when referring to a glutamine residue of an antibody, means a glutamine residue that is recognized by a TGase and can be cross-linked by a TGase through a reaction between the glutamine and a lysine or a structurally related primary amine such as amino pentyl group. Preferably the acceptor glutamine residue is a surface-exposed glutamine residue. The term "TGase recognition tag" refers to a sequence of amino acids comprising an acceptor glutamine residue and that when incorporated into (e.g. appended to) a polypeptide sequence, under suitable conditions, is recognized by a TGase and leads to cross-linking by the TGase through a reaction between an amino acid side chain within the sequence of amino acids and a reaction partner. The recognition tag may be a peptide sequence that is not naturally present in the polypeptide comprising the enzyme recognition tag. Examples of TGase recognition tags include the amino acid sequences: LLQ, LLQG, LSQG, GLLQ, SLLQG, GGGQGGL, LLQGG, LLQGA, LLQGG and LLQGA, or EQKLISEEDL or a variant having one or more (e.g., 2, 3, 4, 5, 6, 7, 8 or 9) sequence modifications.

As exemplified in WO2013/092983 and WO2020/188061, the disclosures of which are incorporate herein by reference, the linker-camptothecin analogue moiety (X—Z) can be conjugated to glutamine residues in an antibody (acceptor glutamines) in two-step process comprising a first step in which a moiety comprising a primary amine and a first reactive group (R) is conjugated to the antibody in the presence of BTG, followed by a step of reacting the antibody-linker conjugate with a molecule comprising (i) a second reactive group (R') that is reactive with the first reactive group and (ii) the camptothecin analogue (Z). Examples of reactive group pairs R and R' include a range of groups capable of biorthogonal reaction, for example 1,3-dipolar cycloaddition between azides and cyclooctynes (copper-free click chemistry), between nitrones and cyclooctynes, oxime/hydrazone formation from aldehydes and ketones and the tetrazine ligation (see also WO2013/092983). The resulting linker and functionalized antibody, or the Y element thereof, can thus comprise a RR' group resulting from the reaction of R and R', for example a triazole.

An anti-Nectin-4 immunoconjugate can be incorporated in a pharmaceutical formulation in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment, the formulation further comprises a pharmaceutically acceptable preservative. In a further embodiment, the formulation further comprises an isotonic agent. In a further embodiment, the formulation also comprises a chelating agent. In a further embodiment of the invention the formulation further comprises a stabilizer. In a further embodiment, the formulation further comprises a surfactant. For convenience reference is made to Remington: *The Science and Practice of Pharmacy,* $19^{th}$ edition, 1995.

It is possible that other ingredients may be present in the pharmaceutical formulation of the present disclosure. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present disclosure.

Administration of pharmaceutical compositions according to the invention may be through several routes of administration, for example, intravenous. Suitable antibody formulations can also be determined by examining experiences with other already developed therapeutic ADCs.

In any embodiment, a composition can be characterized as comprising a plurality of Nectin-4 binding immunoconjugates of the disclosure, wherein at least 70%, 80%, 90%, 95%, 98% or 99% of the immunoconjugates in a sample have at least 4, 6 or 8 amino acid residues per antibody that are functionalized with a linker disclosed herein. In any embodiment, a composition can be characterized as comprising a plurality of Nectin-4 binding immunoconjugates of the disclosure, wherein at least 70%, 80%, 90%, 95%, 98% or 99% of the immunoconjugates in a sample have at least 2, 4, 6 or 8 amino acid residues per antibody that are functionalized with the linker-camptothecin moiety, e.g., the (X—Z) unit or the (—(Y)-(Pep)-(Y')—(Z)) unit of the formulae herein. In any embodiment, a composition can be characterized as comprising a plurality of Nectin-4 binding immunoconjugates of the disclosure, wherein at least 70%, 80%, 90%, 95%, 98% or 99% of the immunoconjugates in a sample have the same number of functionalized amino acid per antibody, optionally wherein the number is 4, 6 or 8.

Diagnostics, Prognostics, and Treatment of Malignancies

In some aspects, described are methods as well as antigen binding proteins (e.g. antibodies, antibody fragments) and immunoconjugates useful in the diagnosis, prognosis, monitoring and treatment of a cancer characterized by tumor cells that express at their surface Nectin-4. In therapeutic uses, the treatment comprises administering to a human subject or individual an antibody camptothecin analogue of the disclosure. The embodiments are methods useful in the diagnosis, prognosis, monitoring and treatment of a Nectin-4 expressing cancer with a Nectin-4 binding agent conjugated to a camptothecin analogue or derivative molecule, e.g. an exatecan or SN-38 molecule. A suitable Nectin-4 binding agent will typically be conjugated to a plurality of molecules of a camptothecin analogue. A camptothecin analogue can be conjugated to the antibody via a linker comprising a protease-cleavable oligopeptide linker. An exemplary pharmaceutical composition can comprise on average from 1 to 8 camptothecin analogue molecules per antibody molecule, optionally from 2-8, from 4-8, from 6-8 camptothecin analogue molecules per antibody molecule, or for example about 4, 5, 6, 7 or 8 camptothecin analogue molecules per antibody molecule.

The Nectin-4 binding agent (e.g. anti-Nectin-4 antibody or antibody fragment) conjugated to a camptothecin analogue can be used advantageously to treat an individual having a Nectin-4-expressing cancer characterized by tumor cells that express Nectin-4 (e.g. at the tumor cell membrane or cell surface). Example of such cancers are urothelial cancer, breast cancer (e.g. triple-negative breast cancer; HER2-positive breast cancer), non-small cell lung cancer, pancreatic cancer, ovarian cancer, gastric cancer, colorectal cancer (e.g. colon cancer), head and neck squamous cell carcinoma and esophageal cancer.

The Nectin-4 binding agent conjugated to a camptothecin analogue can be used in Nectin-4 high-expressing tumors.

The Nectin-4 binding agent conjugated to a camptothecin analogue can also be used in heterogeneous and/or low Nectin-4-expressing tumors. In such tumors, the immunoconjugates of the disclosure can provide advantageous efficacy, optionally via avoidance of MDR1-mediated resistance and/or bystander anti-tumor effects.

The Nectin-4 binding agent conjugated to a camptothecin analogue can be used advantageously to treat an individual regardless of Nectin-4 expression levels, regardless of heterogeneity of Nectin-4 expression levels on tumor cells within an individual, and/or regardless of whether or not the individual has been previously treated with enfortumab verdotin. For example, the Nectin-4 binding agent conjugated to a camptothecin analogue molecule can be used advantageously to treat an individual who has been previously treated with enfortumab verdotin. Such an individual may optionally have a cancer characterized by heterogeneous and/or low Nectin4-expressing tumors following enfortumab verdotin treatment. An individual may have a cancer that is resistant, has not responded, has relapsed and/or progressed despite (e.g. during or following) treatment with an antibody conjugated to an auristatin or MMAE molecule (e.g., enfortumab vedotin). For example, the individual may have a locally advanced or metastatic urothelial cancer and has previously received treatment with an antibody conjugated to an auristatin or MMAE molecule (e.g., enfortumab vedotin).

In advanced recurrent or metastatic urothelial cancer, a significant proportion of individuals will express high levels of Nectin-4 on tumor cells, e.g. H-score of at least 290 (See EV-201 clinical trial Cohort 1 Nectin-4 expression). However, a subset of patients have an H-score of less than 250, and some less than 200. A minority of patient had an H-score of less than 150, with some having an H-score of less than 100. In triple negative breast cancer (TNBC), it has been reported that 62% of patients have high Nectin-4 expression on tumor cells and 38% have low Nectin-4 expression on tumor cells (Rabat et al., 2017 Annals Onc. 28: 769-776). In other cancer types, median H-score values for Nectin-4 expression have typically been lower than that observed in UC, notably in non-small cell lung cancer, pancreatic cancer, ovarian cancer, head and neck squamous cell carcinoma and esophageal cancer.

In one embodiment, an individual treated according to the disclosure has an advanced recurrent or metastatic cancer, optionally an advanced recurrent or metastatic urothelial cancer.

In one embodiment, an individual treated according to the disclosure has a breast cancer that tests positive for estrogen receptors and/or progesterone receptors, and tests negative for epidermal growth factor receptor 2 (HER2) or excess HER2 protein, optionally the cancer test positive for HER2 but HER2 is expressed at low levels.

In one embodiment, an individual treated according to the disclosure has a triple-negative breast cancer (TNBC), e.g., a breast cancer that tests negative for estrogen receptors, progesterone receptors, and excess HER2 protein.

In one embodiment, an individual treated according to the disclosure has a breast cancer that tests positive for HER2 protein, optionally wherein the cancer is expresses excess HER2 protein (HER2 over-expression), optionally the cancer is expresses low levels of HER2 protein (lower than excess HER2 expression). In one embodiment, the individual is treated with an anti-Nectin-4 ADC according to disclosure, in combination with an agent (e.g. antibody) that binds HER2 polypeptides (e.g. trastuzumab, pertuzumab); optionally wherein the antibody that binds HER2 is an ADC; optionally wherein the antibody that binds HER2 is conjugated to a cytotoxic agent, optionally an auristatin, a maytansinoid (e.g. DM1) or a camptothecin analogue (e.g. Compound 1, 2 or 13); optionally wherein the antibody that binds HER2 is trastuzumab emtansine or trastuzumab deruxtecan (DS-8201a).

In one embodiment, an individual treated according to the disclosure has a non-small cell lung cancer, optionally a lung adenocarcinoma.

In one embodiment, an individual treated according to the disclosure has a pancreatic cancer.

In one embodiment, an individual treated according to the disclosure has an ovarian cancer.

In one embodiment, an individual treated according to the disclosure has a head and neck squamous cell carcinoma.

In one embodiment, an individual treated according to the disclosure has an oesophageal cancer.

In one embodiment, an individual treated according to the disclosure has a colorectal cancer. Colorectal cancer (CRC) as used herein refers to colon cancer, rectal cancer, and colorectal cancer (cancer of both the colon and rectal areas).

In one embodiment, an individual treated according to the disclosure has a NSCLC or lung adenocarcinoma, a gastric cancer, a colorectal carcinoma, a pancreatic cancer, a urothelial carcinoma or bladder cancer that tests positive for HER2 protein, optionally wherein the cancer expresses excess HER2 protein (HER2 over-expression), optionally the cancer is expresses low levels of HER2 protein (lower than excess HER2 expression). In one embodiment, the individual is treated with an anti-Nectin-4 ADC according to disclosure, in combination with an agent (e.g. antibody) that binds Her2 polypeptides (e.g. an antibody comprising the heavy and light chains CDRs or variable regions of trastuzumab or pertuzumab); optionally wherein the antibody that binds Her2 is an ADC; optionally wherein the antibody that binds Her2 is conjugated to a cytotoxic agent, optionally an auristatin, a maytansinoid (e.g. DM1) or a camptothecin analogue (e.g. Compound 1, 2 or 14); optionally wherein the antibody that binds Her2 is trastuzumab emtansine or trastuzumab deruxtecan (DS-8201a).

In one aspect, the treatment methods of the disclosure are independent of the assessment or detection of Nectin-4 expression in tumor tissue and/or independent of the expression level of Nectin-4 on tumor cells and/or the frequency or number of Nectin-4-expressing tumor cells in a tissue sample from said individual.

In one aspect, the present disclosure provides methods of treating a cancer and/or eliciting an anti-tumor immune response in an individual in need thereof, wherein said individual has advanced recurrent or metastatic urothelial cancer or breast cancer (e.g. TNBC), wherein said methods do not necessitate the pre-determination of whether the individual has tumor tissue comprising cells (e.g. tumor cells) that express Nectin-4 or not.

In one aspect, the present disclosure provides methods of treating a cancer and/or killing tumor cells in an individual in need thereof, wherein said individual has advanced recurrent or metastatic urothelial cancer or breast cancer (e.g. TNBC), wherein said methods do not necessitate the predetermination of whether or not the individual has tumor tissue comprising cells (e.g. tumor cells) that express high-levels of Nectin-4, e.g. as defined by an immunohistochemistry assessment (e.g. an H-score or other appropriate IHC scoring method).

In one aspect, the methods of treating a cancer and/or killing tumor cells in an individual do not necessitate the pre-determination of the level of Nectin-4 expression of tumor cells.

In one aspect, the methods of treating a cancer in an individual, optionally an advanced recurrent or metastatic urothelial cancer or a breast cancer (e.g. TNBC, HER2 positive cancer), comprise treating an individual having a cancer characterized by an H-score for Nectin-4 expression of no more than, or less than, 290, 250, 200, 150 or 100.

In any embodiment for treating or preventing a cancer in an individual, the method can be specified as comprising the steps of: (i) identifying an individual whose tumor cells express Nectin-4 (e.g. as determined by immunohistochemistry), and (ii) administering to the individual an effective amount of an anti-Nectin-4 antibody camptothecin analoguedrug conjugate of the disclosure.

In any embodiment for treating or preventing a cancer in an individual, the method can be specified as comprising the steps of (i) identifying an individual whose tumor cells express (a) Nectin-4 (e.g. as determined by immunohistochemistry), and (b) HER2, optionally wherein the tumor cells express low levels of HER2 (e.g. as determined by immunohistochemistry; as determined by Herceptest™) and (ii) administering to the individual an effective amount of an anti-Nectin-4 antibody conjugated to a camptothecin analogue or derivative molecule, optionally in combination with an agent (e.g. antibody) that binds Her2 polypeptides (e.g. trastuzumab, pertuzumab); optionally wherein the antibody that binds Her2 is an ADC; optionally wherein the antibody that binds Her2 is conjugated to a cytotoxic agent, optionally an auristatin, a maytansinoid (e.g. DM1) or a camptothecin analogue (e.g. Compound 1, 2 or 14); optionally wherein the antibody that binds Her2 is trastuzumab emtansine or trastuzumab deruxtecan (DS-8201a).

In any embodiment for treating or preventing a cancer in an individual, the method can be specified as comprising the steps of: (i) identifying an individual whose tumor cells have a low or moderate level of Nectin-4 expression (e.g. as determined by immunohistochemistry), and (ii) administering, to the individual identified in step (i), an effective amount of an anti-Nectin-4 antibody conjugated to a camptothecin analogue or derivative molecule.

In any embodiment for treating or preventing a cancer (e.g. a Nectin-4 positive cancer) in an individual, the method can be specified as comprising the steps of: (i) identifying an individual whose cancer is characterized by a low level of Nectin-4 expression (e.g. as determined by immunohistochemistry), and (ii) administering, to the individual identified in step (i), an effective amount of an anti-Nectin-4 antibody camptothecin analoguedrug conjugate of the disclosure. In one embodiment, the individual has a cancer characterized by an H-score for Nectin-4 expression of no more than, or less than, 150 or 100.

In any embodiment for treating or preventing a cancer (e.g. a Nectin-4 positive cancer) in an individual, the method can be specified as comprising the steps of: (i) identifying an individual whose cancer is characterized by a moderate level of tumor Nectin-4 expression (e.g. as determined by immunohistochemistry), and (ii) administering to the individual an effective amount of an anti-Nectin-4 antibody camptothecin analoguedrug conjugate of the disclosure. In one embodiment, the individual has a cancer characterized by an H-score by an H-score for Nectin-4 expression of no more than, or less than, 290, 250, 200, 150, optionally further wherein the cancer is characterized by an H-score for Nectin-4 expression of at least 100.

In a still further embodiment, provided is a method for treating or preventing a cancer (e.g. a Nectin-4 positive cancer) in an individual comprising: (i) identifying an individual whose cancer is characterized by an H-score for tumor Nectin-4 expression of no more than, or less than, 290, 250, 200, 150, 120 or 100, and (ii) administering to the individual an effective amount of an anti-Nectin-4 antibody camptothecin analoguedrug conjugate of the disclosure. Optionally, step (i) may be specified as comprising a step of assessing Nectin-4 expression on tumor cells by histochemistry (e.g. IHC).

In a still further embodiment, provided is a method for treating or preventing a cancer (e.g. a Nectin-4 positive cancer; a breast cancer) in an individual comprising: (i) identifying an individual whose cancer is characterized by a QS-score for tumor Nectin-4 expression of no more than, or less than, 200, 150, 120 or 100, and (ii) administering to the individual an effective amount of an anti-Nectin-4 antibody camptothecin analoguedrug conjugate of the disclosure. Optionally, step (i) may be specified as comprising a step of assessing Nectin-4 expression on tumor cells by histochemistry (e.g. IHC).

A biological sample from an individual, for example from a biopsy, can be obtained and assessed. Optionally, the sample is preserved as formaldehyde (e.g. formalin)-fixed paraffin embedded (FFPE) samples. Following deparaffination, the slides are amenable to methods to detect the expression of Nectin-4 (and/or HER2).

Expression of Nectin-4 and/or HER2 in tumor cells can be determined by any methods known in the art. In certain embodiments, assays include immunohistochemistry (IHC) assays, fluorescence activated cell sorting (FACS) assays, for example quantitative FACS, ELISA, immunoblotting (e.g. western blotting, dot blotting, or in-cell western blotting), and other immunoassays.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, in some embodiments, polyclonal antisera, and in some embodiments, monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

In some embodiments, the IHC assay is a direct assay, wherein binding of antibody to the target antigen is determined directly. This direct assay uses a labeled reagent, such as a fluorescent tag or an enzyme-labeled primary antibody, which can be visualized without further antibody interaction. In some embodiments, the IHC assay is an indirect assay. In a typical indirect assay, unconjugated primary antibody binds to the antigen and then a labeled secondary antibody binds to the primary antibody. Where the secondary antibody is conjugated to an enzymatic label, a chromagenic or fluorogenic substrate is added to provide visualization of the antigen. Signal amplification occurs because several secondary antibodies may react with different epitopes on the primary antibody. The primary and/or secondary antibody used for immunohistochemistry typically will be labeled with a detectable molecule. Numerous labels are available, including radioisotopes, colloidal gold particles, fluorescent labels, and enzyme-substrate labels.

Strongly staining, moderately staining, and weakly staining are descriptions well known to those in the art. In some aspects strongly staining, moderately staining, and weakly staining are calibrated levels of staining, wherein a range is established and the intensity of staining is binned within the range. In some embodiments, strong staining is staining above the 75th percentile of the intensity range, moderate staining is staining from the 25th to the 75th percentile of the intensity range, and low staining is staining is staining below the 25th percentile of the intensity range. In some aspects one skilled in the art, and familiar with a particular staining technique, adjusts the bin size and defines the staining categories.

Control cell lines (e.g., centrifuged into a pellet and formalin fixed and paraffin embedded, e.g., and prepared as a tissue microarray, and e.g., stained with anti-Nectin-4 antibodies) with various staining intensities (e.g., when stained with anti-Nectin-4 antibodies) may be utilized as controls for IHC analysis. One of ordinary skill understands that other control cell pellets with negative, weak, moderate and high c-met staining intensity may readily be identified using the teachings of the present application and methods well known in the art and disclosed herein.

In some embodiments, a cancer or tumor is considered to be a Nectin-4-expressing cancer tumor when it is (e.g. is determined to be using an IHC assay) Nectin-4 positive. In some embodiments, an individual's cancer or tumor is Nectin-4 positive when 5% or more of the tumor cells in the sample express Nectin-4 protein (e.g., express Nectin-4 protein at any intensity). In some embodiments, an individual's cancer or tumor is Nectin-4 positive when 10% or more of the tumor cells in the sample express Nectin-4 protein (e.g., express Nectin-4 protein at any intensity). In some embodiments, an individual's cancer or tumor is Nectin-4 positive when 20% or more of the tumor cells in the sample express Nectin-4 protein (e.g., express Nectin-4 protein at any intensity). In some embodiments, an individual's cancer or tumor is Nectin-4 positive when 30% or more of the tumor cells in the sample express Nectin-4 protein (e.g., express Nectin-4 protein at any intensity). In some embodiments, an individual's cancer or tumor is Nectin-4 positive when 40% or more of the tumor cells in the sample express Nectin-4 protein (e.g., express Nectin-4 protein at any intensity). In some embodiments, an individual's cancer or tumor is Nectin-4 positive when 50% or more of the tumor cells in the sample express Nectin-4 protein (e.g., express Nectin-4 protein at any intensity). In some embodiments, an individual's cancer or tumor is Nectin-4 positive when 60% or more of the tumor cells in the sample express Nectin-4 protein (e.g., express Nectin-4 protein at any intensity). In some embodiments, an individual's cancer or tumor is Nectin-4 positive when 70% or more of the tumor cells in the sample express Nectin-4 protein (e.g., express Nectin-4 protein at any intensity). In some embodiments, an individual's cancer or tumor is Nectin-4 positive when 80% or more of the tumor cells in the sample express Nectin-4 protein (e.g., express Nectin-4 protein at any intensity). In some embodiments, an individual's cancer or tumor is Nectin-4 positive when 90% or more of the tumor cells in the sample express Nectin-4 protein (e.g., express Nectin-4 protein at any intensity).

In some embodiments, an individual's cancer or tumor is Nectin-4 positive when 5% or more of the tumor cells in the sample express Nectin-4 protein with a moderate and/or strong staining intensity. In some embodiments, an individual's cancer or tumor is Nectin-4 positive when 10% or more of the tumor cells in the sample express Nectin-4 protein with a moderate and/or strong staining intensity. In some embodiments, an individual's cancer or tumor is Nectin-4 positive when 20% or more of the tumor cells in the sample express Nectin-4 protein with a moderate and/or strong staining intensity. In some embodiments, an individual's cancer or tumor is Nectin-4 positive when 30% or more of the tumor cells in the sample express Nectin-4 protein with a moderate and/or strong staining intensity. In some embodiments, an individual's cancer or tumor is Nectin-4 positive when 40% or more of the tumor cells in the sample express Nectin-4 protein with a moderate and/or strong staining intensity. In some embodiments, an individual's cancer or tumor is Nectin-4 positive when 50% or more of the tumor cells in the sample express Nectin-4 protein with a moderate and/or strong staining intensity. In some embodiments, an individual's cancer or tumor is Nectin-4 positive when 60% or more of the tumor cells in the sample express Nectin-4 protein with a moderate and/or strong staining intensity. In some embodiments, an individual's cancer or tumor is Nectin-4 positive when 70% or more of the tumor cells in the sample express Nectin-4 protein with a moderate and/or strong staining intensity. In some embodiments, an individual's cancer or tumor is Nectin-4 positive when 80% or more of the tumor cells in the sample express Nectin-4 protein with a moderate and/or strong staining intensity. In some embodiments, an individual's cancer or tumor is Nectin-4 positive when 90% or more of the tumor cells in the sample express Nectin-4 protein with a moderate and/or strong staining intensity.

Assessing immunohistochemistry assays in order to determine whether an individual's cancer or tumor is characterized by high Nectin-4 expression or not (e.g. low or moderate Nectin-4 expression) will typically involve application of a known scoring method.

Low, moderate and high tumor Nectin-4 expression can be determined based on an "H-score" as described in US Pat. Pub. No. 2013/0005678. An H-score is obtained by the formula: (3× percentage of strongly staining cells)+(2× percentage of moderately staining cells)+(percentage of weakly staining cells), giving a range of 0 to 300. H-score has been used in particular in UC.

In some embodiments of any of the methods herein, low or moderate Nectin-4 expression (e.g., tumors or tumor cells having a low or moderate level of Nectin-4 expression) corresponds to an H-score of about 250 or lower, about 220 or lower, about 200 or lower, about 180 or lower, about 160 or lower, about 150 or lower, about 140 or lower, about 130 or lower, about 120 or lower, about 110 or lower or about 100 or lower.

In some embodiments of any of the methods herein, low Nectin-4 expression (e.g., tumors or tumor cells having a low level of Nectin-4 expression) corresponds to an H-score of 200 or lower, about 180 or lower, about 160 or lower, about 150 or lower, about 140 or lower, about 130 or lower, about 120 or lower, about 110 or lower or about 100 or lower.

In some embodiments of any of the methods herein, high Nectin-4 expression (e.g. tumors or tumor cells having a high level of Nectin-4 expression) corresponds to an H-score of about 290 or higher.

In another example, Nectin-4 staining can be scored according to the Quick score (QS) by using the following formula: QS=P (percentage of positive cells)×I (intensity), the maximum score being 300. QS has been used for example in breast cancer. For example, in TNBC some research groups have defined low Nectin-4 expression group as a QS= or <100. In some embodiments of any of the methods herein, low or moderate Nectin-4 expression (e.g., tumors or tumor cells having a low or moderate level of Nectin-4 expression) corresponds to QS-score of about 200 or lower, about 180 or lower, about 160 or lower, about 150 or lower, about 140 or lower, about 130 or lower, about 120 or lower, about 110 or lower or about 100 or lower.

Assays for assessing tumor cell expression of HER2 are well-known in the art. For example, assays such as the FDA-approved SPoT-Light HER2 CISH can be used to detect HER2 over-expression. Chromogenic in situ hybridization (CISH) detects HER2 gene amplification. This technique, also referred to as Subtraction Probe Technology Chromogenic In Situ Hybridization, is a test used see if breast cancer cells overexpress HER2 receptor proteins at the cell surface.

Another widely used assay for HER2 is the HercepTest™ (Dako North America, Inc.), a semiquantitative immunohistochemical assay used to determine HER2 protein overexpression in in formalin-fixed, paraffin-embedded cancer tissue. For example, tumors expressing low levels of HER2 can be identified by a score of +1 to +2 via HercepTest™.

In one aspect, the treatment is used in an individual who has existing neuropathy, diabetes or hyperglycemia, cardiac insufficiency, an ocular pathology. Such conditions can render the individual unsuitable for treatment with anti-Nectin-4 ADCs such as enfortumab verdotin having higher toxicity or a more narrow therapeutic window than the anti-Nectin-4 antibody drug conjugates of the disclosure.

In any embodiment, the method of treatment may optionally comprise the steps of (a) assessing the cancer stage and/or disease progression in the individual; and (b) if the individual has recurrent, metastatic and/or progressing cancer, administering to the individual an effective amount of an anti-Nectin-4 antibody conjugated to a camptothecin analogue or derivative molecule.

In some embodiments, the invention includes a method of treating a tumor in an individual having a urothelial cancer, comprising: (a) assessing the cancer stage and/or disease progression in the individual; and (b) if the individual has recurrent, metastatic and/or progressing cancer, administering to the individual an effective amount of an anti-Nectin-4 antibody conjugated to an exatecan molecule.

Optionally, an individual may have a cancer (e.g., a urothelial cancer, breast cancer (e.g. triple-negative breast cancer; HER2-positive cancer), non-small cell lung cancer, pancreatic cancer, ovarian cancer, gastric cancer, colorectal cancer, head and neck squamous cell carcinoma or esophageal cancer) that is resistant, has not responded, or has relapsed and/or progressed despite (e.g. during or following) surgery and/or treatment with a therapeutic agent, e.g. a chemotherapeutic agent, an antibody, an ADC or radiotherapy.

In any embodiment herein, treatment response can be defined and/or assessed according to well-known criteria, e.g. Response Evaluation Criteria In Solid Tumors (RECIST), such as version 1.1, see Eisenhauer et al. (2009) Eur. J. Cancer 45:228-247, or Immune-Related Response Criteria (irRC), see Wolchock et al. (2009) Clinical Cancer Research 15:7412-7420.

Optionally, an individual treated with an anti-Nectin-4 antibody drug conjugate of the disclosure has a tumor or cancer that displays resistance, that is not responsive to or that has progressed following treatment with a chemotherapeutic agent (e.g. a chemotherapeutic agent known to be capable of being transported by P-glycoprotein (Pgp), for example anthracyclines (doxorubicin, daunorubicin, taxanes (paclitaxel, docetaxel), Vinca alkaloids (vincristine, vinblastine, vindesine), and etoposides. Compounds recognized by Pgp are typically characterized as modestly hydrophobic (octanol-to-water partitioning coefficient, log P>1), often contain titratable protons with a net cationic charge under physiological conditions, and are predominately "natural products" with an aromatic moiety.

In some embodiments, an ADC comprising an anti-Nectin-4 antibody, antibody fragment is used or administered in the absence of combined administration of a chemotherapeutic agent. Optionally, the individual can be characterized as having cancer which has progressed, relapsed or not responded to prior treatment with a prior therapy, optionally further wherein the prior therapy comprises administration of enfortumab verdotin and/or administration of a PD-1 neutralizing agent (e.g., pembrolizumab, atezolizumab, nivolumab), optionally wherein the prior therapy is a chemotherapeutic agent.

Optionally, in any embodiment, the individual can be characterized being ineligible for treatment with enfortumab verdotin, and/or as having cancer which is not suitable or indicated for treatment with enfortumab verdotin.

Exemplary treatment protocols for treating a human with an anti-Nectin-4 antibody conjugated to an camptothecin analogue molecule include, for example, administering to the patient an effective amount of an anti-Nectin-4 antibody conjugated to an camptothecin analogue molecule, wherein the method comprises at least one administration cycle in which at least one dose of the anti-Nectin-4 antibody conjugated to a camptothecin analogue molecule is administered at a dose of 0.1-10 mg/kg body weight, 0.1-5 mg/kg body weight, 0.1-1 mg/kg body weight, 1-10 mg/kg body weight or 1-5 mg/kg body weight. In one embodiment, a plurality of doses are administered, e.g. at least 2, 3, 4, 5, 6, 8, 10 doses. In one embodiment, administration of doses are separated by at least 2, 3 or 4 weeks. In one embodiment, the administration cycle is between 2 weeks and 8 weeks, or is at least 4, 6, 8 or 16 weeks.

In one embodiment the anti-Nectin-4 antibody conjugated to a camptothecin analogue molecule is administered by i.v.

EXAMPLES

Example 1: Human Tumor Cells Co-Expressing Her2 and Nectin-4

A study of HER2 and Nectin-4 gene expression study was carried out using The Cancer Genome Atlas (a collaboration between the National Cancer Institute and National Human Genome Research Institute) based on multi-dimensional maps of the key genomic changes in different types of cancer. Significant correlations of HER2 and Nectin-4 expression was observed in particular in samples from pancreatic cancer patients, lung adenocarcinoma patients, breast cancer and bladder cancer. The highest correlation observed was pancreatic cancer, with correlation values: Spearman 0.71 and Pearson 0.78.

HER2 and Nectin-4 expression on SUM185 and SUM190 human breast cancer tumor cell lines (Biovit inc.) was determined by flow cytometry. SUM185 originates from a pleural effusion of a patient with ER negative. PR negative and Her2 positive anaplastic carcinoma of the breast. The cell line over expresses Her2. SUM190 originates from a primary tumor from a patient with ER negative. PR negative and Her2 positive (amplified) breast cancer. Tumor cells were stained with anti-Nectin-4 antibody (ASG-22ME modified as a human IgG1 isotype containing a N297Q mutation having reduced Fc gamma receptor binding) or Anti-Her2 antibody (trastuzumab modified as human IgG1 isotype containing a N297Q mutation reduced Fc gamma receptor binding), as well as isotype control, at 10 μg/ml (15 min. at 4° C.), followed by PE conjugated polyclonal goat anti human antibodies at a dilution of 1:200. Samples were analyzed by cytofluorometric analysis with Canto II (HTS).

Figure 2:
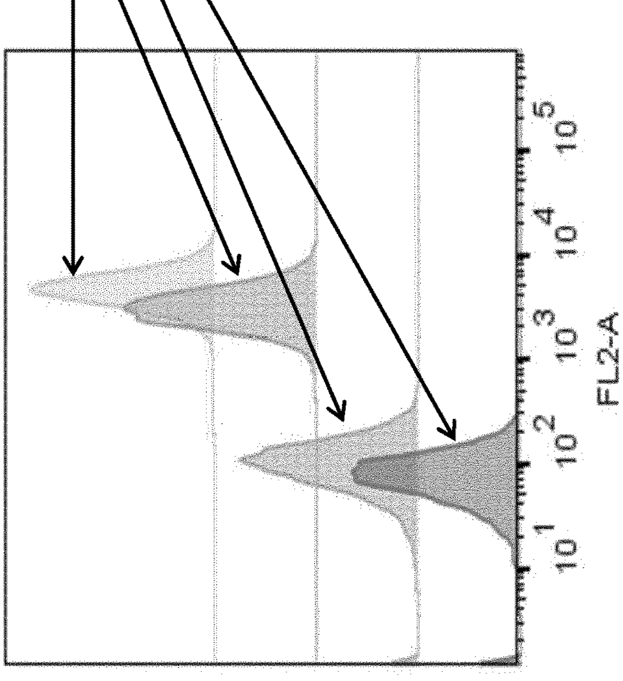
FIG. 2 shows expression levels of HER2 and Nectin-4 polypeptides at the surface of SUM185 human breast cancer tumor cells as determined by FACS (MFI:Mean of fluorescence intensity). The SUM185 cells expressed HER2 at moderate to high levels (median fluorescence units 2880) as well as Nectin-4 at higher levels (median 4326 fluorescence units).

Representative results are shown in FIG. 1 for SUM190 human breast cancer tumor cells and in FIG. 2 for SUM185 human breast cancer tumor cells. MFI:Mean of fluorescence intensity. The SUM190 tumor cells expressed HER2 at low to moderate levels (median fluorescence units 1777) as well as Nectin-4 at lower levels (median 991 fluorescence units). The SUM185 cells expressed HER2 at moderate to high levels (median fluorescence units 2880) as well as Nectin-4 at higher levels (median 4326 fluorescence units).

| | HER2 (MFI) | Nectin-4 (MFI) |
|---|---|---|
| SUM185 | 2880 | 4326 |
| SUM190 | 1777 | 991 |

Example 2: Efficacy of Anti-Nectin-4 ADCs Functionalized with Camptothecin Analogues on HER2+ Nectin4+ Human Tumor Cells Anti-Nectin-4 antibody-drug conjugates were prepared and compared to trastuzumab antibody-drug conjugates for efficacy on HER2+ Nectin4+ human tumor cells. The anti-Nectin-4 antibody-drug conjugates were prepared having the VH and VL of SEQ ID NOS: 9 and 10 as human IgG1 isotype. Anti-Her2 antibody-drug conjugates were prepared having the heavy and light chains of trastuzumab (human IgG1 isotype). Both the anti-Nectin-4 and the anti-Her antibodies were each conjugated stochastically to a linker-camptothecin analogue via cysteine residues in the antibody after partial reduction of interchain disulfide. A range of 2-10 molar equivalents of reducing agent tris (2-carboxyethyl) phosphine hydrochloride was incubated with antibody (3 mg/mL) for 2 h under agitation (350-400 rpm, +37° C.) to reduce disulfides. Conjugation of the linker-toxin was carried out by addition of a molar excess of linker-toxin at 9.2 or 12 molar equivalents incubated overnight on a stirring wheel at +37° C. The resulting ADCs had an average drug loading (drug:antibody ratio) of about 8. In a further example, anti-Nectin-4 antibodies were also conjugated to a second camptothecin (SN-38) containing linker using the same methods. The ADCs used in this Example are as follows.
N4 ADC1: Anti-Nectin-4 conjugated to a linker having the structure:
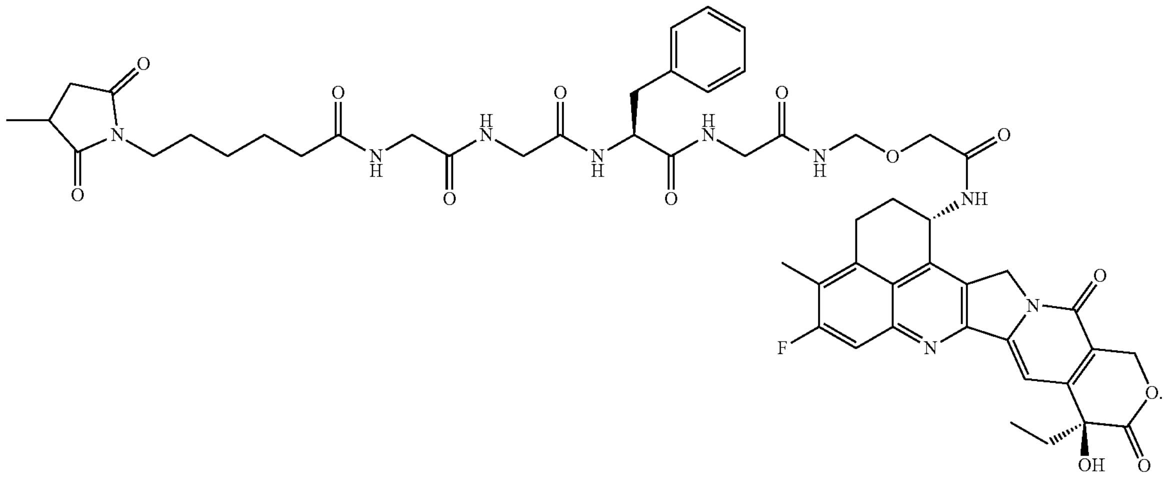 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)CC(C)C1=O)CC3]
Her2 ADC1: Anti-Her2 conjugated to a linker having the structure:
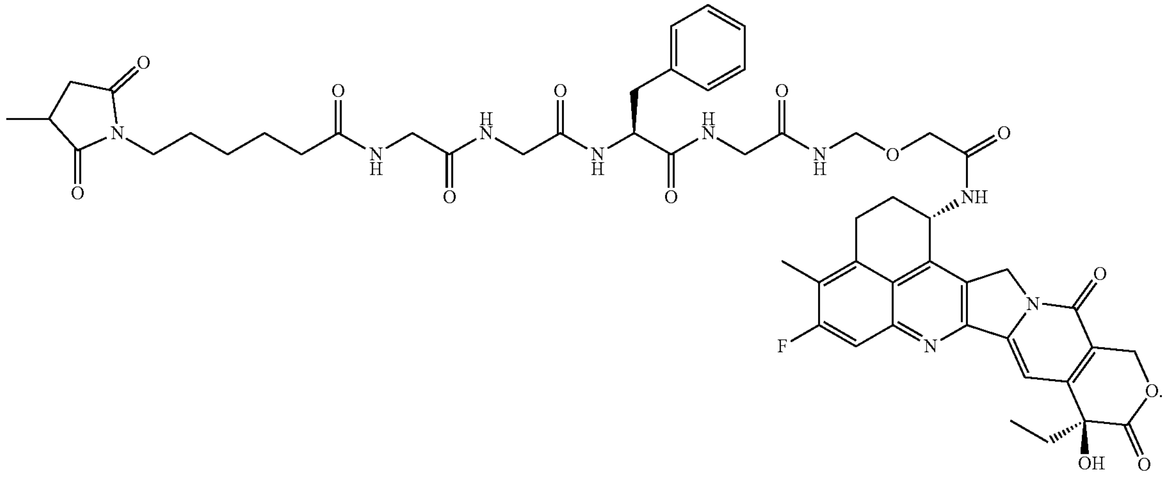 [SMILES: CC[C@@]1(O)C(=O)OCc2c1cc1n(c2=O)Cc2c-1nc1cc(F)c(C)c3c1c2[C@@H](NC(=O)COCNC(=O)CNC(=O)[C@H](Cc1ccccc1)NC(=O)CNC(=O)CNC(=O)CCCCCN1C(=O)CC(C)C1=O)CC3]
N4 ADC2: Anti-Nectin-4 conjugated to a linker having the structure:

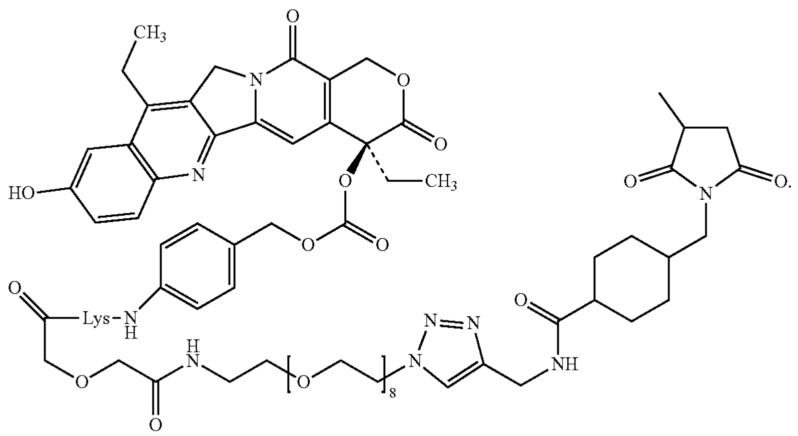

The resulting ADCs were tested for their ability to induce death of Nectin-4/Her2 expressing SUM190 and SUM185 tumor cells of Example 1. Briefly, cells were plated cells in 96 well plates (V=80 μl). N4 ADC1 and Her2 ADC1 or human IgG1-isotype control (IC)-linker-toxin or medium (conc. 5×) were tested in 1:2 serial dilution starting from (530 nM to 30 nM) and in a 1:5 serial dilution (7 nM to 7×10−2 nM) for the N4 ADC1 and isotype control. N4 ADC2 and isotype control were tested in 1:10 serial dilution starting from (530 nM to 5.3 10-2). The ADCs' ability to cause cell death was determined by assessing confluence using Incucyte S3-2 apparatus; viability at day 6 after treatment was determined using the Cell Titer Glo™ (CTG) assay with an Enspire2 apparatus. IC50 values for each ADC was determined using Luminescent Cell Viability at day 6 data with GraphPad Prism8. Experiments were repeated twice.

Figure 3:
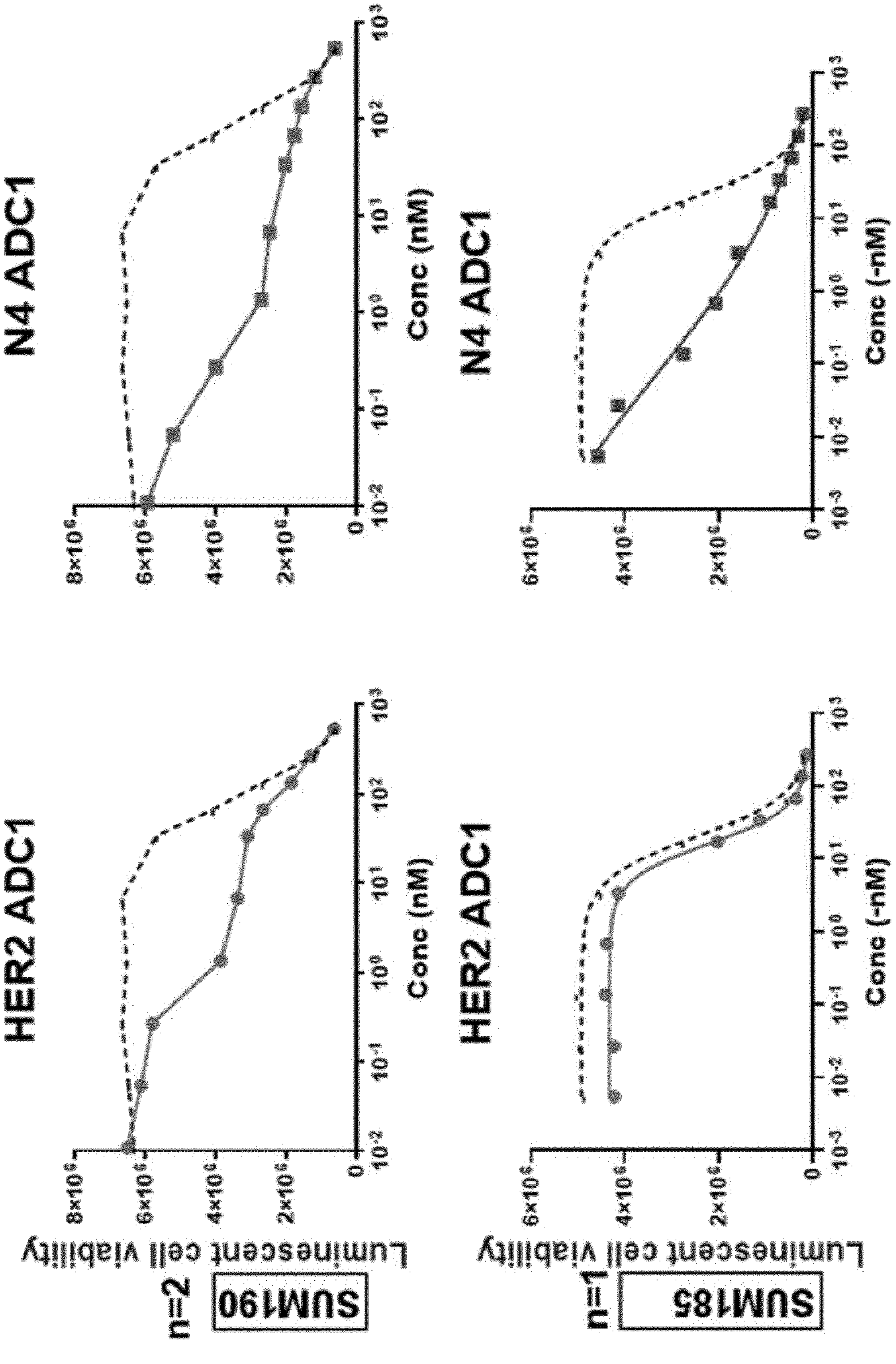
FIG. 3, right hand panels show efficacy of N4 ADC1 (anti-Nectin-4) in causing the death of HER-2 and Nectin-4 expressing SUM185 and SUM190 tumor cells. The two left hand panels of shows the efficacy of the HER2 ADC1 (anti-Her2) in the same respective cells. N4 ADC1 had a 20-fold increase in potency compared to HER2 ADC1 in the SUM190 cells, as well as higher comparative potency even in the SUM185 cells characterized by lower Nectin-4 surface expression (about 4-fold lower surface Nectin-4 in SUM185 than in SUM190).

Representative results are shown in FIG. 3. The two right hand panels of FIG. 3 shows that the N4 ADC1 (anti-Nectin-4) was effective in causing the death of tumor cells, with N4 ADC1 shown as solid line with squares and the isotype control as dashed line. The two left hand panels of FIG. 3 shows the efficacy of the Her2 ADC1 (anti-Her2) in the same respective cells, with HER2 ADC1 shown as solid lines with dots and the isotype control as dashed line. $IC_{50}$ values are summarized in the table, below. N4 ADC1 was particularly potent even in the SUM190 cells characterized by much lower Nectin-4 surface expression (about 4-fold lower surface Nectin-4 in SUM190 than inSUM185). The N4 ADC2 (anti-Nectin-4) bearing the camptothecin analogue SN38 showed good potency as well (see $IC_{50}$ Table, below).

TABLE

IC50 vales of ADCs

| $IC_{50}$ (nM) | SUM190 | SUM185 |
|---|---|---|
| Anti-Nectin-4 ADC (N4 ADC1) | 0.1 | 0.05 |
| Anti-Nectin-4 SN-38 ADC (N4 ADC2) | 0.4 | Not tested |
| Anti-HER2 ADC (Her2 ADC1) | 0.6 | 2 |

The results show that anti-Nectin-4 ADC (N4 ADC1) was considerably more potent than the anti-Her2 ADC (Her2 ADC1) in the SUM185 that express Nectin-4, with an $IC_{50}$ that was 40 times lower for the Nectin-4 ADCs. Of note, the SUM185 cells express Nectin-4 at relatively high levels, with Nectin-4 expression levels about twice that of Her2 in these cells (see Example 1). Interestingly, however, when the anti-Nectin-4 (N4 ADC1) and anti-Her2 (Her-2 ADC1) ADCs were tested in the SUM190 cells that have far lower levels of Nectin-4 surface expression, the anti-Nectin-4 ADC (N4 ADC1) remained highly potent. In these SUM190 cells the Nectin-4 surface expression was only half that of the Her2, yet the anti-Nectin-4 camptothecin ADCs remained at least as potent, or possibly more potent, than the anti-Her2 ADCs, with an $IC_{50}$ that was 6-fold lower for the anti-Nectin-4 ADCs than for the anti-anti-Her2 ADCs.

The combination of intracellularly cleavable peptide linker together with the camptothecin analogue compounds may therefore represent an effective means for eliminating Nectin-4-expressing tumor cells, including those characterized by lower Nectin-4 expression levels, without improved off-target toxicity compared to the most widely used cytotoxic agents such as pyrrolobenzodiazepines and auristatins. The anti-Nectin-4 ADCs may also provide a valuable approach to treating HER2-positive cancers, including but not limited to HER2-low and/or HER2-moderate expressing cancers.

Example 3: Efficacy of Anti-Nectin-4 Camptothecin-Analogue ADCs in Combination with Anti-HER2 ADCs Anti-Nectin-4 ADCs (N4 ADC1) and anti-Her2 ADCs (Her2 ADC1) were tested to evaluate their ability to cause tumor cell death when used in combination.

The anti-Nectin-4 camptothecin-analogue ADCs used were the N4 ADC1 as shown in Example 2. The anti-Her2 ADCs were also those used in Example 2 (Her2 ADC1). The ADC's ability to cause cell death was determined by assessing confluence and determining viability of SUM190 cells at day 6 as described in Example 2. Results showed that the combination of anti-Nectin-4 ADCs and anti-Her2 ADCs had an improved potency (lower IC50) in causing the death of the Nectin-4+ Her2+ tumor cells compared to either ADC alone.

Example 4: Intracellular Internalization

The ability of the anti-nectin-4 antibodies to induce nectin-4 internalization was assessed on SUM190 cell lines expressing lower levels of nectin-4 and in SUM185 cells expressing higher levels of Nectin-4. Antibodies tested were enfortumab (VH and VL of SEQ ID NOS: 3 and 4 as human IgG1 isotype) and N41 (VH and VL of SEQ ID NOS: 9 and 10 as human IgG1 isotype). Internalization was indirectly determined by using the Fab-ZAP human Internalization Kit (Advanced Targeting Systems) to allow the anti-Nectin-4 antibodies to target and eliminate Nectin-4 expressing cells, with measurement of cell viability using the CTG substrate (CellTiter-Glo® Luminescent Cell Viability Assay (Promega). Fab-ZAP is a chemical conjugate of goat anti-human monovalent antibody and the ribosome-inactivating protein, saporin. The antibodies used are affinity-purified polyclonal antibodies against both the heavy and light chain of human IgG. This secondary conjugate is used to evaluate the potential of a primary antibody to internalize.

Briefly, a concentration range of the antibodies or the control items was incubated on top of the SUM190 or SUM185 cells. After the incubation, the non-bound antibodies were washed away and Fab-ZAP was added on top of the cells. The newly formed complexes (anti-nectin-4 antibody+Fab-ZAP) internalized into the cells where the Saporin was released and stopped the protein synthesis leading to cell death. The internalization capability of the antibody was indirectly determined by the cells viability: the more efficient was the cell killing; the better was the internalization capability of the antibody.

Figure 4:
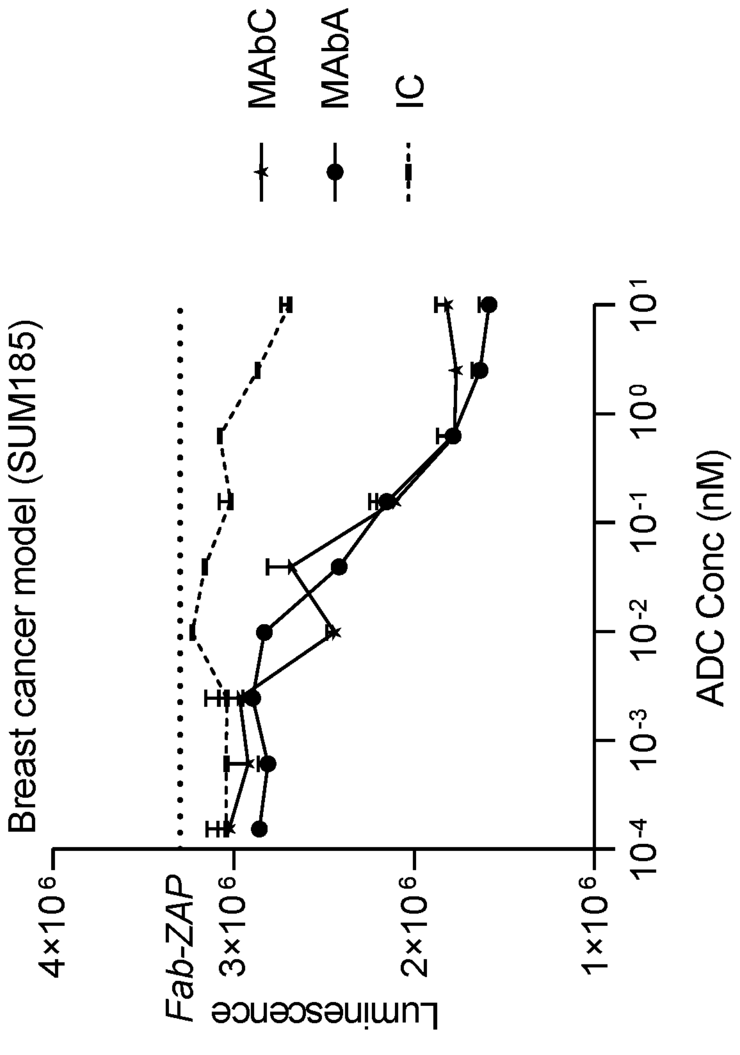
FIG. 4 shows internalization on human SUM185 breast cancer cells, as luminescence (indicating cell viability) on the Y-axis vs. anti-Nectin-4 antibody concentration on the X-axis, for antibodies enfortumab (mAbA) and N41 mAbC), as well as isotype control antibody (IC).

Luminescence vs. anti-Nectin-4 antibody concentration was plotted on graphs for each antibody. Results are shown in FIG. 4. Both enfortumab and N41 were both highly potent in the ability to induce of internalization, both in SUM185 cells and in SUM190 cells.

Example 5

Binding to Anchored Nectin-4 Domain-Deletion Proteins

The internalizing antibodies enfortumab and N41 were assessed for their ability to bind different domains on human Nectin-4.

The wild-type huNectin4 protein is composed of three extracellular Ig-like domains (V, C1 and C2) summarized in Table 1 below.

TABLE 1

| Designations | Positions | Description | Amino acid sequence |
|---|---|---|---|
| V domain | 32-144 | Ig-like V type | GELETSDVVTVVLGQ DAKLPCFYRGDSGEQ VGQVAWARVDAGEGA QELALLHSKYGLHVS PAYEGRVEQPPPPRN PLDGSVLLRNAVQAD EGEYECRVSTFPAGS FQARLRLR (SEQ ID NO: 2) |
| C1 domain | 148-237 | Ig-like C2 type 1 | PPLPSLNPGPALEEG QGLTLAASCTAEGSP APSVTWDTEVKGTTS SRSFKHSRSAAVTSE FHLVPSRSMNGQPLT CVVSHPGLLQDQRIT (SEQ ID NO: 11) |
| C2 domain | 248-331 | Ig-like C2 type 2 | ASVRGLEDQNLWHIG REGAMLKCLSEGQPP PSYNWTRLDGPLPSG VRVDGDTLGFPPLTT EHSGIYVCHVSNEFS SRDSQVTVDVLDPQE DSGKQVDLVSASV (SEQ ID NO: 12) |

The characterization of the binding of the antibodies on Nectin-4 domains was performed by flow cytometry using cells made to express the wild-type human Nectin-4 protein and cells made to express a modified Nectin-4 having the Ig-like C2 type 1 and the Ig-like C2 type 2 domains and lacking the Ig-like V domain (the C1C2 construct). The latter protein additionally bears a V5 tag for flow cytometry cell sorting, and cells were used as Nectin4-C1C2-V5 sorted cells.

Wild-type Nectin-4 (the CI.3C8 cell line), a C2 construct (containing the Ig-like C2 type 2 domain and lacking both the V and the C1 domains) and the C1C2 construct allow the determination of whether test antibodies bind to the V or different C domains. Briefly, nucleic acid sequences encoding different human Nectin-4 domains were amplified by PCR. The PCR products were inserted into an expression vector at appropriate restriction sites. A leader peptide, and for C1C2 and C2 an N-terminal V5 tag having the amino acid sequence GKPIPNPLLGLDST (SEQ ID NO: 13), were added, and expression at the surface of cells was confirmed by flow cytometry. The amino acid sequences of the resulting different human Nectin-4 domain fragment-containing proteins are shown below (V5 tag underlined). The vectors were then transfected into the CHO cell line to obtain stable clones expressing the different Nectin-4 domain proteins at the cell surface.

Nectin-4 amino acid sequence in the huNectin4 CI.3C8 cell line (wild type Nectin-4):

(SEQ ID NO : 14)

GELETSDVVTVVLGQDAKLPCFYRGDSGEQVGQVAWARVDAGEG

AQELALLHSKYGLHVSPAYEGRVEQPPPPRNPLDGSVLLRNAVQ

ADEGEYECRVSTFPAGSFQARLRLRVLVPPLPSLNPGPALEEGQ

GLTLAASCTAEGSPAPSVTWDTEVKGTTSSRSFKHSRSAAVTSE

FHLVPSRSMNGQPLTCVVSHPGLLQDQRITHILHVSFLAEASVR

GLEDQNLWHIGREGAMLKCLSEGQPPPSYNWTRLDGPLPSGVRV

DGDTLGFPPLTTEHSGIYVCHVSNEFSSRDSQVTVDVLDPQEDS

GKQVDLVSASVVVVGVIAALLFCLLVVVVVLMSRYHRRKAQQMT

QKYEEELTLTRENSIRRLHSHHTDPRSQPEESVGLRAEGHPDSL

KDNSSCSVMSEEPEGRSYSTLTTVREETQTELLSPGSGRAEEEE

DQDEGIKQAMNHFVQENGTLRAKPTGNGIYINGRGHLV.

Nectin-4 amino acid sequence in the huNectin4-C1C2-V5 cell line (lacking V domain):

(SEQ ID NO : 15)

PPLPSLNPGPALEEGQGLTLAASCTAEGSPAPSVTWDTEVKGTT

SSRSFKHSRSAAVTSEFHLVPSRSMNGQPLTCVVSHPGLLQDQR

ITHILHVSFLAEASVRGLEDQNLWHIGREGAMLKCLSEGQPPPS

YNWTRLDGPLPSGVRVDGDTLGFPPLTTEHSGIYVCHVSNEFSS

RDSQVTVDVLDPQEDSGKQVDLVSASWWGVIAALLFCLLWWVLM

SRYHRRKAQQMTQKYEEELTLTRENSIRRLHSHHTDPRSQPEES

VGLRAEGHPDSLKDNSSCSVMSEEPEGRSYSTLTTVREIETQTE

LLSPGSGRAEEEEDQDEGIKQAMNHFVQENGTLRAKPTGNGIYI

NGRGHLV.

-continued

Nectin-4 amino acid sequence in the huNectin4-C2-V5 cell line (lacking V and C1 domains):

(SEQ ID NO: 16)

ASVRGLEDQNLWHIGREGAMLKCLSEGQPPPSYNWTRLDGPLPS

GVRVDGDTLGFPPLTTEHSGIYVCHVSNEFSSRDSQVTVDVLDP

QEDSGKQVDLVSASVVVVGVIAALLFCLLVVVVVLMSRYHRRKA

QQMTQKYEEELTLTRENSIRRLHSHHTDPRSQPEESVGLRAEGH

PDSLKDNSSCSVMSEEPEGRSYSTLTTVREIETQTELLSPGSGR

AEEEEDQDEGIKQAMNHFVQENGTLRAKPTGNGIYINGRGHLV.

The internalizing antibodies N41 and enfortumab both bound to the whole Nectin-4 protein and lost binding to the C1C2 construct that lacked the V domain. N41 and enfortumab thus bind to Nectin-4 within the V domain.

Example 6: In Vitro Cytotoxicity of an Exatecan ADC on Breast Cancer Cells (Nectin-4 High/SUM185 Model)

We assessed killing of SUM185 cells by the anti-Ig-like V domain antibody enfortumab (mAbA) having VH and VL of SEQ ID NOS: 3 and 4 as human IgG1 isotype conjugated to exatecan. In this experiment, the enfortumab antibody was tested along with a control antibody conjugated with the same toxin at equivalent drug to antibody ratios. ADCs were prepared in which antibodies were conjugated to an exatecan via the linker shown below comprising a spacer, an intracellularly cleavable dipeptide valine-citrulline (VC), and PAB self-eliminating spacer, at 8 toxins per antibody (DAR=8):

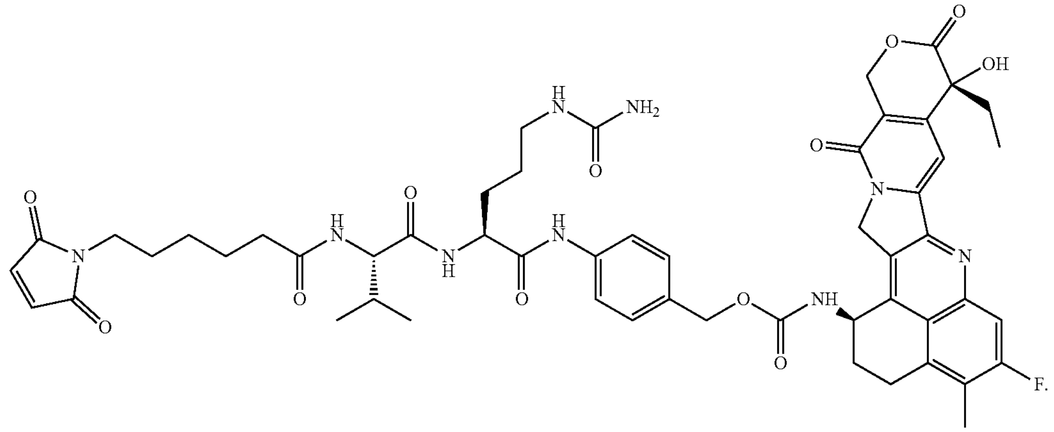

(VC-exatecan)

-

For each ADC, a concentration range of ADC was incubated on top of nectin-4-expressing cells. After incubation, the CTG substrate was added at 1/1 ratio and the luminescent signal was read with a plate reader (Enspire), allowing quantification of the ATP present (indicator of metabolically active cells) which was proportional to cell viability.

Figure 5:
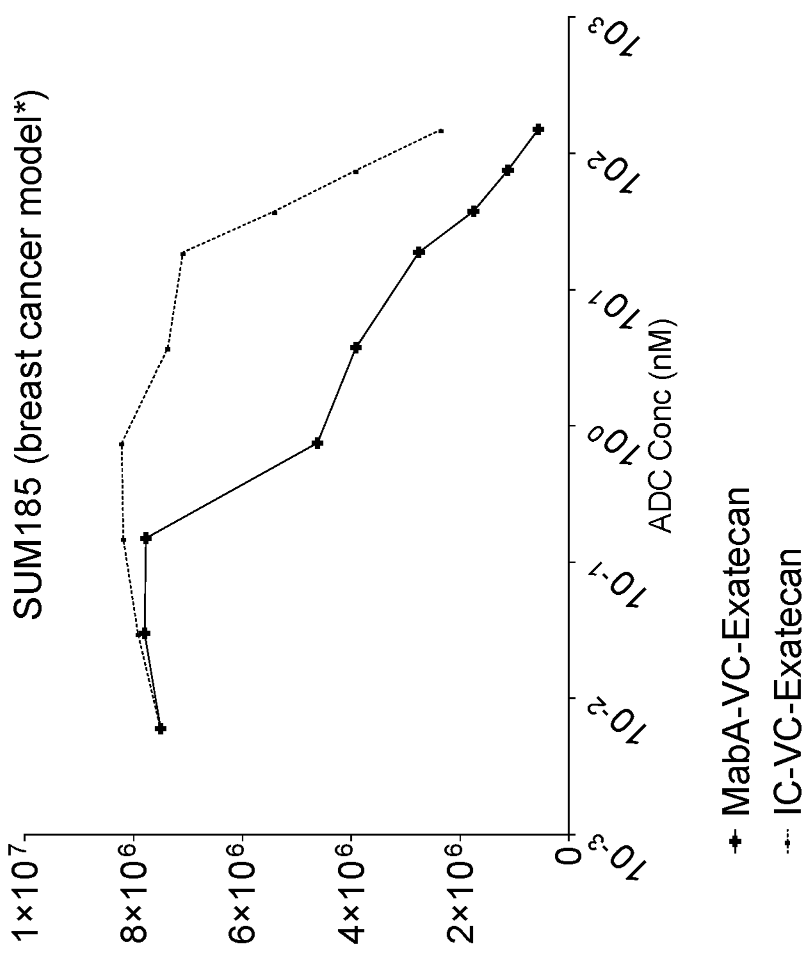
FIG. 5 shows killing of human SUM185 breast cancer cells, as cell viability on the Y-axis vs. anti-Nectin-4 antibody concentration on the X-axis, by the anti-Ig-like V domain antibody enfortumab (mAbA) and isotype control (IC) conjugated to exatecan via a linker having a first spacer, a Val-Cit cleavable moiety and a PAB self-eliminating spacer (VC-exatecan).

Results are shown in FIG. 5. mAbA-VC-exatecan was able to kill the SUM185 more efficiently than the non-targeted isotype control ADC (IC-VC-exatecan).

Example 7: In Vitro Cytotoxicity of an Exatecan and Dxd ADCs on Breast Cancer Cells (Nectin-4 Low/SUM190 Model)

The anti-Ig-like V domain antibody enfortumab (mAbA) was conjugated to either exatecan via the VC-exatecan linker having the structure shown in Example 6, or to the camptothecin analogue DxD via the intracellularly cleavable tetrapeptide linker, referred to as GGFG-DxD. An isotype control (IC) antibody was also conjugated for each linker. Each linker was conjugated to the antibody at 8 toxins per antibody (DAR=8).

The structure of the GGFG-DxD linker (GGFG-DxD) was:

(GGFG-DxD)

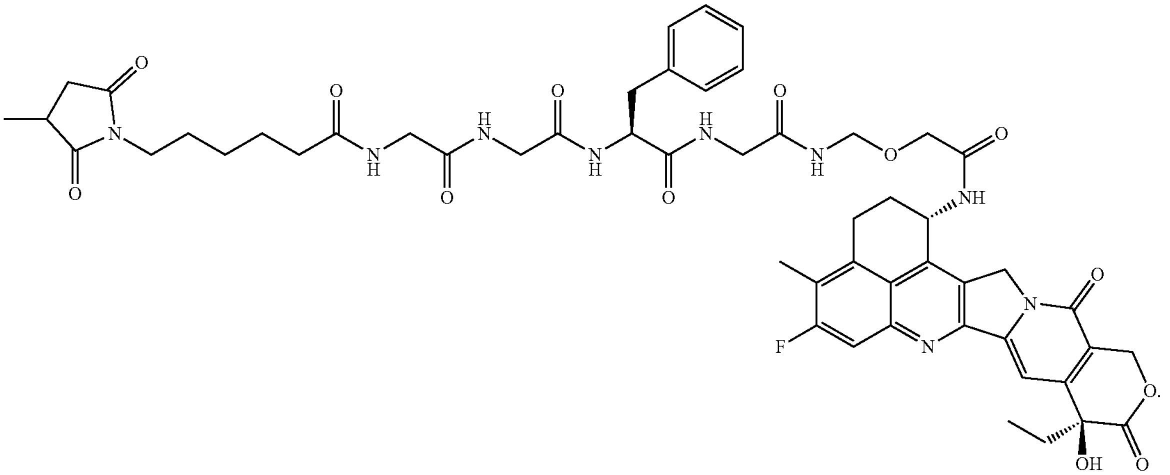

Figure 6:
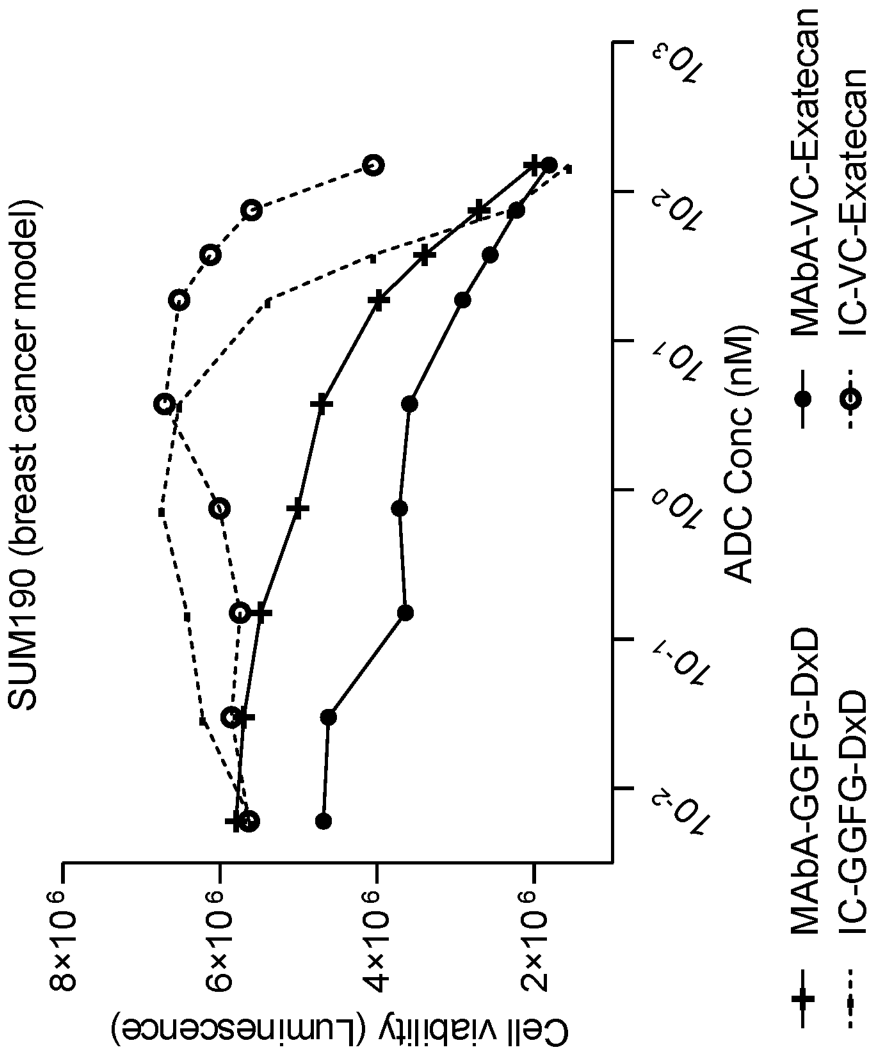
FIG. 6 shows killing of human SUM190 breast cancer cells, as cell viability on the Y-axis vs. anti-Nectin-4 antibody concentration on the X-axis, by the anti-Ig-like V domain antibody enfortumab (mAbA) and isotype control (IC) conjugated to either exatecan via the VC-exatecan linker or to the camptothecin DxD via a GGFG cleavable linker (GGFG-DxD).

In vitro cytotoxicity was assessed as in Example 6. Results are shown in FIG. 6. The mAbA-VC-exatecan immunoconjugate was able to kill the Nectin-4 low expressing SUM190 cells more efficiently than the mAbA-GGFG-DxD immunoconjugate.

Example 8: In Vitro Cytotoxicity of an Exatecan ADCs with Different Cleavable Linkers on Breast Cancer Cells (Nectin-4 Low/SUM190 Model)

We assessed killing of SUM190 cells by the anti-Ig-like V domain antibody enfortumab (mAbA) having VH and VL of SEQ ID NOS: 3 and 4 as human IgG1 isotype conjugated to exatecan, either via a valine-citrulline-PAB linker, a valine-alanine-PAB linker, or a PEG8-valine-alanine-PAB linker. In each case the enfortumab was tested along with an isotype control (IC) antibody conjugated with the same toxin at equivalent drug to antibody ratios. ADCs were prepared in which antibodies were conjugated to an exatecan via the linker at 8 toxins per antibody (DAR=8).

The structure of the valine-citrulline-PAB linker (VC-exatecan) was as shown in Example 6. The structure of the PEG8-valine-citrulline-PAB linker (PEG8-VC-exatecan) is shown herein as Compound 6.

The structure of the valine-alanine-PAB linker (VA-exatecan) was:

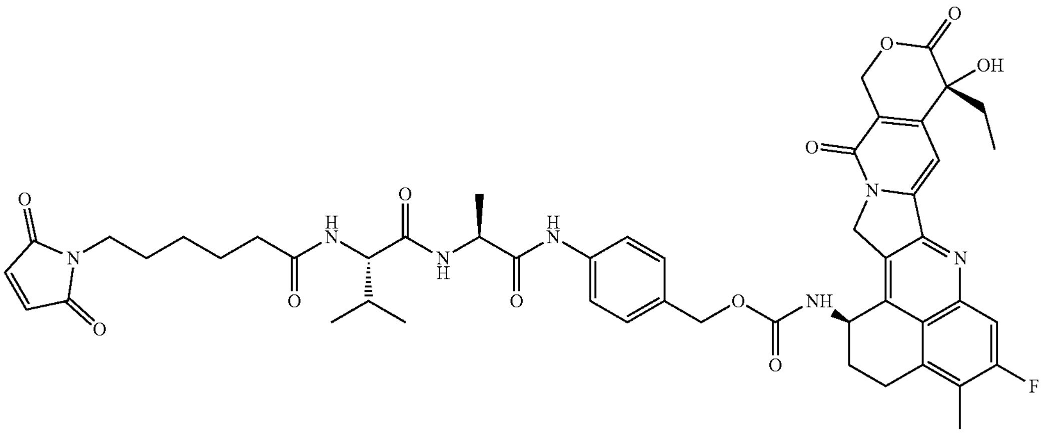 [SMILES: CC[C@]1(O)C(=O)OCc2c1cc1n(c2=O)Cc2c-1nc1cc(F)c(C)c3c1c2[C@H](NC(=O)OCc1ccc(NC(=O)[C@H](C)NC(=O)[C@@H](NC(=O)CCCCCN2C(=O)C=CC2=O)C(C)C)cc1)CC3]

The structure of the PEG8-valine-alanine-PAB linker (PEG8-VA-exatecan) was:

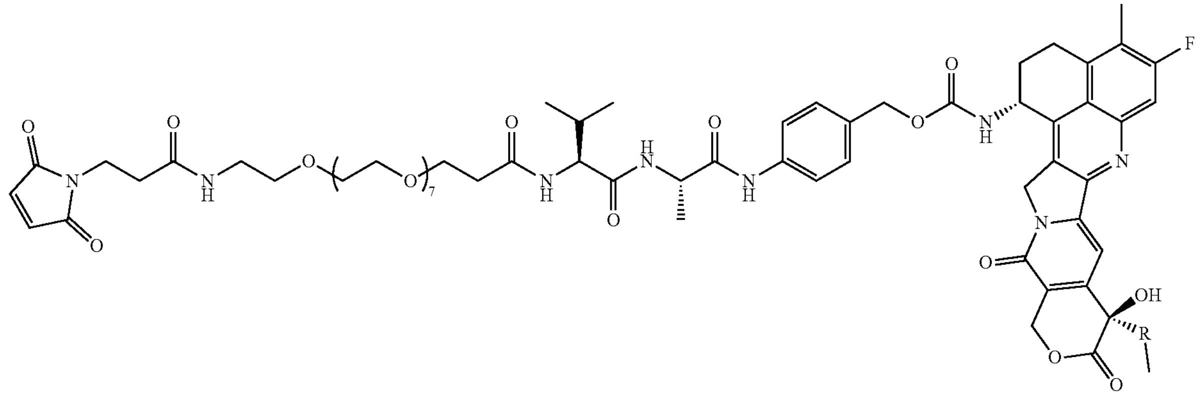

1 - Mal-PEG(8u)-Val-Ala-PAB-Exatecan

Figure 7:
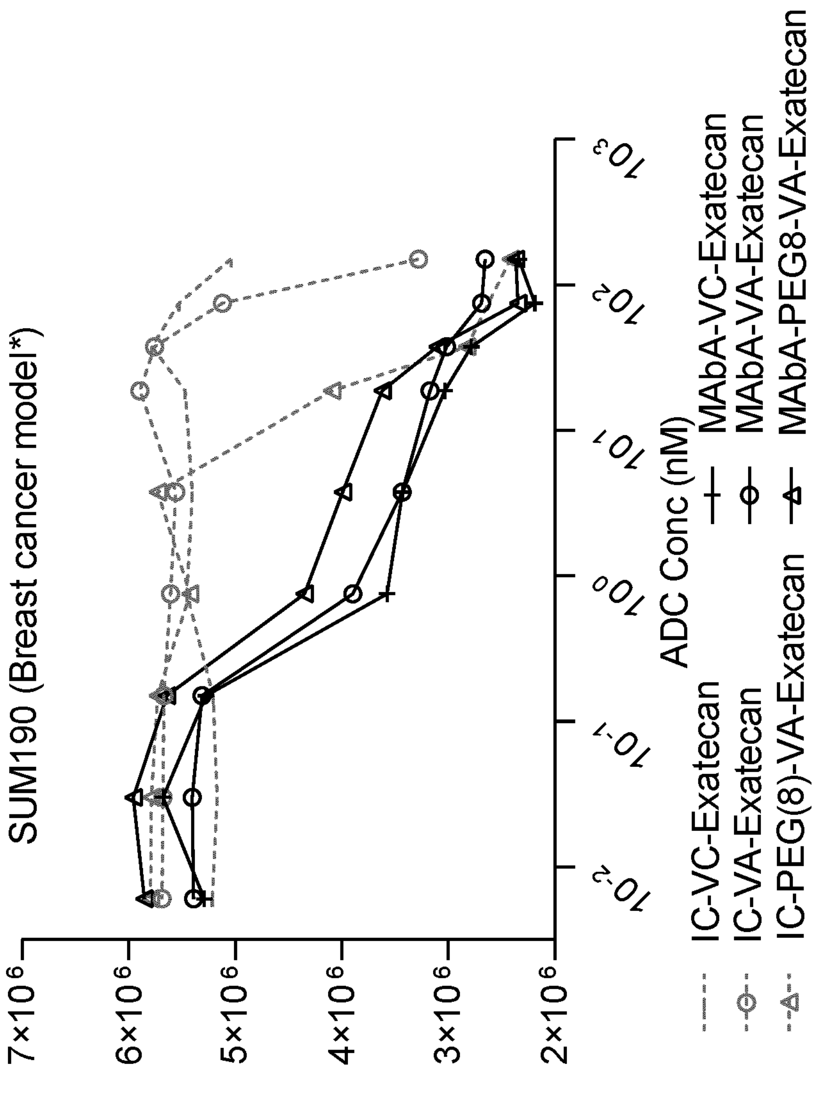
FIG. 7 shows killing of human SUM190 breast cancer cells, as cell viability on the Y-axis vs. anti-Nectin-4 antibody concentration on the X-axis, by the anti-Ig-like V domain antibody enfortumab (mAbA) and isotype control (IC) conjugated to exatecan either via the VC-exatecan linker, via a linker having a first spacer, a Val-Ala cleavable moiety and a PAB self-eliminating spacer (VC-exatecan), or via a VC-exatecan linker in which the first spacer comprises a PEG8 moiety (8 PEG units).

In vitro cytotoxicity was assessed as in Example 6. Results are shown in FIG. 7. Each of the exatecan linkers when conjugated to mAbA permitted efficient killing of the Nectin-4 low expressing SUM190 cells.

Example 9: In Vivo Efficacy of ADCs in a Mouse Model of Human Breast Cancer (Nectin-4 Low/SUM190 Model)

We compared the in vivo efficacy of enfortumab (mAbA) isotype control (IC) antibody, each conjugated to exatecan, either via a valine-citrulline-PAB linker (VC-exatecan), a valine-alanine-PAB linker (VA-exatecan) or a PEG8-valine-alanine-PAB linker (PEG8-VA-exatecan). Also tested was the six-ring camptothecin analogue DxD conjugated to the antibody via an intracellularly cleavable tetrapeptide linker (GGFG-DxD). Each linker and toxin was conjugated at equivalent drug to antibody ratios of 8 toxins per antibody (DAR=8).

SUM190 cells were subcutaneously injected in CB17-SCID immunodeficient mice at a dose of 0.5 million cells in 100 μl of Matrigel with growth factor diluted at ½ in PBS. When tumors reached a volume between 195 and 250 mm3, mice were randomized into groups for intravenous treatment with a single injection of 5 mg/kg of camptothecin ADCs. Tumor growth were followed twice a week. Kaplan Meier survival curves were established by using GraphPad Prism V7 software according to the following criteria: When the tumor volume reached 1500 $mm^3$, mice were euthanized and considered dead on the day of sacrifice. When tumors showed signs of necrosis, mice were euthanized and considered dead on the same day.

Figure 8:
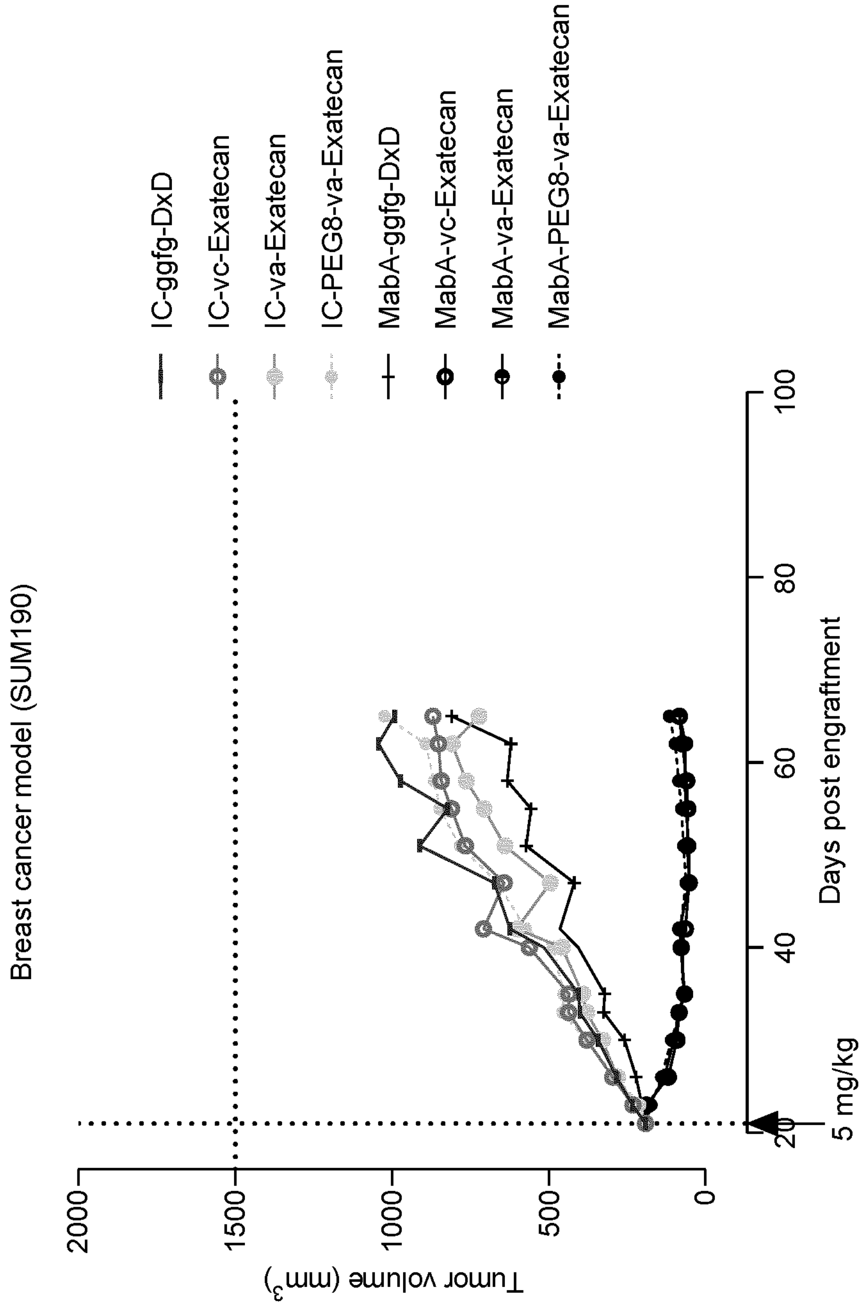
FIG. 8 shows the in vivo efficacy at a single dose of 5 mg/kg of camptothecin ADCs based on enfortumab (mAbA), conjugated either to the GGFG-DxD linker, the VC-exatecan linker, the VA-exatecan linker, or the PEG8-VA-exatecan linker, at equivalent drug to antibody ratios (DAR=8).

Results showed that at the 5 mg/kg dose VC-exatecan, VA-exatecan and PEG8-VA-exatecan were all similarly efficient in preventing increase in tumor volume, and that all were more effective than GGFG-DxD in preventing increase in tumor volume. Results are shown in FIG. 8.

Example 10: Effect of Different Antibodies on ADC Efficacy in a Mouse Model of Human Breast Cancer (Nectin-4 Low/SUM190 Model)

We compared the in vivo efficacy of enfortumab (mAbA) and another Nectin-4 binding antibody that bound at least partly to the IgV domain of Nectin-4 (mAbB), when each were conjugated to exatecan via the same PEG8-valine-alanine-PAB linker (PEG8-VA-exatecan). Also tested were isotype control (IC) antibody coupled to PEG8-VA-exatecan, and the six-ring camptothecin analogue DxD conjugated via an intracellularly cleavable tetrapeptide linker (GGFG-DxD). Each linker and toxin was conjugated at equivalent drug to antibody ratios of 8 toxins per antibody (DAR=8).

SUM190 cells were subcutaneously injected in CB17-SCID immunodeficient mice at a dose of 0.5 million cells in 100 μl of Matrigel with growth factor diluted at ½ in PBS. When tumors reached a volume between 195 and 250 mm3, mice were randomized into groups for intravenous treatment with a single injection of 5 mg/kg of camptothecin ADCs. Tumor growth were followed twice a week. Kaplan Meier survival curves were established by using GraphPad Prism V7 software according to the following criteria: When the tumor volume reached 1500 $mm^3$, mice were euthanized and considered dead on the day of sacrifice. When tumors showed signs of necrosis, mice were euthanized and considered dead on the same day.

Figure 9:
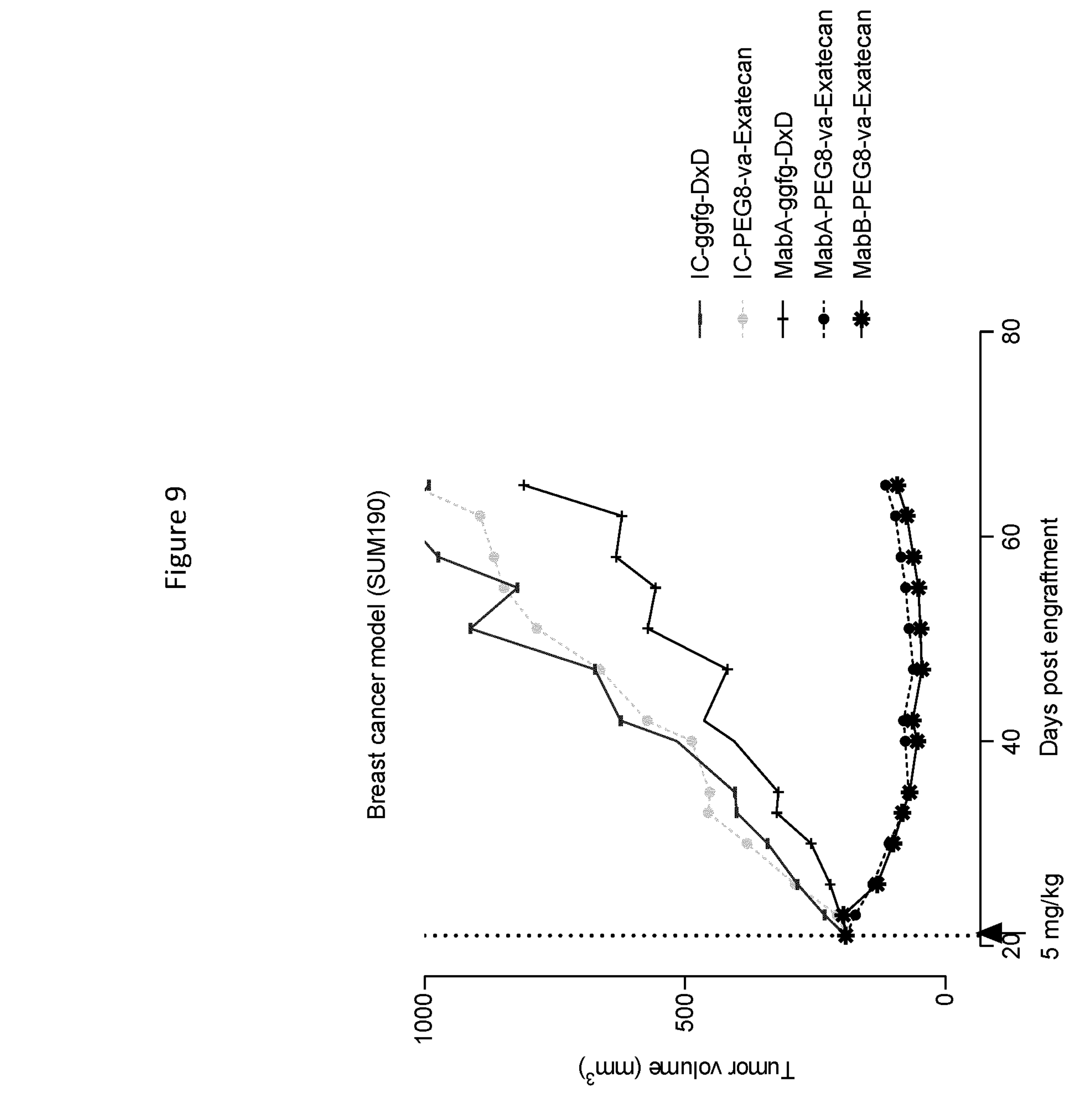
FIG. 9 shows the in vivo efficacy at a single dose of 5 mg/kg of camptothecin ADCs for two different anti-Nectin-4 antibodies. Either enfortumab (mAbA) or an alternate anti-Nectin-4 specific antibody (mAbB) were each conjugated the PEG8-VA-exatecan linker, at equivalent drug to antibody ratios (DAR=8). Enfortumab (mAbA) conjugated to the GGFG-DxD linker, and isotype control, were also tested for comparison.

Results showed that at the 5 mg/kg dose mAbA-PEG8-VA-exatecan and mAbB-PEG8-VA-exatecan were similarly efficient in preventing increase in tumor volume. Both were more effective than mAbA-GGFG-DxD in preventing increase in tumor volume. Results are shown in FIG. 9.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate). Where "about" is used in connection with a number, this can be specified as including values corresponding to +/−10% of the specified number.

The description herein of any aspect or embodiment of the invention using terms such as "comprising", "having," "including," or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method of treating cancer in an individual comprising administering an anti-Nectin-4 antibody conjugated to a linker-exatecan moiety comprising Val-Ala-PAB-exatecan, wherein the exatecan molecule is coupled to PAB via the nitrogen atom of the amino group at position 1, such that the exatecan moiety when bound to the linker has the structure of Compound 1b:

Compound 1b

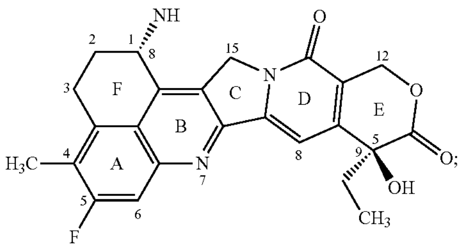

and wherein the cancer has relapsed and/or has progressed following treatment with a Nectin-4-binding agent conjugated to an auristatin.

2. The method according to claim 1, wherein the Nectin-4-binding agent conjugated to an auristatin is enfortumab vedotin.

3. The method according to claim 1, wherein said cancer is a urothelial cancer.

4. The method according to claim 1, wherein said cancer is HER2 positive.

5. The method according to claim 1, wherein the treatment of a cancer in an individual is independent of the assessment or detection of levels of Nectin-4 expression in tumors.

6. The method according to claim 1, wherein the treatment a cancer in an individual comprises a preliminary step of determining whether said individual has tumor cells expressing Nectin-4.

7. The method according to claim 1, wherein the anti-Nectin-4 antibody conjugated to an exatecan releases a molecule of Compound la:

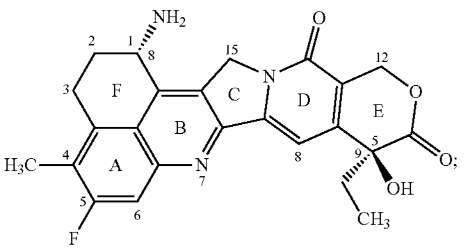

in vivo in tumor cells.

8. The method according to claim 1, wherein the anti-Nectin-4 antibody is capable of inducing intracellular internalization of Nectin-4 in tumor cells that express Nectin-4 at their surface.

9. The method according to claim 1, wherein the anti-Nectin-4 antibody conjugated to exatecan has an exatecan molecule to antibody ratio of 8, and wherein the ratio of exatecan molecule to linker is 1.

* * * * *